US008722366B2

(12) United States Patent
Sasaki et al.

(10) Patent No.: US 8,722,366 B2
(45) Date of Patent: May 13, 2014

(54) METHODS FOR SYNTHESIZING SUGAR CHAINS USING β1,3-N-ACETYLGLUCOSAMINYLTRANSFERASE

(75) Inventors: Katsutoshi Sasaki, Sagamihara (JP); Norihiko Shiraishi, Tokyo (JP); Ayumi Natsume, Tokyo (JP); Yoji Yamada, Tokyo (JP); Satoshi Nakagawa, Tokyo (JP); Susumu Sekine, Yokohama (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 103 days.

(21) Appl. No.: 13/164,814

(22) Filed: Jun. 21, 2011

(65) Prior Publication Data

US 2012/0156732 A1 Jun. 21, 2012

Related U.S. Application Data

(62) Division of application No. 12/019,793, filed on Jan. 25, 2008, now Pat. No. 7,972,815, which is a division of application No. 11/148,280, filed on Jun. 9, 2005, now abandoned, which is a division of application No. 10/019,735, filed as application No. PCT/JP00/04304 on Jun. 29, 2000, now Pat. No. 7,005,279.

(30) Foreign Application Priority Data

Jun. 29, 1999 (JP) .................................... 11-183437
Mar. 16, 2000 (JP) .................................. 2000-74757

(51) Int. Cl.
*C12P 19/26* (2006.01)
*C12P 19/18* (2006.01)

(52) U.S. Cl.
USPC ............... 435/84; 435/97; 435/193; 536/23.2

(58) Field of Classification Search
None
See application file for complete search history.

(56) References Cited

U.S. PATENT DOCUMENTS

2001/0024808 A1* 9/2001 White et al. ................. 435/69.1

FOREIGN PATENT DOCUMENTS

| | | |
|---|---|---|
| WO | 98/21328 | 5/1998 |
| WO | 98/44112 | 10/1998 |
| WO | 00/15826 | 3/2000 |
| WO | 01/85177 | 11/2001 |

OTHER PUBLICATIONS

T. Hennet et al. "Genomic Cloning and Expression of Three Murine UDP-galactose:B-N-Acetylglucosamine B-1,3-Galactosyltransferase Genes", J. Biol. Chem. 273(1):58-65. (Jan. 1998).*
F. Kolbinger et al. "Cloning of a Human UDP-galactose:2-Acetamido-2-deoxy-D-glucose 3B-Galactosyltransferase Catalyzing the Formation of Type 1 Chains", J. Biol. Chem. 273(1):433-440. (Jan. 1998).*
Zhou, et al., "*Homo sapiens* beta-1,3-N-acetylglucosaminyltransferase mrRNA, complete cds", XP-002205662, GenBank Accession No. AF092051 (Aug. 2000).
Di Virgillio, et al., "Enzymatic synthesis of natural and C-13 enriched linear poly-N-acetyllactosamines as ligands for galectin-1", Glycobiology, vol. 9, No. 4 (1999), 353-64.
Zhou, et al., "A Beta-1,3-N-acetylglucosaminyltransferase with poly-N-acetyllactosamine synthase activity is structurally related to . . . ", PNAS, vol. 96 (1999), 406-11.
Sasaki, et al., "Expression cloning of cDNA encoding a human beta-1,3-N-acetylglucosaminyltransferase that is essential for poly-N-acetyllactosamine synthesis", PNAS, vol. 94 (1997), 14294-299.
Almeida, et al., "A Family of Human b-4-Galactosyltransferases. Cloning and Expression of Two Novel UDP-Galactose: b-N-Acetylglucosamine b-1,4-Galactosyltranferases . . . ", J. Biol. Chem., vol. 272, No. 51 (1997), 31979-91.
Schwientek, et al., "Cloning of a Novel Member of the UDP-Galactose: beta-N-Acetylglucosamine beta1,4-Galactosyltransferase Family . . . ", J. Biol. Chem., vol. 273, No. 45 (1998), 29331-40.

* cited by examiner

*Primary Examiner* — Rebecca Prouty
(74) *Attorney, Agent, or Firm* — Fitzpatrick, Cella, Harper & Scinto

(57) ABSTRACT

The present invention provides a novel polypeptide having a β1,3-N-acetylglucosaminyltransferase activity; a method for producing the polypeptide; a DNA which encodes the polypeptide; a recombinant vector into which the DNA is inserted; a transformant comprising the recombinant vector; a method for producing a sugar chain or complex carbohydrate, using the polypeptide; a method for producing a sugar chain or complex carbohydrate, using the transformant; an antibody which recognizes the polypeptide; a method for screening a substance which changes the expression of the gene which encodes the polypeptide; and a method for screening a substance which changes the activity of the polypeptide.

3 Claims, 22 Drawing Sheets

```
1st Nucleotide Sequence
  File Name         : G4 cDNA.
  Sequence Size     : 2205

2nd Nucleotide Sequence
  File Name         : G4-2 cDNA
  Sequence Size     : 2180

   1' GGCCAGGAACCCGCAAGGCGCTGCTTGTTCATCTCCAGCCACGGGGAGCTCATTCCCTAG
                                         * *  * * * ** *        **
   1"                              CGCGAGCTGAGAGGAGCAGGTAGAGGGGCAG

  61' CAGCGGGCCAG---ACCCAAGGAGCCGCCCAGGAGGCTCCTCAGGCCGACCCCAGACCCT
        ***** * *    *    ****************************************
  32" AGGCGGGACTGTCGTCTGGGGGAGCCGCCCAGGAGGCTCCTCAGGCCGACCCCAGACCCT

 118' GGCTGGCCAGGATGAAGTATCTCCGGCACCGGCGGCCCAATGCCACCCTCATTCTGGCCA
      ************************************************************
  92" GGCTGGCCAGGATGAAGTATCTCCGGCACCGGCGGCCCAATGCCACCCTCATTCTGGCCA

 178' TCGGCGCTTTCACCCTCCTCCTCTTCAGTCTGCTAGTGTCACCACCCACCTGCAAGGTCC
      ************************************************************
 152" TCGGCGCTTTCACCCTCCTCCTCTTCAGTCTGCTAGTGTCACCACCCACCTGCAAGGTCC

 238' AGGAGCAGCCACCGGCGATCCCCGAGGCCCTGGCCTGGCCCACTCCACCCACCCGCCCAG
      ************************************************************
 212" AGGAGCAGCCACCGGCGATCCCCGAGGCCCTGGCCTGGCCCACTCCACCCACCCGCCCAG

 298' CCCCGGCCCCGTGCCATGCCAACACCTCTATGGTCACCCACCCGGACTTCGCCACGCAGC
      ************************************************************
 272" CCCCGGCCCCGTGCCATGCCAACACCTCTATGGTCACCCACCCGGACTTCGCCACGCAGC

 358' CGCAGCACGTTCAGAACTTCCTCCTGTACAGACACTGCCGCCACTTTCCCCTGCTGCAGG
      ************************************************************
 332" CGCAGCACGTTCAGAACTTCCTCCTGTACAGACACTGCCGCCACTTTCCCCTGCTGCAGG

 418' ACGTGCCCCCCTCTAAGTGCGCGCAGCCGGTCTTCCTGCTGCTGGTGATCAAGTCCTCCC
      ************************************************************
 392" ACGTGCCCCCCTCTAAGTGCGCGCAGCCGGTCTTCCTGCTGCTGGTGATCAAGTCCTCCC
```

Fig. 1

```
478'  CTAGCAACTATGTGCGCCGCGAGCTGCTGCGGCGCACGTGGGGCCGCGAGCGCAAGGTAC
      ************************************************************
452"  CTAGCAACTATGTGCGCCGCGAGCTGCTGCGGCGCACGTGGGGCCGCGAGCGCAAGGTAC

538'  GGGGTTTGCAGCTGCGCCTCCTCTTCCTGGTGGGCACAGCCTCCAACCCGCACGAGGCCC
      ************************************************************
512"  GGGGTTTGCAGCTGCGCCTCCTCTTCCTGGTGGGCACAGCCTCCAACCCGCACGAGGCCC

598'  GCAAGGTCAACCGGCTGCTGGAGCTGGAGGCACAGACTCACGGAGACATCCTGCAGTGGG
      ************************************************************
572"  GCAAGGTCAACCGGCTGCTGGAGCTGGAGGCACAGACTCACGGAGACATCCTGCAGTGGG

658'  ACTTCCACGACTCCTTCTTCAACCTCACGCTCAAGCAGGTCCTGTTCTTACAGTGGCAGG
      ************************************************************
632"  ACTTCCACGACTCCTTCTTCAACCTCACGCTCAAGCAGGTCCTGTTCTTACAGTGGCAGG

718'  AGACAAGGTGCGCCAACGCCAGCTTCGTGCTCAACGGGGATGATGACGTCTTTGCACACA
      ************************************************************
692"  AGACAAGGTGCGCCAACGCCAGCTTCGTGCTCAACGGGGATGATGACGTCTTTGCACACA

778'  CAGACAACATGGTCTTCTACCTGCAGGACCATGACCCTGGCCGCCACCTCTTCGTGGGGC
      ************************************************************
752"  CAGACAACATGGTCTTCTACCTGCAGGACCATGACCCTGGCCGCCACCTCTTCGTGGGGC

838'  AACTGATCCAAAACGTGGGCCCCATCCGGGCTTTTTGGAGCAAGTACTATGTGCCAGAGG
      ************************************************************
812"  AACTGATCCAAAACGTGGGCCCCATCCGGGCTTTTTGGAGCAAGTACTATGTGCCAGAGG

898'  TGGTGACTCAGAATGAGCGGTACCCACCCTATTGTGGGGGTGGTGGCTTCTTGCTGTCCC
      ************************************************************
872"  TGGTGACTCAGAATGAGCGGTACCCACCCTATTGTGGGGGTGGTGGCTTCTTGCTGTCCC

958'  GCTTCACGGCCGCTGCCCTGCGCCGTGCTGCCCATGTCTTGGACATCTTCCCCATTGATG
      ************************************************************
932"  GCTTCACGGCCGCTGCCCTGCGCCGTGCTGCCCATGTCTTGGACATCTTCCCCATTGATG

1018' ATGTCTTCCTGGGTATGTGTCTGGAGCTTGAGGGACTGAAGCCTGCCTCCCACAGCGGCA
      ************************************************************
992"  ATGTCTTCCTGGGTATGTGTCTGGAGCTTGAGGGACTGAAGCCTGCCTCCCACAGCGGCA
```

Fig.2

```
1078'  TCCGCACGTCTGGCGTGCGGGCTCCATCGCAACACCTGTCCTCCTTTGACCCCTGCTTCT
       ************************************ ***********************
1052"  TCCGCACGTCTGGCGTGCGGGCTCCATCGCAACGCCTGTCCTCCTTTGACCCCTGCTTCT

1138'  ACCGAGACCTGCTGCTGGTGCACCGCTTCCTACCTTATGAGATGCTGCTCATGTGGGATG
       ************************************************************
1112"  ACCGAGACCTGCTGCTGGTGCACCGCTTCCTACCTTATGAGATGCTGCTCATGTGGGATG

1198'  CGCTGAACCAGCCCAACCTCACCTGCGGCAATCAGACACAGATCTACTGAGTCAGCATCA
       ************************************************************
1172"  CGCTGAACCAGCCCAACCTCACCTGCGGCAATCAGACACAGATCTACTGAGTCAGCATCA

1258'  GGGTCCCCAGCCTCTGGGCTCCTGTTTCCAGAGGAAGGGGCGACACCTTCCTCCCAGGAA
       ******************************* ****************************
1232"  GGGTCCCCAGCCTCTGGGCTCCTGTTTCCATAGGAAGGGGCGACACCTTCCTCCCAGGAA

1318'  GCTGAGACCTTTGTGGTCTGAGCATAAGGGAGTGCCAGGGAAGGTTTGAGGTTTGATGAG
       ************************************************************
1292"  GCTGAGACCTTTGTGGTCTGAGCATAAGGGAGTGCCAGGGAAGGTTTGAGGTTTGATGAG

1378'  TGAATATTCTGGCTGGCGAACTCCTACACATCCTTCAAAACCCACCTGGTACTGTTCCAG
       ************************************************************
1352"  TGAATATTCTGGCTGGCGAACTCCTACACATCCTTCAAAACCCACCTGGTACTGTTCCAG

1438'  CATCTTCCCTGGATGGCTGGAGGAACTCCAGAAAATATGCATCTTCTTTTTGTGGCTGCT
       ***************************************  *******************
1412"  CATCTTCCCTGGATGGCTGGAGGAACTCCAGAAAATATCCATCTTCTTTTTGTGGCTGCT

1498'  AATGGCAGAAGTGCCTGTGCTAGAGTTCCAACTGTGGATGCATCCGTCCCGTTTGAGTCA
       ************************************************************
1472"  AATGGCAGAAGTGCCTGTGCTAGAGTTCCAACTGTGGATGCATCCGTCCCGTTTGAGTCA

1558'  AAGTCTTACTTCCCTGCTCTCACCTACTCACAGACGGGATGCTAAGCAGTGCACCTGCAG
       ************************************************************
1532"  AAGTCTTACTTCCCTGCTCTCACCTACTCACAGACGGGATGCTAAGCAGTGCACCTGCAG

1618'  TGGTTTAATGGCAGATAAGCTCCGTCTGCAGTTCCAGGCCAGCCAGAAACTCCTGTGTCC
       ************************************************************
1592"  TGGTTTAATGGCAGATAAGCTCCGTCTGCAGTTCCAGGCCAGCCAGAAACTCCTGTGTCC
```

Fig. 3

```
1678' ACATAGAGCTGACGTGAGAAATATCTTTCAGCCCAGGAGAGAGGGGTCCTGATCTTAACC
      ************************************************************
1652" ACATAGAGCTGACGTGAGAAATATCTTTCAGCCCAGGAGAGAGGGGTCCTGATCTTAACC

1738' CTTTCCTGGGTCTCAGACAACTCAGAAGGTTGGGGGGATACCAGAGAGGTGGTGGAATAG
      ************************************************************
1712" CTTTCCTGGGTCTCAGACAACTCAGAAGGTTGGGGGGATACCAGAGAGGTGGTGGAATAG

1798' GACCGCCCCCTCCTTACTTGTGGGATCAAATGCTGTAATGGTGGAGGTGTGGGCAGAGGA
      ************************************************************
1772" GACCGCCCCCTCCTTACTTGTGGGATCAAATGCTGTAATGGTGGAGGTGTGGGCAGAGGA

1858' GGGAGGCAAGTGT-CTTTGAAAGTTGTGAGAGCTCAGAGTTTCTGGGGTCCTCATTAGGA
      ************* **********************************************
1832" GGGAGGCAAGTGTCCTTTGAAAGTTGTGAGAGCTCAGAGTTTCTGGGGTCCTCATTAGGA

1917' GCCCCCATCCCTGTGTTCCCCAAGAATTCAGAGAACAGCACTGGGGCTGGAATGATCTTT
      ************************************************************
1892" GCCCCCATCCCTGTGTTCCCCAAGAATTCAGAGAACAGCACTGGGGCTGGAATGATCTTT

1977' AATGGGCCCAAGGCCAACAGGCATATGCCTCACTACTGCCTGGAGAAGGGAGAGATTCAG
      ************************************************************
1952" AATGGGCCCAAGGCCAACAGGCATATGCCTCACTACTGCCTGGAGAAGGGAGAGATTCAG

2037' GTCCTCCAGCAGCCTCCCTCACCCAGTATGTTTTACAGATTACGGGGGGACCGGGTGAGC
      ************************************************************
2012" GTCCTCCAGCAGCCTCCCTCACCCAGTATGTTTTACAGATTACGGGGGGACCGGGTGAGC

2097' CAGTGACCCCCTGCAGCCCCCAGCTTCAGGCCTCAGTGTCTGCCAGTCAAGCTTCACAGG
      ************* **********************************************
2072" CAGTGACCCCCTGTAGCCCCCAGCTTCAGGCCTCAGTGTCTGCCAGTCAAGCTTCACAGG

2157' CATTGTGATGGGGCAGCCTTGGGGAATATAAAATTTTGTGAAGACTTGG
      *************************************************
2132" CATTGTGATGGGGCAGCCTTGGGGAATATAAAATTTTGTGAAGACTTGG
```

Fig. 4 lane 1 Sf21/pVL1393 lane 2 Sf21/pVL1393-F2G4 lane 1 Sf21/pVL1393
lane 2 Sf21/pVL1393-F2G3 lane 1 Sf21/pVL1393 lane 2 Sf21/pVL1393-F2G7

SEQUENCE LISTING

```
<160> NUMBER OF SEQ ID NOS: 40

<210> SEQ ID NO 1
<211> LENGTH: 397
<212> TYPE: PRT
```

-continued

<213> ORGANISM: Homo sapiens

<400> SEQUENCE: 1

Met Ser Val Gly Arg Arg Arg Ile Lys Leu Leu Gly Ile Leu Met Met
1 5 10 15

Ala Asn Val Phe Ile Tyr Phe Ile Met Glu Val Ser Lys Ser Ser Ser
20 25 30

Gln Glu Lys Asn Gly Lys Gly Glu Val Ile Ile Pro Lys Glu Lys Phe
35 40 45

Trp Lys Ile Ser Thr Pro Pro Glu Ala Tyr Trp Asn Arg Glu Gln Glu
50 55 60

Lys Leu Asn Arg Gln Tyr Asn Pro Ile Leu Ser Met Leu Thr Asn Gln
65 70 75 80

Thr Gly Glu Ala Gly Arg Leu Ser Asn Ile Ser His Leu Asn Tyr Cys
85 90 95

Glu Pro Asp Leu Arg Val Thr Ser Val Val Thr Gly Phe Asn Asn Leu
100 105 110

Pro Asp Arg Phe Lys Asp Phe Leu Leu Tyr Leu Arg Cys Arg Asn Tyr
115 120 125

Ser Leu Leu Ile Asp Gln Pro Asp Lys Cys Ala Lys Lys Pro Phe Leu
130 135 140

Leu Leu Ala Ile Lys Ser Leu Thr Pro His Phe Ala Arg Arg Gln Ala
145 150 155 160

Ile Arg Glu Ser Trp Gly Gln Glu Ser Asn Ala Gly Asn Gln Thr Val
165 170 175

Val Arg Val Phe Leu Leu Gly Gln Thr Pro Pro Glu Asp Asn His Pro
180 185 190

Asp Leu Ser Asp Met Leu Lys Phe Glu Ser Glu Lys His Gln Asp Ile
195 200 205

Leu Met Trp Asn Tyr Arg Asp Thr Phe Phe Asn Leu Ser Leu Lys Glu
210 215 220

Val Leu Phe Leu Arg Trp Val Ser Thr Ser Cys Pro Asp Thr Glu Phe
225 230 235 240

Val Phe Lys Gly Asp Asp Asp Val Phe Val Asn Thr His His Ile Leu
245 250 255

Asn Tyr Leu Asn Ser Leu Ser Lys Thr Lys Ala Lys Asp Leu Phe Ile
260 265 270

Gly Asp Val Ile His Asn Ala Gly Pro His Arg Asp Lys Lys Leu Lys
275 280 285

Tyr Tyr Ile Pro Glu Val Val Tyr Ser Gly Leu Tyr Pro Pro Tyr Ala
290 295 300

Gly Gly Gly Gly Phe Leu Tyr Ser Gly His Leu Ala Leu Arg Leu Tyr
305 310 315 320

His Ile Thr Asp Gln Val His Leu Tyr Pro Ile Asp Asp Val Tyr Thr
325 330 335

Gly Met Cys Leu Gln Lys Leu Gly Leu Val Pro Glu Lys His Lys Gly
340 345 350

Phe Arg Thr Phe Asp Ile Glu Glu Lys Asn Lys Asn Asn Ile Cys Ser
355 360 365

Tyr Val Asp Leu Met Leu Val His Ser Arg Lys Pro Gln Glu Met Ile
370 375 380

Asp Ile Trp Ser Gln Leu Gln Ser Ala His Leu Lys Cys
385 390 395

<210> SEQ ID NO 2
<211> LENGTH: 372
<212> TYPE: PRT
<213> ORGANISM: Homo sapiens

<400> SEQUENCE: 2

```
Met Lys Tyr Leu Arg His Arg Arg Pro Asn Ala Thr Leu Ile Leu Ala
  1               5                  10                  15

Ile Gly Ala Phe Thr Leu Leu Leu Phe Ser Leu Leu Val Ser Pro Pro
             20                  25                  30

Thr Cys Lys Val Gln Glu Gln Pro Pro Ala Ile Pro Glu Ala Leu Ala
         35                  40                  45

Trp Pro Thr Pro Pro Thr Arg Pro Ala Pro Ala Pro Cys His Ala Asn
     50                  55                  60

Thr Ser Met Val Thr His Pro Asp Phe Ala Thr Gln Pro Gln His Val
 65                  70                  75                  80

Gln Asn Phe Leu Leu Tyr Arg His Cys Arg His Phe Pro Leu Leu Gln
                 85                  90                  95

Asp Val Pro Pro Ser Lys Cys Ala Gln Pro Val Phe Leu Leu Leu Val
            100                 105                 110

Ile Lys Ser Ser Pro Ser Asn Tyr Val Arg Arg Glu Leu Leu Arg Arg
        115                 120                 125

Thr Trp Gly Arg Glu Arg Lys Val Arg Gly Leu Gln Leu Arg Leu Leu
    130                 135                 140

Phe Leu Val Gly Thr Ala Ser Asn Pro His Glu Ala Arg Lys Val Asn
145                 150                 155                 160

Arg Leu Leu Glu Leu Glu Ala Gln Thr His Gly Asp Ile Leu Gln Trp
                165                 170                 175

Asp Phe His Asp Ser Phe Phe Asn Leu Thr Leu Lys Gln Val Leu Phe
            180                 185                 190

Leu Gln Trp Gln Glu Thr Arg Cys Ala Asn Ala Ser Phe Val Leu Asn
        195                 200                 205

Gly Asp Asp Asp Val Phe Ala His Thr Asp Asn Met Val Phe Tyr Leu
    210                 215                 220

Gln Asp His Asp Pro Gly Arg His Leu Phe Val Gly Gln Leu Ile Gln
225                 230                 235                 240

Asn Val Gly Pro Ile Arg Ala Phe Trp Ser Lys Tyr Tyr Val Pro Glu
                245                 250                 255

Val Val Thr Gln Asn Glu Arg Tyr Pro Pro Tyr Cys Gly Gly Gly Gly
            260                 265                 270

Phe Leu Leu Ser Arg Phe Thr Ala Ala Ala Leu Arg Arg Ala Ala His
        275                 280                 285

Val Leu Asp Ile Phe Pro Ile Asp Asp Val Phe Leu Gly Met Cys Leu
    290                 295                 300

Glu Leu Glu Gly Leu Lys Pro Ala Ser His Ser Gly Ile Arg Thr Ser
305                 310                 315                 320

Gly Val Arg Ala Pro Ser Gln His Leu Ser Ser Phe Asp Pro Cys Phe
                325                 330                 335

Tyr Arg Asp Leu Leu Leu Val His Arg Phe Leu Pro Tyr Glu Met Leu
            340                 345                 350

Leu Met Trp Asp Ala Leu Asn Gln Pro Asn Leu Thr Cys Gly Asn Gln
        355                 360                 365

Thr Gln Ile Tyr
    370
```

<210> SEQ ID NO 3
<211> LENGTH: 372
<212> TYPE: PRT
<213> ORGANISM: Homo sapiens

<400> SEQUENCE: 3

```
Met Lys Tyr Leu Arg His Arg Arg Pro Asn Ala Thr Leu Ile Leu Ala
  1               5                  10                  15

Ile Gly Ala Phe Thr Leu Leu Leu Phe Ser Leu Leu Val Ser Pro Pro
             20                  25                  30

Thr Cys Lys Val Gln Glu Gln Pro Pro Ala Ile Pro Glu Ala Leu Ala
         35                  40                  45

Trp Pro Thr Pro Pro Thr Arg Pro Ala Pro Ala Pro Cys His Ala Asn
     50                  55                  60

Thr Ser Met Val Thr His Pro Asp Phe Ala Thr Gln Pro Gln His Val
 65                  70                  75                  80

Gln Asn Phe Leu Leu Tyr Arg His Cys Arg His Phe Pro Leu Leu Gln
                 85                  90                  95

Asp Val Pro Pro Ser Lys Cys Ala Gln Pro Val Phe Leu Leu Leu Val
            100                 105                 110

Ile Lys Ser Ser Pro Ser Asn Tyr Val Arg Arg Glu Leu Leu Arg Arg
        115                 120                 125

Thr Trp Gly Arg Glu Arg Lys Val Arg Gly Leu Gln Leu Arg Leu Leu
    130                 135                 140

Phe Leu Val Gly Thr Ala Ser Asn Pro His Glu Ala Arg Lys Val Asn
145                 150                 155                 160

Arg Leu Leu Glu Leu Glu Ala Gln Thr His Gly Asp Ile Leu Gln Trp
                165                 170                 175

Asp Phe His Asp Ser Phe Phe Asn Leu Thr Leu Lys Gln Val Leu Phe
            180                 185                 190

Leu Gln Trp Gln Glu Thr Arg Cys Ala Asn Ala Ser Phe Val Leu Asn
        195                 200                 205

Gly Asp Asp Asp Val Phe Ala His Thr Asp Asn Met Val Phe Tyr Leu
    210                 215                 220

Gln Asp His Asp Pro Gly Arg His Leu Phe Val Gly Gln Leu Ile Gln
225                 230                 235                 240

Asn Val Gly Pro Ile Arg Ala Phe Trp Ser Lys Tyr Tyr Val Pro Glu
                245                 250                 255

Val Val Thr Gln Asn Glu Arg Tyr Pro Pro Tyr Cys Gly Gly Gly Gly
            260                 265                 270

Phe Leu Leu Ser Arg Phe Thr Ala Ala Ala Leu Arg Arg Ala Ala His
        275                 280                 285

Val Leu Asp Ile Phe Pro Ile Asp Asp Val Phe Leu Gly Met Cys Leu
    290                 295                 300

Glu Leu Glu Gly Leu Lys Pro Ala Ser His Ser Gly Ile Arg Thr Ser
305                 310                 315                 320

Gly Val Arg Ala Pro Ser Gln Arg Leu Ser Ser Phe Asp Pro Cys Phe
                325                 330                 335

Tyr Arg Asp Leu Leu Leu Val His Arg Phe Leu Pro Tyr Glu Met Leu
            340                 345                 350

Leu Met Trp Asp Ala Leu Asn Gln Pro Asn Leu Thr Cys Gly Asn Gln
        355                 360                 365

Thr Gln Ile Tyr
    370
```

<210> SEQ ID NO 4
<211> LENGTH: 378
<212> TYPE: PRT
<213> ORGANISM: Homo sapiens

<400> SEQUENCE: 4

```
Met Leu Pro Pro Gln Pro Ser Ala Ala His Gln Gly Arg Gly Gly Arg
  1               5                  10                  15

Ser Gly Leu Leu Pro Lys Gly Pro Ala Met Leu Cys Arg Leu Cys Trp
             20                  25                  30

Leu Val Ser Tyr Ser Leu Ala Val Leu Leu Leu Gly Cys Leu Leu Phe
         35                  40                  45

Leu Arg Lys Ala Ala Lys Pro Ala Gly Asp Pro Thr Ala His Gln Pro
     50                  55                  60

Phe Trp Ala Pro Pro Thr Pro Arg His Ser Arg Cys Pro Pro Asn His
 65                  70                  75                  80

Thr Val Ser Ser Ala Ser Leu Ser Leu Pro Ser Arg His Arg Leu Phe
                 85                  90                  95

Leu Thr Tyr Arg His Cys Arg Asn Phe Ser Ile Leu Leu Glu Pro Ser
            100                 105                 110

Gly Cys Ser Lys Asp Thr Phe Leu Leu Leu Ala Ile Lys Ser Gln Pro
        115                 120                 125

Gly His Val Glu Arg Arg Ala Ala Ile Arg Ser Thr Trp Gly Arg Val
    130                 135                 140

Gly Gly Trp Ala Arg Gly Arg Gln Leu Lys Leu Val Phe Leu Leu Gly
145                 150                 155                 160

Val Ala Gly Ser Ala Pro Pro Ala Gln Leu Leu Ala Tyr Glu Ser Arg
                165                 170                 175

Glu Phe Asp Asp Ile Leu Gln Trp Asp Phe Thr Glu Asp Phe Phe Asn
            180                 185                 190

Leu Thr Leu Lys Glu Leu His Leu Gln Arg Trp Val Val Ala Ala Cys
        195                 200                 205

Pro Gln Ala His Phe Met Leu Lys Gly Asp Asp Asp Val Phe Val His
    210                 215                 220

Val Pro Asn Val Leu Glu Phe Leu Asp Gly Trp Asp Pro Ala Gln Asp
225                 230                 235                 240

Leu Leu Val Gly Asp Val Ile Arg Gln Ala Leu Pro Asn Arg Asn Thr
                245                 250                 255

Lys Val Lys Tyr Phe Ile Pro Pro Ser Met Tyr Arg Ala Thr His Tyr
            260                 265                 270

Pro Pro Tyr Ala Gly Gly Gly Gly Tyr Val Met Ser Arg Ala Thr Val
        275                 280                 285

Arg Arg Leu Gln Ala Ile Met Glu Asp Ala Glu Leu Phe Pro Ile Asp
    290                 295                 300

Asp Val Phe Val Gly Met Cys Leu Arg Arg Leu Gly Leu Ser Pro Met
305                 310                 315                 320

His His Ala Gly Phe Lys Thr Phe Gly Ile Arg Arg Pro Leu Asp Pro
                325                 330                 335

Leu Asp Pro Cys Leu Tyr Arg Gly Leu Leu Leu Val His Arg Leu Ser
            340                 345                 350

Pro Leu Glu Met Trp Thr Met Trp Ala Leu Val Thr Asp Glu Gly Leu
        355                 360                 365

Lys Cys Ala Ala Gly Pro Ile Pro Gln Arg
    370                 375
```

```
<210> SEQ ID NO 5
<211> LENGTH: 1912
<212> TYPE: DNA
<213> ORGANISM: Homo sapiens

<400> SEQUENCE: 5

ggcgccggca gcgtcagcag cggcaacaag tgccggagta gcagagccaa gccggagcag      60

tccctgccgc cgacaccgcc gggccgcccg tccggggcgc cgcgcatgga gcgtgagctg     120

cggcggtcgc cgggctgagc cgcgcggagc gccgggacgt ggatgtggcc gcgatctccc     180

gcccttgccc ccgccccgcc gagctggagc tgctcccgga caagatatga gaa atg       236
                                                           Met
                                                             1

agt gtt gga cgt cga aga ata aag ttg ttg ggt atc ctg atg atg gca       284
Ser Val Gly Arg Arg Arg Ile Lys Leu Leu Gly Ile Leu Met Met Ala
            5                  10                  15

aat gtc ttc att tat ttt att atg gaa gtc tcc aaa agc agt agc caa       332
Asn Val Phe Ile Tyr Phe Ile Met Glu Val Ser Lys Ser Ser Ser Gln
        20                  25                  30

gaa aaa aat gga aaa ggg gaa gta ata ata ccc aaa gag aag ttc tgg       380
Glu Lys Asn Gly Lys Gly Glu Val Ile Ile Pro Lys Glu Lys Phe Trp
    35                  40                  45

aag ata tct acc cct ccc gag gca tac tgg aac cga gag caa gag aag       428
Lys Ile Ser Thr Pro Pro Glu Ala Tyr Trp Asn Arg Glu Gln Glu Lys
 50                  55                  60                  65

ctg aac cgg cag tac aac ccc atc ctg agc atg ctg acc aac cag acg       476
Leu Asn Arg Gln Tyr Asn Pro Ile Leu Ser Met Leu Thr Asn Gln Thr
                 70                  75                  80

ggg gag gcg ggc agg ctc tcc aat ata agc cat ctg aac tac tgc gaa       524
Gly Glu Ala Gly Arg Leu Ser Asn Ile Ser His Leu Asn Tyr Cys Glu
            85                  90                  95

cct gac ctg agg gtc acg tcg gtg gtt acg ggt ttt aac aac ttg ccg       572
Pro Asp Leu Arg Val Thr Ser Val Val Thr Gly Phe Asn Asn Leu Pro
        100                 105                 110

gac aga ttt aaa gac ttt ctg ctg tat ttg aga tgc cgc aat tat tca       620
Asp Arg Phe Lys Asp Phe Leu Leu Tyr Leu Arg Cys Arg Asn Tyr Ser
    115                 120                 125

ctg ctt ata gat cag ccg gat aag tgt gca aag aaa cct ttc ttg ttg       668
Leu Leu Ile Asp Gln Pro Asp Lys Cys Ala Lys Lys Pro Phe Leu Leu
130                 135                 140                 145

ctg gcg att aag tcc ctc act cca cat ttt gcc aga agg caa gca atc       716
Leu Ala Ile Lys Ser Leu Thr Pro His Phe Ala Arg Arg Gln Ala Ile
                150                 155                 160

cgg gaa tcc tgg ggc caa gaa agc aac gca ggg aac caa acg gtg gtg       764
Arg Glu Ser Trp Gly Gln Glu Ser Asn Ala Gly Asn Gln Thr Val Val
            165                 170                 175

cga gtc ttc ctg ctg ggc cag aca ccc cca gag gac aac cac ccc gac       812
Arg Val Phe Leu Leu Gly Gln Thr Pro Pro Glu Asp Asn His Pro Asp
        180                 185                 190

ctt tca gat atg ctg aaa ttt gag agt gag aag cac caa gac att ctt       860
Leu Ser Asp Met Leu Lys Phe Glu Ser Glu Lys His Gln Asp Ile Leu
    195                 200                 205

atg tgg aac tac aga gac act ttc ttc aac ttg tct ctg aag gaa gtg       908
Met Trp Asn Tyr Arg Asp Thr Phe Phe Asn Leu Ser Leu Lys Glu Val
210                 215                 220                 225

ctg ttt ctc agg tgg gta agt act tcc tgc cca gac act gag ttt gtt       956
Leu Phe Leu Arg Trp Val Ser Thr Ser Cys Pro Asp Thr Glu Phe Val
                230                 235                 240

ttc aag ggc gat gac gat gtt ttt gtg aac acc cat cac atc ctg aat      1004
Phe Lys Gly Asp Asp Asp Val Phe Val Asn Thr His His Ile Leu Asn
            245                 250                 255
```

-continued

```
tac ttg aat agt tta tcc aag acc aaa gcc aaa gat ctc ttc ata ggt     1052
Tyr Leu Asn Ser Leu Ser Lys Thr Lys Ala Lys Asp Leu Phe Ile Gly
        260                 265                 270

gat gtg atc cac aat gct gga cct cat cgg gat aag aag ctg aag tac     1100
Asp Val Ile His Asn Ala Gly Pro His Arg Asp Lys Lys Leu Lys Tyr
    275                 280                 285

tac atc cca gaa gtt gtt tac tct ggc ctc tac cca ccc tat gca ggg     1148
Tyr Ile Pro Glu Val Val Tyr Ser Gly Leu Tyr Pro Pro Tyr Ala Gly
290                 295                 300                 305

gga ggg ggg ttc ctc tac tcc ggc cac ctg gcc ctg agg ctg tac cat     1196
Gly Gly Gly Phe Leu Tyr Ser Gly His Leu Ala Leu Arg Leu Tyr His
                310                 315                 320

atc act gac cag gtc cat ctc tac ccc att gat gac gtt tat act gga     1244
Ile Thr Asp Gln Val His Leu Tyr Pro Ile Asp Asp Val Tyr Thr Gly
            325                 330                 335

atg tgc ctt cag aaa ctc ggc ctc gtt cca gag aaa cac aaa ggc ttc     1292
Met Cys Leu Gln Lys Leu Gly Leu Val Pro Glu Lys His Lys Gly Phe
        340                 345                 350

agg aca ttt gat atc gag gag aaa aac aaa aat aac atc tgc tcc tat     1340
Arg Thr Phe Asp Ile Glu Glu Lys Asn Lys Asn Asn Ile Cys Ser Tyr
    355                 360                 365

gta gat ctg atg tta gta cat agt aga aaa cct caa gag atg att gat     1388
Val Asp Leu Met Leu Val His Ser Arg Lys Pro Gln Glu Met Ile Asp
370                 375                 380                 385

att tgg tct cag ttg cag agt gct cat tta aaa tgc taaaatagat          1434
Ile Trp Ser Gln Leu Gln Ser Ala His Leu Lys Cys
                390                 395

acaaactcaa ttttgcatag aaaggtgtat tttgaatagt tcccatgttg tgttctcaca   1494

ttagagtaat ttctatatta aaccatgaaa attgccttta tgagtgatac ccatttgagg   1554

gcctctaaac ccttcaattt ggtactcacg tgaagaggga aagcggaaga tggtaatttt   1614

tttttatgga tgatatggca ggatgattgg ttctgatctt accggctagt ggtcattttt   1674

aaaaaacttg taccctctta tctgaaatcc tgtttctgga atttggccat tttaagtgat   1734

tttgtttgcc ctcttctata atattcctac ttcccataat aatgactgat ttatttgtta   1794

ttcaggtatt tataaaccta ttggctacaa agactttgtt aaactttatc cagtggtttt   1854

cgtgaaatgg aattatgttt atttttatgg gatttgggta aattttaaat tgtctaga     1912


<210> SEQ ID NO 6
<211> LENGTH: 2205
<212> TYPE: DNA
<213> ORGANISM: Homo sapiens

<400> SEQUENCE: 6

ggccaggaac ccgcaaggcg ctgcttgttc atctccagcc acggggagct cattccctag     60

cagcgggcca gacccaagga gccgcccagg aggctcctca ggccgacccc agaccctggc    120

tggccagg atg aag tat ctc cgg cac cgg cgg ccc aat gcc acc ctc att     170
         Met Lys Tyr Leu Arg His Arg Arg Pro Asn Ala Thr Leu Ile
           1               5                  10

ctg gcc atc ggc gct ttc acc ctc ctc ctc ttc agt ctg cta gtg tca      218
Leu Ala Ile Gly Ala Phe Thr Leu Leu Leu Phe Ser Leu Leu Val Ser
 15                  20                  25                  30

cca ccc acc tgc aag gtc cag gag cag cca ccg gcg atc ccc gag gcc      266
Pro Pro Thr Cys Lys Val Gln Glu Gln Pro Pro Ala Ile Pro Glu Ala
                 35                  40                  45

ctg gcc tgg ccc act cca ccc acc cgc cca gcc ccg gcc ccg tgc cat      314
Leu Ala Trp Pro Thr Pro Pro Thr Arg Pro Ala Pro Ala Pro Cys His
             50                  55                  60
```

-continued gcc aac acc tct atg gtc acc cac ccg gac ttc gcc acg cag ccg cag 362
Ala Asn Thr Ser Met Val Thr His Pro Asp Phe Ala Thr Gln Pro Gln
65 70 75 cac gtt cag aac ttc ctc ctg tac aga cac tgc cgc cac ttt ccc ctg 410
His Val Gln Asn Phe Leu Leu Tyr Arg His Cys Arg His Phe Pro Leu
80 85 90 ctg cag gac gtg ccc ccc tct aag tgc gcg cag ccg gtc ttc ctg ctg 458
Leu Gln Asp Val Pro Pro Ser Lys Cys Ala Gln Pro Val Phe Leu Leu
95 100 105 110 ctg gtg atc aag tcc tcc cct agc aac tat gtg cgc cgc gag ctg ctg 506
Leu Val Ile Lys Ser Ser Pro Ser Asn Tyr Val Arg Arg Glu Leu Leu
115 120 125 cgg cgc acg tgg ggc cgc gag cgc aag gta cgg ggt ttg cag ctg cgc 554
Arg Arg Thr Trp Gly Arg Glu Arg Lys Val Arg Gly Leu Gln Leu Arg
130 135 140 ctc ctc ttc ctg gtg ggc aca gcc tcc aac ccg cac gag gcc cgc aag 602
Leu Leu Phe Leu Val Gly Thr Ala Ser Asn Pro His Glu Ala Arg Lys
145 150 155 gtc aac cgg ctg ctg gag ctg gag gca cag act cac gga gac atc ctg 650
Val Asn Arg Leu Leu Glu Leu Glu Ala Gln Thr His Gly Asp Ile Leu
160 165 170 cag tgg gac ttc cac gac tcc ttc ttc aac ctc acg ctc aag cag gtc 698
Gln Trp Asp Phe His Asp Ser Phe Phe Asn Leu Thr Leu Lys Gln Val
175 180 185 190 ctg ttc tta cag tgg cag gag aca agg tgc gcc aac gcc agc ttc gtg 746
Leu Phe Leu Gln Trp Gln Glu Thr Arg Cys Ala Asn Ala Ser Phe Val
195 200 205 ctc aac ggg gat gat gac gtc ttt gca cac aca gac aac atg gtc ttc 794
Leu Asn Gly Asp Asp Asp Val Phe Ala His Thr Asp Asn Met Val Phe
210 215 220 tac ctg cag gac cat gac cct ggc cgc cac ctc ttc gtg ggg caa ctg 842
Tyr Leu Gln Asp His Asp Pro Gly Arg His Leu Phe Val Gly Gln Leu
225 230 235 atc caa aac gtg ggc ccc atc cgg gct ttt tgg agc aag tac tat gtg 890
Ile Gln Asn Val Gly Pro Ile Arg Ala Phe Trp Ser Lys Tyr Tyr Val
240 245 250 cca gag gtg gtg act cag aat gag cgg tac cca ccc tat tgt ggg ggt 938
Pro Glu Val Val Thr Gln Asn Glu Arg Tyr Pro Pro Tyr Cys Gly Gly
255 260 265 270 ggt ggc ttc ttg ctg tcc cgc ttc acg gcc gct gcc ctg cgc cgt gct 986
Gly Gly Phe Leu Leu Ser Arg Phe Thr Ala Ala Ala Leu Arg Arg Ala
275 280 285 gcc cat gtc ttg gac atc ttc ccc att gat gat gtc ttc ctg ggt atg 1034
Ala His Val Leu Asp Ile Phe Pro Ile Asp Asp Val Phe Leu Gly Met
290 295 300 tgt ctg gag ctt gag gga ctg aag cct gcc tcc cac agc ggc atc cgc 1082
Cys Leu Glu Leu Glu Gly Leu Lys Pro Ala Ser His Ser Gly Ile Arg
305 310 315 acg tct ggc gtg cgg gct cca tcg caa cac ctg tcc tcc ttt gac ccc 1130
Thr Ser Gly Val Arg Ala Pro Ser Gln His Leu Ser Ser Phe Asp Pro
320 325 330 tgc ttc tac cga gac ctg ctg ctg gtg cac cgc ttc cta cct tat gag 1178
Cys Phe Tyr Arg Asp Leu Leu Leu Val His Arg Phe Leu Pro Tyr Glu
335 340 345 350 atg ctg ctc atg tgg gat gcg ctg aac cag ccc aac ctc acc tgc ggc 1226
Met Leu Leu Met Trp Asp Ala Leu Asn Gln Pro Asn Leu Thr Cys Gly
355 360 365 aat cag aca cag atc tac tgagtcagca tcagggtccc cagcctctgg 1274
Asn Gln Thr Gln Ile Tyr
370

-continued

```
gctcctgttt ccagaggaag gggcgacacc ttcctcccag gaagctgaga cctttgtggt   1334

ctgagcataa gggagtgcca gggaaggttt gaggtttgat gagtgaatat tctggctggc   1394

gaactcctac acatccttca aaacccacct ggtactgttc cagcatcttc cctggatggc   1454

tggaggaact ccagaaaata tgcatcttct ttttgtggct gctaatggca gaagtgcctg   1514

tgctagagtt ccaactgtgg atgcatccgt cccgtttgag tcaaagtctt acttccctgc   1574

tctcacctac tcacagacgg gatgctaagc agtgcacctg cagtggttta atggcagata   1634

agctccgtct gcagttccag gccagccaga aactcctgtg tccacataga gctgacgtga   1694

gaaatatctt tcagcccagg agagaggggt cctgatctta accctttcct gggtctcaga   1754

caactcagaa ggttgggggg ataccagaga ggtggtggaa taggaccgcc ccctccttac   1814

ttgtgggatc aaatgctgta atggtggagg tgtgggcaga ggagggaggc aagtgtcttt   1874

gaaagttgtg agagctcaga gtttctgggg tcctcattag gagcccccat ccctgtgttc   1934

cccaagaatt cagagaacag cactggggct ggaatgatct ttaatgggcc caaggccaac   1994

aggcatatgc ctcactactg cctggagaag ggagagattc aggtcctcca gcagcctccc   2054

tcacccagta tgttttacag attacggggg gaccgggtga gccagtgacc ccctgcagcc   2114

cccagcttca ggcctcagtg tctgccagtc aagcttcaca ggcattgtga tggggcagcc   2174

ttggggaata taaaattttg tgaagacttg g                                  2205


<210> SEQ ID NO 7
<211> LENGTH: 2180
<212> TYPE: DNA
<213> ORGANISM: Homo sapiens

<400> SEQUENCE: 7

cgcgagctga gaggagcagg tagaggggca gaggcgggac tgtcgtctgg gggagccgcc     60

caggaggctc ctcaggccga ccccagaccc tggctggcca gg atg aag tat ctc       114
                                               Met Lys Tyr Leu
                                                 1

cgg cac cgg cgg ccc aat gcc acc ctc att ctg gcc atc ggc gct ttc      162
Arg His Arg Arg Pro Asn Ala Thr Leu Ile Leu Ala Ile Gly Ala Phe
  5                  10                  15                  20

acc ctc ctc ctc ttc agt ctg cta gtg tca cca ccc acc tgc aag gtc      210
Thr Leu Leu Leu Phe Ser Leu Leu Val Ser Pro Pro Thr Cys Lys Val
                 25                  30                  35

cag gag cag cca ccg gcg atc ccc gag gcc ctg gcc tgg ccc act cca      258
Gln Glu Gln Pro Pro Ala Ile Pro Glu Ala Leu Ala Trp Pro Thr Pro
             40                  45                  50

ccc acc cgc cca gcc ccg gcc ccg tgc cat gcc aac acc tct atg gtc      306
Pro Thr Arg Pro Ala Pro Ala Pro Cys His Ala Asn Thr Ser Met Val
         55                  60                  65

acc cac ccg gac ttc gcc acg cag ccg cag cac gtt cag aac ttc ctc      354
Thr His Pro Asp Phe Ala Thr Gln Pro Gln His Val Gln Asn Phe Leu
     70                  75                  80

ctg tac aga cac tgc cgc cac ttt ccc ctg ctg cag gac gtg ccc ccc      402
Leu Tyr Arg His Cys Arg His Phe Pro Leu Leu Gln Asp Val Pro Pro
 85                  90                  95                 100

tct aag tgc gcg cag ccg gtc ttc ctg ctg ctg gtg atc aag tcc tcc      450
Ser Lys Cys Ala Gln Pro Val Phe Leu Leu Leu Val Ile Lys Ser Ser
                105                 110                 115

cct agc aac tat gtg cgc cgc gag ctg ctg cgg cgc acg tgg ggc cgc      498
Pro Ser Asn Tyr Val Arg Arg Glu Leu Leu Arg Arg Thr Trp Gly Arg
            120                 125                 130

gag cgc aag gta cgg ggt ttg cag ctg cgc ctc ctc ttc ctg gtg ggc      546
```

-continued

```
Glu Arg Lys Val Arg Gly Leu Gln Leu Arg Leu Leu Phe Leu Val Gly
        135                 140                 145

aca gcc tcc aac ccg cac gag gcc cgc aag gtc aac cgg ctg ctg gag      594
Thr Ala Ser Asn Pro His Glu Ala Arg Lys Val Asn Arg Leu Leu Glu
    150                 155                 160

ctg gag gca cag act cac gga gac atc ctg cag tgg gac ttc cac gac      642
Leu Glu Ala Gln Thr His Gly Asp Ile Leu Gln Trp Asp Phe His Asp
165                 170                 175                 180

tcc ttc ttc aac ctc acg ctc aag cag gtc ctg ttc tta cag tgg cag      690
Ser Phe Phe Asn Leu Thr Leu Lys Gln Val Leu Phe Leu Gln Trp Gln
                185                 190                 195

gag aca agg tgc gcc aac gcc agc ttc gtg ctc aac ggg gat gat gac      738
Glu Thr Arg Cys Ala Asn Ala Ser Phe Val Leu Asn Gly Asp Asp Asp
            200                 205                 210

gtc ttt gca cac aca gac aac atg gtc ttc tac ctg cag gac cat gac      786
Val Phe Ala His Thr Asp Asn Met Val Phe Tyr Leu Gln Asp His Asp
        215                 220                 225

cct ggc cgc cac ctc ttc gtg ggg caa ctg atc caa aac gtg ggc ccc      834
Pro Gly Arg His Leu Phe Val Gly Gln Leu Ile Gln Asn Val Gly Pro
    230                 235                 240

atc cgg gct ttt tgg agc aag tac tat gtg cca gag gtg gtg act cag      882
Ile Arg Ala Phe Trp Ser Lys Tyr Tyr Val Pro Glu Val Val Thr Gln
245                 250                 255                 260

aat gag cgg tac cca ccc tat tgt ggg ggt ggt ggc ttc ttg ctg tcc      930
Asn Glu Arg Tyr Pro Pro Tyr Cys Gly Gly Gly Gly Phe Leu Leu Ser
                265                 270                 275

cgc ttc acg gcc gct gcc ctg cgc cgt gct gcc cat gtc ttg gac atc      978
Arg Phe Thr Ala Ala Ala Leu Arg Arg Ala Ala His Val Leu Asp Ile
            280                 285                 290

ttc ccc att gat gat gtc ttc ctg ggt atg tgt ctg gag ctt gag gga     1026
Phe Pro Ile Asp Asp Val Phe Leu Gly Met Cys Leu Glu Leu Glu Gly
        295                 300                 305

ctg aag cct gcc tcc cac agc ggc atc cgc acg tct ggc gtg cgg gct     1074
Leu Lys Pro Ala Ser His Ser Gly Ile Arg Thr Ser Gly Val Arg Ala
    310                 315                 320

cca tcg caa cgc ctg tcc tcc ttt gac ccc tgc ttc tac cga gac ctg     1122
Pro Ser Gln Arg Leu Ser Ser Phe Asp Pro Cys Phe Tyr Arg Asp Leu
325                 330                 335                 340

ctg ctg gtg cac cgc ttc cta cct tat gag atg ctg ctc atg tgg gat     1170
Leu Leu Val His Arg Phe Leu Pro Tyr Glu Met Leu Leu Met Trp Asp
                345                 350                 355

gcg ctg aac cag ccc aac ctc acc tgc ggc aat cag aca cag atc tac     1218
Ala Leu Asn Gln Pro Asn Leu Thr Cys Gly Asn Gln Thr Gln Ile Tyr
            360                 365                 370

tgagtcagca tcagggtccc cagcctctgg gctcctgttt ccataggaag ggcgacacc    1278

ttcctcccag gaagctgaga cctttgtggt ctgagcataa gggagtgcca gggaaggttt   1338

gaggtttgat gagtgaatat tctggctggc gaactcctac acatccttca aaacccacct   1398

ggtactgttc cagcatcttc cctggatggc tggaggaact ccagaaaata tccatcttct   1458

ttttgtggct gctaatggca gaagtgcctg tgctagagtt ccaactgtgg atgcatccgt   1518

cccgtttgag tcaaagtctt acttccctgc tctcacctac tcacagacgg gatgctaagc   1578

agtgcacctg cagtggttta atggcagata agctccgtct gcagttccag gccagccaga   1638

aactcctgtg tccacataga gctgacgtga gaaatatctt tcagcccagg agagaggggt   1698

cctgatctta accctttcct gggtctcaga caactcagaa ggttgggggg ataccagaga   1758

ggtggtggaa taggaccgcc ccctccttac ttgtgggatc aaatgctgta atggtggagg   1818

tgtgggcaga ggagggaggc aagtgtcctt tgaaagttgt gagagctcag agtttctggg   1878
```

-continued

```
gtcctcatta ggagccccca tccctgtgtt ccccaagaat tcagagaaca gcactggggc   1938

tggaatgatc tttaatgggc ccaaggccaa caggcatatg cctcactact gcctggagaa   1998

gggagagatt caggtcctcc agcagcctcc ctcacccagt atgttttaca gattacgggg   2058

ggaccgggtg agccagtgac cccctgtagc ccccagcttc aggcctcagt gtctgccagt   2118

caagcttcac aggcattgtg atggggcagc cttggggaat ataaaatttt gtgaagactt   2178

gg                                                                  2180


<210> SEQ ID NO 8
<211> LENGTH: 1296
<212> TYPE: DNA
<213> ORGANISM: Homo sapiens

<400> SEQUENCE: 8

cacagcctga gactcatctc gcttcgaccc cgccgccgcc gccgccgccc ggcatcctga     60

gcacggagac agtctccagc tgccgttc atg ctt cct ccc cag cct tct gca       112
                               Met Leu Pro Pro Gln Pro Ser Ala
                                 1               5

gcc cac cag gga agg ggc ggt agg agt ggc ctt tta cca aag gga ccg      160
Ala His Gln Gly Arg Gly Gly Arg Ser Gly Leu Leu Pro Lys Gly Pro
     10                  15                  20

gcg atg ctc tgc agg ctg tgc tgg ctg gtc tcg tac agc ttg gct gtg      208
Ala Met Leu Cys Arg Leu Cys Trp Leu Val Ser Tyr Ser Leu Ala Val
 25                  30                  35                  40

ctg ttg ctc ggc tgc ctg ctc ttc ctg agg aag gcg gcc aag ccc gca      256
Leu Leu Leu Gly Cys Leu Leu Phe Leu Arg Lys Ala Ala Lys Pro Ala
                 45                  50                  55

gga gac ccc acg gcc cac cag cct ttc tgg gct ccc cca aca ccc cgt      304
Gly Asp Pro Thr Ala His Gln Pro Phe Trp Ala Pro Pro Thr Pro Arg
             60                  65                  70

cac agc cgg tgt cca ccc aac cac aca gtg tct agc gcc tct ctg tcc      352
His Ser Arg Cys Pro Pro Asn His Thr Val Ser Ser Ala Ser Leu Ser
         75                  80                  85

ctg cct agc cgt cac cgt ctc ttc ttg acc tat cgt cac tgc cga aat      400
Leu Pro Ser Arg His Arg Leu Phe Leu Thr Tyr Arg His Cys Arg Asn
     90                  95                 100

ttc tct atc ttg ctg gag cct tca ggc tgt tcc aag gat acc ttc ttg      448
Phe Ser Ile Leu Leu Glu Pro Ser Gly Cys Ser Lys Asp Thr Phe Leu
105                 110                 115                 120

ctc ctg gcc atc aag tca cag cct ggt cac gtg gag cga cgt gcg gct      496
Leu Leu Ala Ile Lys Ser Gln Pro Gly His Val Glu Arg Arg Ala Ala
                125                 130                 135

atc cgc agc acg tgg ggc agg gtg ggg gga tgg gct agg ggc cgg cag      544
Ile Arg Ser Thr Trp Gly Arg Val Gly Gly Trp Ala Arg Gly Arg Gln
            140                 145                 150

ctg aag ctg gtg ttc ctc cta ggg gtg gca gga tcc gct ccc cca gcc      592
Leu Lys Leu Val Phe Leu Leu Gly Val Ala Gly Ser Ala Pro Pro Ala
        155                 160                 165

cag ctg ctg gcc tat gag agt agg gag ttt gat gac atc ctc cag tgg      640
Gln Leu Leu Ala Tyr Glu Ser Arg Glu Phe Asp Asp Ile Leu Gln Trp
    170                 175                 180

gac ttc act gag gac ttc ttc aac ctg acg ctc aag gag ctg cac ctg      688
Asp Phe Thr Glu Asp Phe Phe Asn Leu Thr Leu Lys Glu Leu His Leu
185                 190                 195                 200

cag cgc tgg gtg gtg gct gcc tgc ccc cag gcc cat ttc atg cta aag      736
Gln Arg Trp Val Val Ala Ala Cys Pro Gln Ala His Phe Met Leu Lys
                205                 210                 215

gga gat gac gat gtc ttt gtc cac gtc ccc aac gtg tta gag ttc ctg      784
```

```
Gly Asp Asp Asp Val Phe Val His Val Pro Asn Val Leu Glu Phe Leu
            220                 225                 230

gat ggc tgg gac cca gcc cag gac ctc ctg gtg gga gat gtc atc cgc      832
Asp Gly Trp Asp Pro Ala Gln Asp Leu Leu Val Gly Asp Val Ile Arg
        235                 240                 245

caa gcc ctg ccc aac agg aac act aag gtc aaa tac ttc atc cca ccc      880
Gln Ala Leu Pro Asn Arg Asn Thr Lys Val Lys Tyr Phe Ile Pro Pro
    250                 255                 260

tca atg tac agg gcc acc cac tac cca ccc tat gct ggt ggg gga gga      928
Ser Met Tyr Arg Ala Thr His Tyr Pro Pro Tyr Ala Gly Gly Gly Gly
265                 270                 275                 280

tat gtc atg tcc aga gcc aca gtg cgg cgc ctc cag gct atc atg gaa      976
Tyr Val Met Ser Arg Ala Thr Val Arg Arg Leu Gln Ala Ile Met Glu
                285                 290                 295

gat gct gaa ctc ttc ccc att gat gat gtc ttt gtg ggt atg tgc ctg     1024
Asp Ala Glu Leu Phe Pro Ile Asp Asp Val Phe Val Gly Met Cys Leu
            300                 305                 310

agg agg ctg ggg ctg agc cct atg cac cat gct ggc ttc aag aca ttt     1072
Arg Arg Leu Gly Leu Ser Pro Met His His Ala Gly Phe Lys Thr Phe
        315                 320                 325

gga atc cgg cgg ccc ctg gac ccc tta gac ccc tgc ctg tat agg ggg     1120
Gly Ile Arg Arg Pro Leu Asp Pro Leu Asp Pro Cys Leu Tyr Arg Gly
    330                 335                 340

ctc ctg ctg gtt cac cgc ctc agc ccc ctc gag atg tgg acc atg tgg     1168
Leu Leu Leu Val His Arg Leu Ser Pro Leu Glu Met Trp Thr Met Trp
345                 350                 355                 360

gca ctg gtg aca gat gag ggg ctc aag tgt gca gct ggc ccc ata ccc     1216
Ala Leu Val Thr Asp Glu Gly Leu Lys Cys Ala Ala Gly Pro Ile Pro
                365                 370                 375

cag cgc tgaagggtgg gttgggcaac agcctgagag tggactcagt gttgattctc     1272
Gln Arg

tatcgtgatg cgaaattgat gcct                                          1296


<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 9

ccggacagat ttaaagactt tctgc                                           25


<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 10

gtagaggcca gagtaaacaa cttct                                           25


<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 11
```

cgtggggcaa ctgatccaaa acg 23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: synthetic
DNA

<400> SEQUENCE: 12
acccaggaag acatcatcaa tggg 24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: synthetic
DNA

<400> SEQUENCE: 13
cacagcctga gactcatctc gct 23

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: synthetic
DNA

<400> SEQUENCE: 14
aggcatcaat ttcgcatcac gatag 25

<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: synthetic
DNA

<400> SEQUENCE: 15
ctttagagca c 11

<210> SEQ ID NO 16
<211> LENGTH: 8
<212> TYPE: DNA
<213> ORGANISM: Artificial Sequence
<220> FEATURE:
<223> OTHER INFORMATION: Description of Artificial Sequence: synthetic
DNA

<400> SEQUENCE: 16 ctctaaag 8

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:commercially
available amino acid sequence

<400> SEQUENCE: 17

Asp Tyr Lys Asp Asp Asp Asp Lys 1 5

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: synthetic DNA

<400> SEQUENCE: 18
agcttgccgc caccatgcat tttcaagtgc agattttca 39

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: synthetic DNA

<400> SEQUENCE: 19
gcttcctgct aatcagtgcc tcagtcataa tgtcacgtg 39

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: synthetic DNA

<400> SEQUENCE: 20
gagattacaa ggacgacgat gacaaggcct acgtag 36

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: synthetic DNA

<400> SEQUENCE: 21
gaagctgaaa atctgcactt gaaaatgcat ggtggcggca 40

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: synthetic DNA

<400> SEQUENCE: 22
atctccacgt gacattatga ctgaggcact gattagcag 39

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: synthetic DNA

<400> SEQUENCE: 23
gtacctacgt aggccttgtc atcgtcgtcc ttgta 35

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: synthetic
DNA

<400> SEQUENCE: 24
cgcggatcct ccccacggtc cgtggaccag 30

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: synthetic
DNA

<400> SEQUENCE: 25
atagtttagc ggccgcggaa gggctcagca gcgtcg 36

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: synthetic
DNA

<400> SEQUENCE: 26
cgaggatccg agcagccacc ggcgatccc 29

<210> SEQ ID NO 27
<211> LENGTH: 41
<212> TYPE: DNA
<213> ORGANISM: Artificial Sequence
<220> FEATURE:
<223> OTHER INFORMATION: Description of Artificial Sequence: synthetic
DNA

<400> SEQUENCE: 27
gtcgctatgc ggccgctcag tagatctgtg tctgattgcc g 41

<210> SEQ ID NO 28
<211> LENGTH: 13
<212> TYPE: DNA
<213> ORGANISM: Artificial Sequence
<220> FEATURE:
<223> OTHER INFORMATION: Description of Artificial Sequence: synthetic
DNA

<400> SEQUENCE: 28
gatcatcgcg aga 13

<210> SEQ ID NO 29
<211> LENGTH: 13
<212> TYPE: DNA
<213> ORGANISM: Artificial Sequence
<220> FEATURE:
<223> OTHER INFORMATION: Description of Artificial Sequence: synthetic
DNA

<400> SEQUENCE: 29
agcttctcgc gat 13

<210> SEQ ID NO 30

<211> LENGTH: 24
<212> TYPE: DNA
<213> ORGANISM: Artificial Sequence
<220> FEATURE:
<223> OTHER INFORMATION: Description of Artificial Sequence: synthetic
DNA

<400> SEQUENCE: 30
gcccaacagg aacactaagg tcaa 24

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence:Synthetic
DNA

<400> SEQUENCE: 31
cacggatcca gccaagaaaa aaatggaaaa gggga 35

<210> SEQ ID NO 32
<211> LENGTH: 44
<212> TYPE: DNA
<213> ORGANISM: Artificial Sequence
<220> FEATURE:
<223> OTHER INFORMATION: Description of Artificial Sequence:Synthetic
DNA

<400> SEQUENCE: 32
atccgatagc ggccgcttag cattttaaat gagcactctg caac 44

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence:Synthetic
DNA

<400> SEQUENCE: 33
ataagatctg caggagaccc cacggcccac c 31

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence:Synthetic
DNA

<400> SEQUENCE: 34
atagttatgc ggccgcctca ggctgttgcc caacccac 38

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence:Synthetic
DNA

<400> SEQUENCE: 35
gagaagttct ggaagatatc tacc 24

<210> SEQ ID NO 36
<211> LENGTH: 24
<212> TYPE: DNA

-continued

<213> ORGANISM: Artificial Sequence
<220> FEATURE:
<223> OTHER INFORMATION: Description of Artificial Sequence:Synthetic DNA

<400> SEQUENCE: 36
ctattcaagt aattcaggat gtga 24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence:Synthetic DNA

<400> SEQUENCE: 37
gtgccatgcc aacacctcta tggt 24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence:Synthetic DNA

<400> SEQUENCE: 38
tcctgcaggt agaagaccat gttg 24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence:Synthetic DNA

<400> SEQUENCE: 39
gtctcttctt gacctatcgt cact 24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence:Synthetic DNA

<400> SEQUENCE: 40
agttcagcat cttccatgat agcc 24

METHODS FOR SYNTHESIZING SUGAR CHAINS USING β1,3-N-ACETYLGLUCOSAMINYLTRANSFERASE

This application is a division of application Ser. No. 12/019,793 filed Jan. 25, 2008, now U.S. Pat. No. 7,972,815, which in turn is a division of application Ser. No. 11/148,280 filed Jun. 9, 2005, now abandoned, which in turn is a division of application Ser. No. 10/019,735 filed Dec. 28, 2001, now U.S. Pat. No. 7,005,279, which in turn is an application filed under 35 U.S.C. §371 based upon International Application No. PCT/JP00/04304 filed Jun. 29, 2000, claiming priority to Japanese Application Nos. 183437/99 filed Jun. 29, 1999 and 2000-74757 filed Mar. 16, 2000.

TECHNICAL FIELD

The present invention relates to a novel polypeptide having a β1,3-N-acetylglucosaminyltransferase activity; a sugar chain synthesizing agent comprising the polypeptide as an active ingredient; a DNA which encodes the polypeptide; an agent for detecting inflammation, cancer or metastasis, comprising the DNA; a recombinant DNA which is obtained by inserting the DNA into a vector; a transformant carrying the recombinant DNA; a method for producing the polypeptide by using the transformant; a method for producing a sugar chain or complex carbohydrate by using the polypeptide; a process for producing a sugar chain or complex carbohydrate by using the transformant; a method for detecting inflammation, cancer or metastasis by using an oligonucleotide obtained from the DNA encoding the polypeptide; an antibody which recognizes the polypeptide; an immunohistostaining method by using the antibody; an immunohistostaining agent comprising the antibody; an agent for diagnosing inflammation, cancer or metastasis; a method for screening a compound capable of changing the β1,3-N-acetylglucosaminyltransferase activity of the polypeptide; a method for screening a compound capable of changing the expression of the corresponding gene; a promoter DNA capable of controlling the transcription of the corresponding gene; a method for screening a compound capable of changing the efficiency of transcription by the promoter DNA; a compound obtained by these screening methods; a knock out animal in which the corresponding gene is deleted or mutated; and the like.

BACKGROUND ART

It is considered that sugar chains are related to vital phenomena such as development, differentiation and cell recognition and also deeply related to the development and progress of inflammations, cancers, autoimmune diseases and a large number of other diseases [Fukuda, M., *Cell Surface Carbohydrates and Cell Development*, CRC Press, Bosa Raton, Fla. (1992), *Glycobiology,* 3, 97 (1993)].

Sugar chains are present not only as glycoproteins, proteoglycans or glycolipids by addition to proteins or lipids and but also as oligosaccharides.

Gal β1,3-N-acetylglucosaminyltransferase is an enzyme having an activity of transferring N-acetylglucosamine to galactose residues present at the non-reducing terminal of a sugar chain via a β1,3-linkage, and involved in the synthesis of a sugar chain having a GlcNAc β1-3Gal structure. Sugar chains having a GlcNAcβ1-3Gal structure are present in N-glycosylated sugar chains and O-glycosylated sugar chains of glycoproteins and also in neolacto-series and facto-series glycolipids, and in oligosaccharides.

With regard to a Gal β1,3-N-acetylglucosaminyltransferase, its partial purification has so far been reported [*J. Biol. Chem.,* 268, 27118 (1993), *J. Biol. Chem.,* 267, 2994 (1992), *J. Biol. Chem.,* 263, 12461 (1988), *Jpn. J. Med. Sci. Biol.,* 42, 77 (1989)]. Also, two types of Gal β1,3-N-acetylglucosaminyltransferase have been cloned [*Proc. Natl. Acad. Sci. USA.,* 94, 14294 (1997), *Proc. Natl. Acad. Sci. USA.,* 96, 406 (1999)]. The presence of other types of Gal β1,3-N-acetylglucosaminyltransferases has not been clarified.

Since sugar chains having a GlcNAcβ1-3Gal structure are present in great numbers, it is considered that two or more enzymes having different receptor substrate specificity or expressing at different tissue are present as Gal β1,3-N-acetylglucosaminyltransferases, and they are respectively taking part in different functions. Thus, it is an important subject to clone a Gal β1,3-N-acetylglucosaminyltransferase different from the two enzymes so far cloned, to examine its receptor substrate specificity as well as expression and distribution, and to elucidate its relation to biological functions and diseases.

It is known that lacto-N-neotetraose (Galβ1-4GlcNAβ1-3Galβ1-4Glc) and lacto-N-tetraose (Galβ1-3GlcNAβ1-3Galβ1-4Glc) or various oligosaccharides containing them as the core structure are present in human milk [*Acta Paediatrica,* 82, 903 (1993)]. It is considered that these oligosaccharides have a function of preventing babies from viral and microbial infections and a function of neutralizing toxins. Also, they have an activity of accelerating growth of *Bifidobacterium* that is a good enteric bacterium.

It will be markedly useful from the industrial point of view if these oligosaccharides contained in human milk or milk containing them can be efficiently produced. If a gene for a Gal β1,3-N-acetylglucosaminyltransferase involved in the synthesis of these oligosaccharides contained in human milk is obtained, these oligosaccharides would be efficiently synthesized, but such an enzyme has not been found.

Among a large number of sugar chains having a GlcNAcβ1-3Gal structure, particularly poly-N-acetyllactosamine sugar chains serve as core sugar chains of many functional sugar chains (selectin ligand sugar chains, microbial or viral receptor sugar chains, SSEA-1 sugar chains, cancer-related sugar chains and the like) and deeply relate to diseases, such as embryogenesis, cell differentiation or diseases such as inflammation, cancer and the like.

Since there is a possibility that Gal β1,3-N-acetylglucosaminyltransferases involved in the synthesis of poly-N-acetyllactosamine sugar chains functioning in respective cases are different, it is an important subject to clone a Gal β1,3-N-acetylglucosaminyltransferase which is different from the two enzymes so far cloned and to estimate functions of respective enzymes based on their receptor substrate specificity, expression distribution and the like.

The poly-N-acetyllactosamine sugar chain is synthesized by the alternate functions of a GlcNAc β1,4-N-galactosyltransferase activity and a Gal β1,3-N-acetylglucosaminyltransferase activity. Regarding β1,4-galactosyltransferases, genes for 4 enzymes (β4Gal-T1, β4Gal-T2, β4Gal-T3 and β4Gal-T4) have been cloned, and the receptor substrate specificity of each enzyme has been analyzed [*J. Biol. Chem.,* 272, 31979 (1997), *J. Biol. Chem.,* 273, 29331 (1997)].

Accordingly, a poly-N-acetyllactosamine sugar chain can be synthesized in vitro by using a GlcNAc β1,4-galactosyltransferase and a Gal β1,3-N-acetylglucosaminyltransferase. Also, a poly-N-acetyllactosamine sugar chain or a complex carbohydrate to which the sugar chain is added can be synthesized by co-expressing a GlcNAc β1,4-galactosyltransferase gene and a Gal β1,3-N-acetylglucosaminyltransferase gene in cells.

Since a GlcNAc β1,4-galactosyltransferase is expressed in almost all cells, poly-N-acetyllactosamine sugar chain or a sugar to which the sugar chain is added can be synthesized by expressing a Gal β1,3-N-acetylglucosaminyltransferase gene in cells.

It is known that a poly-N-acetyllactosamine sugar chain is more frequently expressed in cancer cells in comparison with corresponding normal cells [*J. Biol. Chem.,* 259, 10834 (1984), *J. Biol. Chem.,* 261, 10772 (1986), *J. Biol. Chem.,* 266, 1772 (1991), *J. Biol. Chem.,* 267, 5700 (1992)].

It is expected that a poly-N-acetyllactosamine sugar chain having sialyl Lewis x sugar chain might be a medicament having an anti-inflammatory effect or a metastasis inhibiting effect, as a selectin antagonist.

A partially purified β1,3-N-acetylglucosaminyltransferase has been used in synthesizing the poly-N-acetyllactosamine sugar chain moiety of these oligosaccharides. But since supply of this enzyme is a rate-limiting step, it is difficult to synthesize the poly-N-acetyllactosamine sugar chain in a large amount [*Glycobiology,* 7, 453 (1997)].

On the other hand, a poly-N-acetyllactosamine sugar chain can also be synthesized by chemical synthesis, but its synthesis requires considerably complex steps [*Tetrahedron Letter,* 24, 5223 (1997)].

Thus, an efficient process for synthesizing a poly-N-acetyllactosamine sugar chain is in demand. Although two types of Gal β1,3-N-acetylglucosaminyltransferase so far cloned and genes for these enzymes can be used, it is considered that the use of other Gal β1,3-N-acetylglucosaminyltransferases having different substrate specificity and different function or their genes may be efficient in some cases depending on the purpose.

Since a poly-N-acetyllactosamine sugar chain contributes to the stabilization of protein [*J. Biol. Chem.,* 265, 20476 (1990)], it is considered that a protein can be stabilized by artificially adding a poly-N-acetyllactosamine sugar chain to a desired protein. Also, since a clearance rate of proteins in blood from the kidney becomes slower as the effective molecular weight of the protein becomes larger, it is considered that the clearance rate from the kidney can be reduced and blood stability can be increased by artificially adding a poly-N-acetyllactosamine sugar chain to a desired protein to thereby increase the size of the effective molecular weight. In addition, there is a possibility that a desired protein can be targeted to a specified cell. Cases in which synthesizing ability of a poly-N-acetyllactosamine sugar chain has been increased are shown below.

It is shown that a poly-N-acetyllactosamine sugar chain is added to sugar chains of a membrane-bound glycoprotein of cells when F9 cell is treated with retinoic acid or Swiss 3T3 cell is treated with TGF-β [*J. Biol. Chem.,* 268, 1242 (1993), *Biochim. Biophys. Acta.,* 1221, 330 (1994)].

It is shown that, when N-ras proto-oncogene is expressed in NIH3T3 cell, activities of β1,4-galactosyltransferase and β1,3-N-acetylglucosaminyltransferase which are involved in the synthesis of poly-N-acetyllactosamine sugar chains are increased and the amount of poly-N-acetyllactosamine sugar chains in the N-linked sugar chain of a membrane protein is increased [*J. Biol. Chem.,* 266, 21674 (1991)].

When the gene for core 2 β1,6-N-acetylglucosaminyltransferase is expressed in T-cell line EL-4, the molecular weight of a cell surface membrane protein CD43, CD45 or CD44 is increased [*J. Biol. Chem.,* 271, 18732 (1996)]. The phenomenon is considered to be due to that the sugar chain synthesized by the core 2 β1,6-N-acetylglucosaminyltransferase becomes a good substrate of a β1,3-N-acetylglucosaminyltransferase which is involved in the synthesis of a oly-N-acetyllactosamine sugar chain.

Also, it is known that when HL-60 cell is cultured at 27° C., the amount of poly-N-acetyllactosamine sugar chains added to lamp-1 or lamp-2 is increased [*J. Biol. Chem.,* 266, 23185 (1991)].

However, there are no reports on the efficient production of recombinant glycoproteins to which a poly-N-acetyllactosamine sugar chain is added, in host cells suitable for the production of recombinant glycoproteins (e.g., Namalwa cell, Namalwa KJM-1 cell, CHO cell and the like). Accordingly, development of a process for producing a recombinant glycoprotein to which a poly-N-acetyllactosamine sugar chain is added is an industrially important subject.

When mechanisms of inflammatory reaction and metastasis are taken into consideration, it is expected that inflammatory reaction can be inhibited and metastasis can be prevented by inhibiting expression of poly-N-acetyllactosamine sugar chain on leukocytes and cancer cells. If a gene for a Gal β1,3-N-acetylglucosaminyltransferase which is involved in the synthesis of a poly-N-acetyllactosamine sugar chain on leukocytes and cancer cells can be obtained, there is a possibility that expression of the poly-N-acetyllactosamine sugar chain on leukocytes and cancer cells can be inhibited by inhibiting expression of the gene.

Also, if a gene for a Gal β1,3-N-acetylglucosaminyltransferase which is involved in the synthesis of a poly-N-acetyllactosamine sugar chain on leukocytes and cancer cells can be obtained, there is a possibility that inflammatory diseases and the malignancy of cancers can be diagnosed by examining the expression level of the gene or examining the expression level of a protein encoded by the gene.

Since it is considered that Gal β1,3-N-acetylglucosaminyltransferases involved in the synthesis of a poly-N-acetyllactosamine sugar chain on specified leukocytes and cancer cells are different, it is necessary to clone and examine an enzyme different from the enzymes so far cloned.

Each of Gal β1,3-N-acetylglucosaminyltransferases expressed in a cell or tissue in which two or more Gal β1,3-N-acetylglucosaminyltransferases are expressed cannot be specified, and enzymological characteristics of each of the Gal β1,3-N-acetylglucosaminyltransferases cannot be clarified by enzymological analyses in which extracts of cells or tissues are used as enzyme sources.

In order to detect the expression of a specified Gal β1,3-N-acetylglucosaminyltransferase, it is necessary to use an immunological detection method by using a specific antibody or a detection method based on the nucleotide sequence of the gene (e.g., Northern hybridization or PCR). Accordingly, it is necessary to clone a Gal β1,3-N-acetylglucosaminyltransferase different from the enzymes so far cloned and compare their expressions.

DISCLOSURE OF THE INVENTION

An object of the present invention is to provide medicaments for anti-inflammatory, anti-infectious, metastasis-inhibiting and the like, foods such as dairy products and the like, a method for improving protein, and a method for diagnosing inflammatory diseases and malignancy of cancers by using a novel polypeptide having a Gal β1,3-N-acetylglucosaminyltransferase activity.

The present invention relates to the following subject matters (1) to (62).

(1) A sugar chain synthesizing agent, which comprises, as an active ingredient, a polypeptide selected from the group consisting of the following (a), (b), (c), (d), (e), (f), (g) and (h), and having an activity involved in synthesis of a poly-N-acetyllactosamine sugar chain:

(a) a polypeptide comprising the amino acid sequence represented by SEQ ID NO:1, (b) a polypeptide comprising an amino acid sequence of positions 41-397 in the amino acid sequence represented by SEQ ID NO:1, (c) a polypeptide comprising the amino acid sequence represented by SEQ ID NO:2, (d) a polypeptide comprising an amino acid sequence of positions 45-372 in the amino acid sequence represented by SEQ ID NO:2, (e) a polypeptide comprising the amino acid sequence represented by SEQ ID NO:3, (f) a polypeptide comprising an amino acid sequence of positions 45-372 in the amino acid sequence represented by SEQ ID NO:3, (g) a polypeptide comprising the amino acid sequence represented by SEQ ID NO:4, and (h) a polypeptide comprising an amino acid sequence of positions 62-378 in the amino acid sequence represented by SEQ ID NO:4.

(2) The sugar chain synthesizing agent according to (1), wherein the polypeptide comprises an amino acid sequence in which one or more amino acids are deleted, substituted or added in the amino acid sequence of the polypeptide according to (1), and has an activity involved in the synthesis of a poly-N-acetyllactosamine sugar chain.

(3) The sugar chain synthesizing agent according to (1) or (2), wherein the activity involved in the synthesis of a poly-N-acetyllactosamine sugar chain is a β1,3-N-acetylglucosaminyltransferase activity.

(4) A polypeptide which is selected from the group consisting of the following (a), (b), (c) and (d):

(a) a polypeptide comprising the amino acid sequence represented by SEQ ID NO:3, (b) a polypeptide comprising an amino acid sequence of positions 45-372 in the amino acid sequence represented by SEQ ID NO:3, (c) a polypeptide comprising the amino acid sequence represented by SEQ ID NO:4, and (d) a polypeptide comprising an amino acid sequence of positions 62-378 in the amino acid sequence represented by SEQ ID NO:4.

(5) A polypeptide comprising an amino acid sequence in which one or more amino acids are deleted, substituted or added in the amino acid sequence represented by SEQ ID NO:4, and having an activity involved in the synthesis of a poly-N-acetyllactosamine sugar chain.

(6) A polypeptide which is the following (a) or (b), and has an activity involved in the synthesis of a poly-N-acetyllactosamine sugar chain;

(a) a polypeptide which comprises an amino acid sequence of positions 41-397 in the amino acid sequence represented by SEQ ID NO:1 and is free of an amino acid sequence of positions 1-33 in the amino acid sequence represented by SEQ ID NO:1, or (b) a polypeptide which comprises an amino acid sequence of positions 45-372 in the amino acid sequence represented by SEQ ID NO:2 and is free of the amino acid sequence represented by SEQ ID NO:2.

(7) A polypeptide comprising an amino acid sequence in which one or more amino acids are deleted, substituted or added in the amino acid sequence of the polypeptide according to (6), and having an activity involved in the synthesis of a poly-N-acetyllactosamine sugar chain.

(8) The polypeptide according to any one of (4) to (7), wherein the activity involved in the synthesis of a poly-N-acetyllactosamine sugar chain is a β1,3-N-acetylglucosaminyltransferase activity.

(9) The polypeptide according to (8), wherein the β1,3-N-acetylglucosaminyltransferase activity of the polypeptide is an activity of transferring N-acetylglucosamine to a galactose residue present in the non-reducing terminal of a sugar chain via a β1,3-linkage.

(10) The polypeptide according to (8) or (9), wherein the β1,3-N-acetylglucosaminyltransferase activity is an activity of transferring N-acetylglucosamine via a β1,3-linkage to a galactose residue present in the non-reducing terminal of an acceptor substrate selected from i) N-acetyllactosamine (Galβ1-4GlcNAc) or lactose (Galβ1-4Glc), ii) an oligosaccharide having an N-acetyllactosamine or lactose structure at the non-reducing terminal, and iii) a complex carbohydrate having an N-acetyllactosamine or lactose structure at the non-reducing terminal.

(11) A glycosyltransferase which is a polypeptide selected from the group consisting of the following (a), (b), (c), (d), (e), (f), (g) and (h), and has an activity involved in the synthesis of a poly-N-acetyllactosamine sugar chain;

(a) a polypeptide comprising the amino acid sequence represented by SEQ ID NO:1, (b) a polypeptide comprising an amino acid sequence of positions 41-397 in the amino acid sequence represented by SEQ ID NO:1, (c) a polypeptide comprising the amino acid sequence represented by SEQ ID NO:2, (d) a polypeptide comprising an amino acid sequence of positions 45-372 in the amino acid sequence represented by SEQ ID NO:2, (e) a polypeptide comprising the amino acid sequence represented by SEQ ID NO:3, (f) a polypeptide comprising an amino acid sequence of positions 45-372 in the amino acid sequence represented by SEQ ID NO:3, (g) a polypeptide comprising the amino acid sequence represented by SEQ ID NO:4, and (h) a polypeptide comprising an amino acid sequence of positions 62-378 in the amino acid sequence represented by SEQ ID NO:4.

(12) The glycosyltransferase according to (11), wherein the polypeptide which comprises an amino acid sequence in which one or more amino acids are deleted, substituted or added in the amino acid sequence of the polypeptide according to (11), and has an activity involved in the synthesis of a poly-N-acetyllactosamine sugar chain.

(13) A DNA which encodes the polypeptide according to any one of (4) to (10).

(14) A DNA which comprises the nucleotide sequence represented by SEQ ID NO:7 or 8.

(15) A DNA which hybridizes with the DNA comprising the nucleotide sequence represented by SEQ ID NO:8 under stringent conditions and encodes a polypeptide having a β1,3-N-acetylglucosaminyltransferase activity.

(16) An agent for detecting inflammation, cancer or metastasis, which comprises the DNA according to any one of (13) to (15).

(17) A recombinant DNA which is obtained by inserting the DNA according to any one of (13) to (15) into a vector.

(18) The recombinant DNA according to (17), wherein the recombinant DNA is a plasmid selected from the group consisting of plasmids pAMo-G4-2, pAMo-G7, pAMoF2-G4, pVL1393-F2G4, pBS-G4-2, and pT7B-G7.

(19) A transformant which comprises the recombinant DNA according to (17) or (18).

(20) The transformant according to (19), wherein the transformant is selected from the group consisting of a microorganism, an animal cell, a plant cell, an insect cell, a non-human transgenic animal, and a transgenic plant.

(21) The transformant according to (20), wherein the microorganism belongs to the genus *Escherichia.*

(22) A biologically pure culture of *Escherichia coli* mM294/pBS-G3 (FERM BP-6694), *Escherichia coli* mM294/pBS-G4 (FERM BP-6695), or *Escherichia coli* mM294/pT7B-G7 (FERM BP-6696).

(23) The transformant according to (20), wherein the animal cell is selected from the group consisting of a mouse myeloma cell, a rat myeloma cell, a mouse hybridoma cell, CHO cell, BHK cell, African green monkey kidney cell, Namalwa cell, Namalwa KJM-1 cell, a human fetal kidney cell, and a human leukemia cell.

(24) The transformant according to (20), wherein the insect cell is selected from the group consisting of a *Spodoptera frugiperda* ovary cell, a *Trichoplusia ni* ovary cell, and a *Bombyx mori* ovary cell.

(25) A process for producing the polypeptide according to any one of (4) to (10), which comprises:

culturing a transformant carrying a recombinant DNA obtained by inserting a DNA encoding the polypeptide into a vector in a medium to produce and accumulate the polypeptide in the culture; and recovering the polypeptide from the culture.

(26) The process according to (25), wherein the transformant is selected from the group consisting of a microorganism, an animal cell, a plant cell, and an insect cell.

(27) A process for producing the polypeptide according to any one of (4) to (10), which comprises:

rearing a non-human transgenic animal carrying a recombinant DNA obtained by inserting a DNA encoding the polypeptide into a vector to produce and accumulate the polypeptide in the animal; and recovering the polypeptide from the animal.

(28) The process according to (27), wherein said production and accumulation are carried out in milk of the animal.

(29) A process for producing the polypeptide according to any one of (4) to (10), which comprises:

cultivating a transgenic plant carrying a recombinant DNA obtained by inserting a DNA encoding the polypeptide into a vector to produce and accumulating the polypeptide in the plant; and recovering the polypeptide from the plant.

(30) A process for producing the polypeptide according to any one of (4) to (10), wherein the polypeptide is synthesized by an in vitro transcription translation system using a DNA encoding the polypeptide.

(31) A process for producing a sugar chain or complex carbohydrate, which comprises:

selecting, as an enzyme source, the sugar chain synthesizing agent according to (1) or (2);

allowing (a) the enzyme source, (b) an acceptor substrate selected from i) N-acetyllactosamine (Galβ1-4GlcNAc), Galβ1-3GlcNAc or lactose (Galβ1-4Glc), ii) an oligosaccharide having an N-acetyllactosamine, Galβ1-3GlcNAc or lactose structure at the non-reducing end, and iii) a complex carbohydrate having an N-acetyllactosamine, Galβ1-3GlcNAc or lactose structure at the non-reducing terminal, and (c) uridine-5'-diphosphate N-acetylglucosamine to be present in an aqueous medium to produce and accumulate a sugar chain or complex carbohydrate in which N-acetylglucosamine is added to a galactose residue of the acceptor substrate via a β1,3-linkage; and recovering the sugar chain or complex carbohydrate from the aqueous medium.

(32) A process for producing a sugar chain or complex carbohydrate to which galactose is added, which comprises:

selecting, as an acceptor substrate, the N-acetylglucosamine-added reaction product obtained by the method according to (31);

allowing (a) the acceptor substrate, (b) a GlcNAc β1,4-galactosyltransferase, and (c) uridine-5'-diphosphogalactose are allowed to be present in an aqueous medium to produce and accumulate a sugar chain or complex carbohydrate in which galactose is added to N-acetylglucosamine residue at the non-reducing terminal of the acceptor substrate via a β1,4-linkage; and recovering the galactose-added sugar chain or complex carbohydrate from the aqueous medium.

(33) A process for producing a sugar chain or complex carbohydrate to which a poly-N-acetyllactosamine sugar chain is added, which comprises:

selecting, as an enzyme source, the sugar chain synthesizing agent according to (1) or (2);

allowing (a) the enzyme source, (b) a GlcNAc β1,4-galactosyltransferase, (c) a acceptor substrate selected from i) N-acetyllactosamine (Galβ1-4GlcNAc), Galβ1-3GlcNAc or lactose (Galβ1-4Glc), ii) an oligosaccharide having an N-acetyllactosamine, Galβ1-3GlcNAc or a lactose structure at the non-reducing end, iii) a complex carbohydrate having an N-acetyllactosamine, Galβ1-3GlcNAc or a lactose structure at the non-reducing terminal, and iv) the reaction product obtained by the process according to (31) or (32), (d) uridine-5'-diphospho-N-acetylglucosamine, and (e) uridine-5'-diphosphogalactose to be present in an aqueous medium to produce and accumulate a sugar chain or complex carbohydrate in which a poly-N-acetyllactosamine sugar chain is added to the non-reducing terminal of the acceptor substrate;

recovering the poly-N-acetyllactosamine sugar chain-added sugar chain or complex carbohydrate from the aqueous medium.

(34) A process for producing a sugar chain or complex carbohydrate, which comprises:

culturing a transformant carrying a recombinant DNA obtained by inserting a DNA encoding a polypeptide which is the active ingredient of the sugar chain synthesizing agent according to (1) or (2) into a vector in a medium to produce and accumulate a sugar chain comprising a saccharide selected from the group consisting of a saccharide having a GlcNAβ1-3Galβ1-4GlcNAc structure, a saccharide having a GlcNAβ1-3Galβ1-3GlcNAc structure, a saccharide having a GlcNAβ1-3Galβ1-4Glc structure, a saccharide having a $(Gal\beta1\text{-}4GlcNA\beta1\text{-}3)_n$Galβ1-4GlcNAc structure wherein n is 1 or more, and a saccharide having a $(Gal\beta1\text{-}4GlcNA\beta1\text{-}3)_n$Galβ1-4Glc structure wherein n is 1 or more, or a complex carbohydrate comprising the sugar chain, in the culture; and recovering the sugar chain or complex carbohydrate from the culture.

(35) The process according to (34), wherein the transformant is a microorganism, an animal cell, a plant cell or an insect cell.

(36) A process for producing a sugar chain or complex carbohydrate, which comprises:

rearing a non-human transgenic animal carrying a recombinant DNA obtained by inserting a DNA encoding a polypeptide which is the active ingredient of the sugar chain synthesizing agent according to (1) or (2) into a vector to produce and accumulate a sugar chain comprising a saccharide selected from the group consisting of a saccharide having a GlcNAβ1-3Galβ1-4GlcNAc structure, a saccharide having a GlcNAβ1-3Galβ1-3GlcNAc structure, a saccharide having a GlcNAβ1-3Galβ1-4Glc structure, a saccharide having a $(Gal\beta1\text{-}4GlcNA\beta1\text{-}3)_n$Galβ1-4GlcNAc structure wherein n is 1 or more, and a saccharide having a $(Gal\beta1\text{-}4GlcNA\beta1\text{-}3)_n$Galβ1-4Glc structure wherein n is 1 or more, or a complex carbohydrate comprising the sugar chain, in the animal; and recovering the sugar chain or complex carbohydrate from the animal.

(37) A process for producing a sugar chain or complex carbohydrate, which comprises:

cultivating a transgenic plant carrying a recombinant DNA obtained by inserting a DNA encoding a polypeptide which is the active ingredient of the sugar chain synthesizing agent according to (1) or (2) into a vector to produce and accumulate a sugar chain comprising a saccharide selected from the group consisting of a saccharide having a GlcNAβ1-3Galβ1-4GlcNAc structure, a saccharide having a GlcNAβ1-3Galβ1-3GlcNAc structure, a saccharide having a GlcNAβ1-3Galβ1-4Glc structure, a saccharide having a $(Gal\beta1\text{-}4GlcNA\beta1\text{-}3)_n$Galβ1-4GlcNAc structure wherein n is 1 or more, and a saccharide having a $(Gal\beta1\text{-}4GlcNA\beta1\text{-}3)_n$Galβ1-4Glc structure wherein n is 1 or more, or a complex carbohydrate comprising the sugar chain, in the plant; and recovering the sugar chain or complex carbohydrate from the plant.

(38) The process according to any one of (31) to (37), wherein the complex carbohydrate is a complex carbohydrate selected from a glycoprotein, a glycolipid, a proteoglycan, a glycopeptide, a lipopolysaccharide, a peptidoglycan, and a glycoside in which a sugar chain is bound to a steroid compound.

(39) The process according to (36), wherein said production and accumulation are carried out in milk of the animal.

(40) A method for determining an expression level of a gene encoding a polypeptide having the amino acid sequence represented by any one of SEQ ID NO:1 to 4, which comprises carrying out hybridization by using the DNA according to any one of (13) to (15).

(41) An oligonucleotide which is selected from an oligonucleotide having a sequence identical to continuous 6 to 60 nucleotides of a DNA having the nucleotide sequence represented by SEQ ID NO:8, an oligonucleotide having a sequence complementary to the oligonucleotide, and a derivative of the oligonucleotide.

(42) The oligonucleotide according to (41), wherein the derivative of oligonucleotide is selected from an oligonucleotide derivative in which a phosphodiester bond in the oligonucleotide is converted into a phosphorothioate bond, an oligonucleotide derivative in which a phosphodiester bond in the oligonucleotide is converted into an N3'-P5' phosphoamidate bond, an oligonucleotide derivative in which ribose and a phosphodiester bond in the oligonucleotide are converted into a peptide-nucleic acid bond, an oligonucleotide derivative in which uracil in the oligonucleotide is substituted with C-5 propynyluracil, an oligonucleotide derivative in which uracil in the oligonucleotide is substituted with C-5 thiazoleuracil, an oligonucleotide derivative in which cytosine in the oligonucleotide is substituted with C-5 propynylcytosine, an oligonucleotide derivative in which cytosine in the oligonucleotide is substituted with phenoxazine-modified cytosine, an oligonucleotide derivative in which ribose in the oligonucleotide is substituted with 2'-O-propylribose, and an oligonucleotide derivative in which ribose in the oligonucleotide is substituted with 2'-methoxyethoxyribose.

(43) A method for determining an expression level of a gene encoding the polypeptide according to any one of (4) to (10), which comprises carrying out a polymerase chain reaction by using an oligonucleotide selected from an oligonucleotide having a sequence identical to continuous 6 to 60 nucleotides of a nucleotide sequence of a DNA encoding the polypeptide according to any one of (4) to (10), an oligonucleotide having a sequence complementary to the oligonucleotide, and a derivative of the oligonucleotide.

(44) A method for detecting inflammation, cancer or metastasis, which comprises using the method according to (40) or (43).

(45) A method for inhibiting transcription of a DNA encoding the polypeptide according to any one of (4) to (10) or translation of the mRNA corresponding to the DNA, which comprises using an oligonucleotide selected from an oligonucleotide having a sequence identical to continuous 6 to 60 nucleotides of a nucleotide sequence of the DNA according to any one of (13) to (15), an oligonucleotide having a sequence complementary to the oligonucleotide, and a derivative of the oligonucleotide.

(46) An oligonucleotide selected from an oligonucleotide having a sequence identical to continuous 6 to 60 nucleotides of a nucleotide sequence of a DNA encoding the polypeptide according to any one of (4) to (10), an oligonucleotide having a sequence complementary to the oligonucleotide, and a derivative of the oligonucleotide.

(47) An antibody which recognizes the polypeptide according to any one of (4) to (10).

(48) A method for immunologically detecting the polypeptide according to any one of (4) to (10), which comprises using the antibody according to (47).

(49) An immunohistostaining method, which comprises detecting the polypeptide according to any one of (4) to (10) by using the antibody according to (47).

(50) An immunohistostaining agent, comprising the antibody according to (47).

(51) An agent for diagnosing inflammation, cancer or metastasis, which comprises the antibody according to (47).

(52) A method for screening a compound capable of changing the β1,3-N-acetylglucosaminyltransferase activity of the polypeptide according to any one of (4) to (10), which comprises bringing the polypeptide into contact with a test sample.

(53) A method for screening a compound capable of changing the expression of a gene encoding the polypeptide according to any one of (4) to (10), which comprises:

bringing a cell in which the polypeptide is expressed, into contact with a test sample; and measuring the content of the poly-N-acetyllactosamine sugar chain by using an antibody or a lectin capable of recognizing the poly-N-acetyllactosamine sugar chain.

(54) A method for screening a compound which changes the expression of a gene encoding the polypeptide according to any one of (4) to (10), which comprises:

bringing a cell expressing the polypeptide into contact with a test sample; and measuring the polypeptide content by using the antibody according to (47).

(55) A promoter DNA, which is capable of controlling the transcription of the gene encoding the polypeptide according to any one of (4) to (10).

(56) The promoter DNA according to (55), wherein the promoter DNA which functions in a cell selected from a leukocyte, a small intestine cell, a large intestine cell, a spleen cell, a stomach cell, a large bowel cancer cell, a pancreatic cancer cell, and a gastric cancer cell.

(57) The promoter DNA according to (55) or (56), wherein the promoter DNA which derives from human or mouse.

(58) A method for screening a compound capable of changing the efficiency of transcription by the promoter according to any one of (55) to (57), which comprises:

transforming an animal cell with a plasmid containing the promoter DNA and a reporter gene linked to downstream of the promoter DNA;

bringing the resulting transformant into contact with a test sample; and measuring the content of the translation product of the reporter gene.

(59) The method according to (58), wherein the reporter gene is selected from a chloramphenicol acetyltransferase gene, a β-galactosidase gene, a β-lactamase gene, a luciferase gene, and a green fluorescent protein gene.

(60) A compound obtained by the method according to any one of (52) to (54), (58) and (59).

(61) A knock out non-human animal in which a DNA encoding the polypeptide according to any one of (4) to (10) is deleted or mutated.

(62) The knock out non-human animal according to (61), wherein the knock out non-human animal is a mouse.

The present invention is explained below in detail.

(1) Acquisition of a DNA Encoding a Protein Homologous to a GlcNAc β1,3-Galactosyltransferase (β3Gal-T1) and Production of the DNA and the Oligonucleotide β3Gal-T1 (another name WM1) is a GlcNAc β1,3-galactosyltransferase involved in the synthesis of a Galβ1-3GlcNAc structure (Japanese Published Unexamined Patent Application No. 181759/94). A gene having homology with the gene encoding this enzyme or a gene having a possibility of encoding a protein having homology with this enzyme at the amino acid level is searched based on gene data bases by using a program such as Blast [Altschul et al., *J. Mol. Biol.*, 215, 403 (1990)], FrameSearch method (manufactured by Compugen) or the like. As data bases, a public data base such as GenBank or the like can be used, and a private data base can also be used. The presence of DNAs having the corresponding sequence can be detected by carrying out polymerase chain reaction (hereinafter referred to as "PCR") [*Molecular Cloning, A Laboratory Manual,* 2nd Ed., Cold Harbor Laboratory Press (1989) (hereinafter referred to as "*Molecular Cloning,* 2nd Ed.") and *PCR Protocols*, Academic Press (1990)] by using a single-stranded cDNA or a cDNA library prepared from various organs or various cells as a template and using primers specific for the corresponding sequence. Also, a DNA fragment having the corresponding sequence can be obtained in the same manner.

When the thus obtained DNA fragment is not a full length, its full-length cDNA can be obtained as follows.

A full-length cDNA can be obtained by screening an organ- or cell-derived cDNA library in which the presence of the DNA has been confirmed, by using the DNA fragment obtained in the above as a probe.

Also, a 5'-end side fragment and a 3'-end side fragment of a cDNA having the corresponding sequence can be obtained by carrying out 5'-RACE method and 3'-RACE method using a single-stranded cDNA or cDNA library as the template in which the presence of the DNA has been confirmed. By ligating both fragments, a full-length cDNA can be obtained.

The single-stranded cDNA derived from various organs or various cells can be prepared in accordance with the usual method or by using a commercially available kit. An example is shown below.

A total RNA is extracted from various organs or various cell by the acid guanidium thiocyanate phenol-chloroform method [*Anal. Biochem.*, 162, 156 (1987)]. If necessary, the total RNA is treated with deoxyribonuclease I (manufactured by Life Technologies) to degrade possible chromosomal DNAs of contaminating. Using each of the thus obtained total RNA samples, single-stranded cDNAs are synthesized by SUPERSCRIPT™ Preamplification System for First Strand cDNA System (manufactured by Life Technologies) by using oligo(dT) primers or random primers. Examples of single-stranded cDNAs include single-stranded cDNAs prepared from a human neuroblastoma cell line SK-N-MC by the above method.

The cDNA library can be prepared by the usual method. Examples of the cDNA library preparation method include the method described in *Molecular Cloning,* 2nd Ed., *Current Protocols in Molecular Biology, DNA Cloning* 1*: Core Techniques, A Practical Approach,* 2nd Ed., Oxford University Press (1995) or the like, and the method in which a commercially available kit such as SuperScript Plasmid System for cDNA Synthesis and Plasmid Cloning (manufactured by GIBCO BRL) or ZAP-cDNA Synthesis Kit (manufactured by STRATAGENE) is used, and the like. A cDNA library derived from various organs or various cells can also be obtained by purchasing a commercially available product.

As the cloning vector for preparing a cDNA library, any one of phage vectors, plasmid vectors and the like can be used, so long as it can replicate autonomously in *Escherichia coli* K12. Examples include ZAP Express [manufactured by STRATAGENE, *Strategies,* 5, 58 (1992)], pBluescript II SK(+) [*Nucleic Acids Research,* 17, 9494 (1989)], λZAP II (manufactured by STRATAGENE), λgt10 *[DNA Cloning, A Practical Approach,* 1, 49 (1985)], λTriplEx (manufactured by Clontech), λExCell (manufactured by Pharmacia), pT7T318U (manufactured by Pharmacia), pcD2 *[Mol. Cell. Biol.,* 3, 280 (1983)], pUC18 *[Gene,* 33, 103 (1985)], pAMo [*J. Biol. Chem.,* 268, 22782 (1993), alias pAMoPRC3Sc (Japanese Published Unexamined Patent Application No. 336963/93)] and the like.

As the host microorganism, any microorganism can be used, so long as it belongs to *Escherichia coli*. Specifically, *Escherichia coli* XL1-Blue MRF' [manufactured by STRATAGENE, *Strategies,* 5, 81 (1992)], *Escherichia coli* C600 *[Genetics,* 39, 440 (1954)], *Escherichia coli* Y1088 *[Science,* 222, 778 (1983)], *Escherichia coli* Y1090 *[Science,* 222, 778 (1983)], *Escherichia coli* NM522 *[J. Mol. Biol.,* 166, 1 (1983)], *Escherichia coli* K802 *[J. Mol. Biol.,* 16, 118 (1966)], *Escherichia coli* JM105 *[Gene,* 38, 275 (1985)], *Escherichia coli* SOLR™ Strain (available from STRATAGENE), *Escherichia coli* LE392 (*Molecular Cloning,* 2nd Ed.) and the like.

As the cDNA library, mention may be made of a cDNA library prepared as follows.

A cDNA library is prepared by synthesizing cDNAs from human gastric mucosa poly(A)+ RNA by using cDNA Synthesis System (manufactured by GIBCO BRL), adding an EcoRI-NotI-SalI adapter (Super Choice System for cDNA Synthesis; manufactured by GIBCO BRL) to their both termini, inserting them into the EcoRI site of a cloning vector λZAP II (λZAP II/EcoRI/CIAP Cloning Kit, manufactured by STRATAGENE), and then carrying out in vitro packaging by using Gigapack III Gold Packaging Extract manufactured by STRATAGENE. Alternatively, a commercially available cDNA library can be used.

Based on the nucleotide sequence of a candidate gene found by the data base search, primers specific for the gene are designed and PCR is carried out by using the thus obtained single-stranded cDNAs or a cDNA library as the templates. When an amplified fragment is obtained, the fragment is subcloned into an appropriate plasmid. The subcloning can be carried out by inserting the amplified DNA fragment directly, or after its treatment with a restriction enzyme or DNA polymerase, into a vector in the usual way. Examples of the vector include pBluescript SK(−), pBluescript II SK(+) (both manufactured by STRATAGENE), pDIRECT [*Nucleic Acids Research,* 18, 6069 (1990)], pCR-Amp SK(+) [manufactured by Stratagene, *Strategies,* 5, 6264 (1992)], pT7Blue (manufactured by Novagen), pCR II [manufactured by Invitrogen; *Biotechnology,* 9, 657 (1991)], pCR-TRAP (manufactured by Genehunter), pNoTA$_{T7}$ (manufactured by 5'→3') and the like.

Acquisition of the DNA fragment of interest is confirmed by determining the nucleotide sequence of the subcloned PCR amplification fragment. The nucleotide sequence can be determined by the generally used nucleotide sequence analyzing method such as the dideoxy method of Sanger et al. [*Proc. Natl. Acad. Sci. USA,* 74, 5463 (1997)] or by using the nucleotide sequence analyzing apparatus such as 373A DNA sequencer (manufactured by PERKIN ELMER) or the like.

By carrying out colony hybridization or plaque hybridization (*Molecular Cloning,* 2nd Ed.) for the cDNA library prepared in the above by using the DNA fragment as a probe, cDNA having a possibility of encoding a protein having homology with β3Gal-T1 at the amino acid level can be obtained. As the probe, the DNA fragment labeled with an isotope or digoxigenin can be used.

The nucleotide sequence of the DNA obtained by the above method can be determined by inserting the DNA fragment as such or after its digestion with an appropriate restriction enzyme or the like into a vector by the general method described in *Molecular Cloning,* 2nd Ed. or the like, and then analyzing it by the generally used nucleotide sequence analyzing method such as the dideoxy method of Sanger et al. [*Proc. Natl. Acad. Sci. USA,* 74, 5463 (1997)] or using a nucleotide sequence analyzing apparatus such as 373A DNA sequencer (manufactured by PERKIN ELMER) or the like.

Examples of the DNA obtained by the method include DNAs encoding the polypeptide represented by SEQ ID NO:1, 2, or 4. Specific examples include DNAs having the nucleotide sequence represented by SEQ ID NO:5, 6, 7 or 8. Examples of a plasmid containing the DNA of SEQ ID NO:5 include pAMo-G3 and pBS-G3. Examples of a plasmid containing the DNA of SEQ ID NO:6 include pAMo-G4 and pBS-G4. Examples of a plasmid containing the DNA of SEQ ID NO:7 include pAMo-G4-2 and pBS-G4-2. Examples of a plasmid containing the DNA of SEQ ID NO:8 include pAMo-G7 and pT7B-G7.

The DNA of interest encoding a polypeptide comprised of an amino acid sequence in which one or more amino acids are deleted, substituted or added when compared with the amino acid sequence represented by SEQ ID NO:1, 2, 3 or 4 can be obtained by selecting a DNA which hybridizes with the DNA obtained by the above method under stringent conditions. For example, the DNA of interest can be obtained by screening for a cDNA library derived from other species (mouse, rat, calf, monkey or the like).

A DNA which is hybridizable under stringent conditions is a DNA obtained by carrying out colony hybridization, plaque hybridization, Southern hybridization or the like using the DNA obtained in the above as a probe. Examples include a DNA which can be identified by carrying out hybridization at 65° C. in the presence of 0.7 to 1.0 M sodium chloride using a filter to which colony- or plaque-derived DNA samples are immobilized and then washing the filter at 65° C. with 0.1 to 2-fold concentrated SSC solution (1-fold concentrated SSC solution contains 150 mmol/l sodium chloride and 15 mmol/l sodium citrate). The hybridization can be carried out in accordance with the method described in *Molecular Cloning,* 2nd Ed., *Current Protocols in Molecular Biology*, John Wiley & Sons (1987-1997) (hereinafter referred to as "*Current Protocols in Molecular Biology*"), *DNA Cloning* 1*: Core Techniques, A Practical Approach,* 2nd Ed., Oxford University Press (1995) or the like. Examples of the hybridizable DNA include a DNA having at least 60% or more of homology, preferably a DNA having 80% or more of homology, more preferably a DNA having 95% or more of homology, with the DNA obtained in the above, when calculated using BLAST [*J. Mol. Biol.,* 215, 403 (1990)], FASTA [*Methods in Enzymology,* 183, 63-98 (1990)] or the like.

The DNA of interest encoding a polypeptide comprised of an amino acid sequence in which one or more amino acids are deleted, substituted or added can be obtained by using a site-directed mutagenesis method described in *Molecular Cloning,* 2nd Ed., *Current Protocols in Molecular Biology, Nucleic Acids Research,* 10, 6487 (1982), *Proc. Natl. Acad. Sci. USA,* 79, 6409 (1982), *Gene,* 34, 315 (1985), *Nucleic Acids Research,* 13, 4431 (1985), *Proc. Natl. Acad. Sci. USA,* 82, 488 (1985) or the like, for example by introducing the site-directed mutagenesis into a DNA encoding a polypeptide having the amino acid sequence represented by SEQ ID NO:1. The number of amino acids to be deleted, substituted or added is not particularly limited, but limited within such a range that polypeptides of the present invention do not include known polypeptides, and from 1 to several tens, particularly from 1 to several, of amino acids are preferable. Also, in order to maintain a β1,3-N-acetylglucosaminyltransferase activity of the polypeptide of the present invention, it is preferable that it has 60% or more, generally 80% or more, particularly 95% or more, of homology with, for example, the amino acid sequence represented by SEQ ID NO:1.

The DNA of interest can also be prepared by chemically synthesizing a DNA encoding the polypeptide based on the determined amino acid sequence of the novel glycosyltransferase polypeptide. Chemical synthesis of the DNA can be carried out by using a DNA synthesizer manufactured by Shimadzu which employs the thiophosphite method, a DNA synthesizer model 392 manufactured by PERKIN ELMER which employs the phosphoamidite method, and the like.

The DNA of interest can also be prepared by carrying out PCR using oligonucleotides described below as a sense primer and an antisense primer, and by using cDNAs prepared from a cell expressing mRNA complementary to these DNA molecules as the template.

Oligonucleotides, such as antisense oligonucleotide, sense oligonucleotide and the like, having a partial sequence of the DNA of the present invention can be prepared by using the DNA and DNA fragments of the present invention obtained by the above method, in accordance with the general method described in *Molecular Cloning,* 2nd Ed. or the like, or by using a DNA synthesizer based on the nucleotide sequence information on the DNA.

Examples of the oligonucleotide include a DNA having a sequence identical to continuous 5 to 60 nucleotides in a nucleotide sequence contained in the above DNA. Specific examples include a DNA having a sequence identical to continued 5 to 60 nucleotides in the nucleotide sequence represented by SEQ ID NO:5, 6, 7 or 8 or a DNA having a sequence complementary to the above DNA. When used as a sense primer and an antisense primer, the above oligonucleotides in which the melting temperature (Tm) and the number of bases are not significantly different from each other are preferable. Specifically, oligonucleotides having the nucleotide sequences shown in SEQ ID NOS:9-20 can be exemplified.

In addition, derivatives of these oligonucleotides (hereinafter referred to as "oligonucleotide derivatives") can also be used as the oligonucleotides of the present invention.

Examples of the oligonucleotide derivatives include oligonucleotide derivatives in which a phosphodiester bond in the oligonucleotide is converted into a phosphorothioate bond, oligonucleotides derivative in which a phosphodiester bond in the oligonucleotide is converted into an N3'-P5' phosphoamidate bond, oligonucleotide derivatives in which ribose and a phosphodiester bond in the oligonucleotide are converted into a peptide-nucleic acid bond, oligonucleotide derivatives in which uracil in the oligonucleotide is substituted with C-5 propynyluracil, oligonucleotide derivatives in which uracil in the oligonucleotide is substituted with C-5 thiazoleuracil, oligonucleotide derivatives in which cytosine in the oligonucleotide is substituted with C-5 propynylcytosine, oligonucleotide derivatives in which cytosine in the oligonucleotide is substituted with phenoxazine-modified cytosine, oligonucleotide derivatives in which ribose in the oligonucleotide is substituted with 2'-O-propylribose, oligonucleotide derivatives in which ribose in the oligonucleotide is substituted with 2'-methoxyethoxyribose, and the like [*Cell Technology,* 16, 1463 (1997)].

(2) Determination of an Activity of a Polypeptide Encoded by the Obtained DNA

An expression plasmid is constructed by inserting the DNA obtained in the above manner into an expression vector. After introducing the plasmid into an appropriate animal cell, whether or not the DNA is involved in the synthesis of sugar chains can be examined according to the fluorescence activated cell sorter (hereinafter referred to as "FACS") analysis by using an antibody or lectin which specifically binds to a sugar chain (poly-N-acetyllactosamine sugar chain, sialyl Lewis a sugar chain or sialyl Lewis c sugar chain).

Any expression vector can be used, so long as the cDNA can be inserted and the vector can function in an animal cell. Examples include pcDNAI/Amp, pcDNAI, pCDM8 (both available from Funakoshi), pAGE107 [(Japanese Published Unexamined Patent Application No. 22979/92, *Cytotechnology,* 3, 133 (1990)], pREP4 (manufactured by Invitrogen), pAGE103 [*J. Biochem.,* 101, 1307 (1987)], pAMo, pAMoA [[*J. Biol. Chem.,* 268, 22782 (1993), alias pAMoPRSA (Japanese Published Unexamined Patent Application No. 336963/93)], pAS3-3 (Japanese Published Unexamined Patent Application No. 227075/90) and the like.

A transformed cell is obtained by introducing the cDNA-inserted expression vector into an animal cell which can be used in selecting the cDNA of interest.

Regarding the method for introducing this expression vector, any method for introducing DNA into animal cells can be used. Examples include electroporation method [*Cytotechnology,* 3, 133 (1990)], calcium phosphate method (Japanese Published Unexamined Patent Application No. 227075/90), lipofection method [*Proc. Natl. Acad. Sci. USA,* 84, 7413 (1987)] and the like.

Examples of the animal cell include Namalwa cell as a human cell, Namalwa KJM-1 cell as a sub-line of Namalwa cell, 293 cell, COS cell as a monkey cell, CHO cell as a Chinese hamster cell and HBT5637 (Japanese Published Unexamined Patent Application No. 299/88). Among these, Namalwa cell and Namalwa KJM-1 cell are preferred.

The thus obtained transformed cell is cultured by the general method.

Specifically, the following culturing method for transformants can be exemplified.

Examples of the medium for culturing the cell include RPMI 1640 medium [*The Journal of the American Medical Association,* 199, 519 (1967)], Eagle's MEM medium [*Science,* 122, 501 (1952)], DMEM medium [*Virology,* 8, 396 (1959)], 199 medium [*Proceeding of the Society for the Biological Medicine,* 73, 1 (1950)] and a medium prepared by adding fetal bovine serum or the like to any of these media, and the like.

Culturing is carried out generally at pH 6 to 8 and at 30 to 40° C. in the presence of 5% $CO_2$ for 1 to 7 days. Also, if necessary, antibiotics such as kanamycin, penicillin and the like may be added to the medium.

The transformed cell obtained by the culturing is subjected to fluorescence staining using an antibody or lectin which specifically binds to a sugar chain (poly-N-acetyllactosamine sugar chain, sialyl Lewis a sugar chain or sialyl Lewis c sugar chain) and then analyzed by using FACS. When a poly-N-acetyllactosamine sugar chain is produced in an increased amount in comparison with a transformed cell into which a control plasmid is introduced, it can be considered that the novel polypeptide encoded by the DNA has a β1,3-N-acetylglucosaminyltransferase activity which involved in the synthesis of the poly-N-acetyllactosamine sugar chain. On the other hand, when a sialyl Lewis a sugar chain or sialyl Lewis c sugar chain is produced in an increased amount, it can be considered that the novel polypeptide encoded by the DNA has a β-1,3-galactosyltransferase activity involved in the synthesis of the sialyl Lewis a sugar chain or sialyl Lewis c sugar chain.

As a antibody or lectin which recognizes a poly-N-acetyllactosamine sugar chain, any substance capable of recognizing s poly-N-acetyllactosamine sugar chain can be used. Examples of the antibody which recognizes a poly-N-acetyllactosamine sugar chain include anti-i antibody. Examples of the lectin which recognizes poly-N-acetyllactosamine sugar chain include pokeweed mitogen (referred to as "PWM"), *Lycopersicon esculentum* (tomato) agglutinin (referred to as "LEA") and *Datura stramonium* agglutinin (referred to as "DSA") [*J. Biol. Chem.,* 282, 8179 (1987), *J. Biol. Chem.,* 259, 6253 (1984), *J. Biol. Chem.,* 262, 1602 (1987), *Carbohydr. Res.,* 120, 187 (1983), *Carbohydr. Res.,* 120, 283-292 (1983), *Glycoconjugate J.,* 7, 323 (1990)].

As an anti-sialyl Lewis a sugar chain antibody or anti-sialyl Lewis c sugar chain antibody, any antibody which reacts with a sialyl Lewis a sugar chain or sialyl Lewis sugar chain can be used. Examples include 19-9 (manufactured by Fujirebio) and KM231 (manufactured by Kyowa Medex) as the anti-sialyl Lewis a sugar chain antibodies, and DU-PAN-2 (manufactured by Kyowa Medex) as the anti-sialyl Lewis c sugar chain antibody.

Also, a β1,3-N-acetylglucosaminyltransferase activity can be measured using a cell extract of the above transformed cell in accordance with the known measuring methods [*J. Biol. Chem.,* 268, 27118 (1993), *J. Biol. Chem.,* 267, 2994 (1992), *J. Biol. Chem.,* 263, 12461 (1988), *Jpn. J. Med. Sci, Biol.,* 42, 77 (1989)]. When the amount of β1,3-N-acetylglucosaminyltransferase activity is increased in comparison with a transformed cell into which a control plasmid is introduced, it can be considered that the novel polypeptide encoded by the DNA has a β1,3-N-acetylglucosaminyltransferase activity.

Also, a β1,3-galactosyltransferase activity of the polypeptide of the present invention can be measured in accordance with the known measuring methods [*J. Biol. Chem.*, 258, 9893-9898 (1983), *J. Biol. Chem.*, 262, 15649 (1987), *Archi. Biochem. Biophys.*, 270, 630 (1989), *Archi. Biochem. Biophys.*, 274, 14 (1989), Japanese Published Unexamined Patent Application No. 181759/94, *J. Biol. Chem.*, 273, 58 (1998), *J. Biol. Chem.*, 273, 433 (1998), *J. Biol. Chem.*, 273, 12770 (1998), *J. Biol. Chem.*, 274, 12499 (1999)].

In the above manner, the activity of the obtained novel polypeptide encoded by the novel cDNA can be found.

(3) Production of a Novel β1,3-N-Acetylglucosaminyltransferase Polypeptide

In order to produce the polypeptide of the present invention by expressing the DNA of the present invention obtained by the method described in the above in a host cell, the methods described in *Molecular Cloning*, 2nd Ed., *Current Protocols in Molecular Biology, Supplements* 1 to 38 (*Current Protocols in Molecular Biology*) and the like can be used.

That is, the polypeptide of the present invention can be produced by constructing a recombinant vector in which the DNA of the present invention is inserted into downstream of a promoter in an appropriate expression vector, introducing the vector into a host cell to thereby obtain a transformant capable of expressing the polypeptide of the present invention, and then culturing the transformant.

As the host cell, any one of prokaryotic cells, yeast cells, animal cells, insect cells, plant cells and the like can be used, so long as the gene of interest is expressed in the cell.

The expression vector to be used is a vector which can autonomously replicate in the above host cells or can be integrated into chromosome and contains a promoter at a position suitable for the transcription of the novel β1,3-N-acetylglucosaminyltransferase gene.

When a prokaryotic organism such as a bacterium or the like is used as the host cell, it is preferable that the expression vector of the novel β1,3-N-acetylglucosaminyltransferase gene can autonomously replicate in the prokaryotic organism and is constituted from a promoter, a ribosome binding sequence, the novel β1,3-N-acetylglucosaminyltransferase gene and a transcription termination sequence. A gene which controls the promoter may also be contained.

Examples of the expression vector include pBTrp2, pBTac1, pBTac2 (all available from Boehringer-Mannheim), pSE280 (manufactured by Invitrogen), pGEMEX-1 (manufactured by Promega), pQE-8 (manufactured by QIAGEN), pKYP10 (Japanese Published Unexamined Patent Application No. 110600/83), pKYP200 [*Agric. Biol. Chem.*, 48, 669 (1984)], pLSA1 [*Agric. Biol. Chem.*, 53, 277 (1989)], pGEL1 [*Proc. Natl. Acad. Sci. USA*, 82, 4306 (1985)], pBluescript II SK(−) (manufactured by STRATAGENE), pTrs30 (FERM BP-5407), pTrs32 (FERM BP-5408), pGHA2 (FERM BP-400), pGKA2 (FERM B-6798), pTerm2 (Japanese Published Unexamined Patent Application No. 22979/91, U.S. Pat. No. 4,686,191, U.S. Pat. No. 4,939,094, U.S. Pat. No. 5,160,735), pKK233-2 (manufactured by Pharmacia), pGEX (manufactured by Pharmacia), pET system (manufactured by Novagen), pSupex, pUB110, pTP5, pC194, pTrxFus (manufactured by Invitrogen), pMAL-c2 (manufactured by New England Biolabs) and the like.

As the promoter, any promoter may be used so long as it can be expressed in host cells such as *Escherichia coli* and the like. Examples include promoters, such as trp promoter (Ptrp), lac promoter (Plac), $P_L$ promoter, $P_R$ promoter and the like, derived from *Escherichia coli*, phage and the like, and SPO1 promoter, SPO2 promoter, penP promoter and the like. In addition, artificially designed and modified promoters such as a promoter in which two Ptrp are linked in tandem (Ptrp×2), tac promoter, lacT7 promoter, letI promoter and the like can also be used.

As the ribosome binding sequence, it is preferable to use a plasmid in which the space between the Shine-Dalgarno sequence and initiation codon is adjusted at an appropriate distance (e.g., 6 to 18 nucleotides).

Although a transcription termination sequence is not always necessary for the expression of the DNA of the present invention, it is preferable to arrange the transcription termination sequence just below the structural gene.

Examples of the host cell include microorganisms belonging to the genus *Escherichia*, the genus *Serratia*, the genus *Bacillus*, the genus *Brevibacterium*, the genus *Corynebacterium*, the genus *Microbacterium*, the genus *Pseudomonas* and the like, such as *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* BL21(DE3), *Escherichia coli* BL21(DE3) pLysS, *Escherichia coli HMS*174(DE3), *Escherichia coli* HMS174(DE3)pLysS, *Serratia ficaria, Serratia fonticola, Serratia liquefaciens, Serratia marcescens, Bacillus subtilis, Bacillus amyloliquefaciens, Brevibacterium ammoniagenes, Brevibacterium immariophilum* ATCC 14068, *Brevibacterium saccharolyticum* ATCC 14066, *Corynebacterium glutamicum* ATCC 13032, *Corynebacterium glutamicum* ATCC 14067, *Corynebacterium glutamicum* ATCC 13869, *Corynebacterium acetoacidophilum* ATCC 13870, *Microbacterium ammoniaphilum* ATCC 15354, *Pseudomonas* sp. D-0110 and the like.

Regarding the method for introducing the recombinant vector, any method in which DNA can be introduced into the above host cells can be used. Examples include electroporation method [*Nucleic Acids Res.*, 16, 6127 (1988)], a method which uses calcium ion [*Proc. Natl. Acad. Sci. USA*, 69, 2110 (1972)], protoplast method (Japanese Published Unexamined Patent Application No. 248394/88), the methods described in *Gene*, 17, 107 (1982) and *Molecular & General Genetics*, 168, 111 (1979) and the like.

When yeast is used as the host cell, YEp13 (ATCC 37115), YEp24 (ATCC 37051), YCp50 (ATCC 37419), pHS19, pHS15 and the like can, for example, be used as the expression vector.

Any promoter can be used so long as it can be expressed in yeast. Examples include PH05 promoter, PGK promoter, GAP promoter, ADH promoter, gal 1 promoter, gal 10 promoter, heat shock protein promoter, MF α1 promoter, CUP 1 promoter and the like.

Examples of the host cell include yeast belonging to the genus *Saccharomyces*, the genus *Schizosaccharomyces*, the genus *Kluyveromyces*, the genus *Trichosporon*, the genus *Schwanniomyces* and the like. Specific examples include *Saccharomyces cerevisiae, Schizosaccharomyces pombe, Kluyveromyces lactis, Trichosporon pullulans, Schwanniomyces alluvius* and the like.

Regarding the method for introducing the recombinant vector, any one of the methods for introducing DNA into yeast can be used. Examples include electroporation method [*Methods in Enzymology*, 194, 182 (1990)], spheroplast method [*Proc. Natl. Acad. Sci. USA*, 84, 1929 (1978)], lithium acetate method [*J. Bacteriol.*, 153, 163 (1983)], a method described in *Proc. Natl. Acad. Sci. USA*, 75, 1929 (1978) and the like.

When an animal cell is used as the host, pcDNAI/Amp, pcDNAI, pCDM8, pAGE107, pREP4, pAGE103, pAMo, pAMoA, pAS3-3 and the like can be exemplified as the expression vector.

Any promoter allowing the expression in animal cells can be used. Examples include the promoter of IE (immediate early) gene of cytomegalovirus (CMV), the early promoter of SV40, the long terminal repeat promoter of Moloney murine leukemia virus, the promoter of retrovirus, the heat shock promoter, the SRα promoter, the promoter of metallothionein and the like. Also, the enhancer of the IE gene of human CMV may be used together with the promoter.

Examples of the host cell include a mouse myeloma cell, a rat myeloma cell, a mouse hybridoma cell, CHO cell as Chinese hamster cell, BHK cell, African green monkey kidney cell, Namalwa cell or Namalwa KJM-1 cell as a human cell, a human fetal kidney cell, a human leukemia cell, HBT5637 (Japanese Published Unexamined Patent Application No. 299/88), a human colon cancer cell line and the like.

The mouse myeloma cells include SP2/0, NS0 and the like. The rat myeloma cells include YB2/0 and the like. The human fetal kidney cells include HEK293, 293 and the like. The human leukemia cells include BALL-1 and the like. The African green monkey kidney cells include COS-1, COS-7 and the like. The human large bowel cancer cell lines include HCT-15 and the like.

Regarding the method for introducing the recombinant vector, any one of the methods for introducing DNA into animal cells can be used. Examples include electroporation method [*Cytotechnology,* 3, 133 (1990)], calcium phosphate method (Japanese Published Unexamined Patent Application No. 227075/90), lipofection method [*Proc. Natl. Acad. Sci. USA,* 84, 7413 (1987)], the method described in *Virology,* 52, 456 (1973) and the like. Preparation of a transformant and its culturing can be carried out in accordance with the method described in Japanese Published Unexamined Patent Application No. 227075/90 or Japanese Published Unexamined Patent Application No. 257891/90.

When insect cells are used as the host, the polypeptide can be expressed by the method described, for example, in *Baculovirus Expression Vectors, A Laboratory Manual*, W.H. Freeman and Company, New York (1992), *Molecular Biology, A Laboratory Manual, Current Protocols in Molecular Biology*, Supplements 1 to 38 or *Bio/Technology,* 6, 47 (1988).

That is, the polypeptide can be expressed by simultaneously cotransfecting a recombinant gene transfer vector and a baculovirus into an insect cell to obtain a recombinant virus in an insect cell culture supernatant and then infecting the insect cell with the recombinant virus.

Examples of the gene transfer vector to be used in this method include pVL1392, pVL1393, pBlueBacIII (all manufactured by Invitrogen).

Examples of the baculovirus include *Autographa californica* nuclear polyhedrosis virus with which insects of the family Barathra are infected and the like.

Examples of the insect cells include *Spodoptera frugiperda oocyte, Trichoplusia ni oocyte, Bombyx mori* oocyte-derived culturing cell and the like.

The *Spodoptera frugiperda* oocytes include Sf9 and Sf21 (*Baculovirus Expression Vectors, A Laboratory Manual*) and the like. The *Trichoplusia ni* oocytes include High 5, BTI-TN-5B1-4 (manufactured by Invitrogen) and the like. The *Bombyx mori* oocyte culture cells include *Bombyx mori* N4 and the like.

Examples of the method for the simultaneous cotransfection of the above recombinant gene transfer vector and the above baculovirus for the preparation of the recombinant virus include calcium phosphate method (Japanese Published Unexamined Patent Application No. 227075/90), lipofection method [*Proc. Natl. Acad. Sci. USA,* 84, 7413 (1987)] and the like.

Also, DNA can be introduced into insect cells by the same method as that as used for introducing DNA into animal cells. Examples include electroporation method [*Cytotechnology,* 3, 133 (1990)], calcium phosphate method (Japanese Published Unexamined Patent Application No. 227075/90), lipofection method [*Proc. Natl. Acad. Sci. USA,* 84, 7413 (1987)] and the like.

When a plant cell or a plant is used as the host, the polypeptide can be produced in accordance with known methods [*Tissue Culture,* 20 (1994), Tissue Culture 21 (1995), *Trends in Biotechnology,* 15, 45 (1997)].

As the promoter to be used in the gene expression, any promoter can be used, so long as it can function in plant cells. Examples include cauliflower mosaic virus (CaMV) 35S promoter, rice actin 1 promoter and the like. Also, the gene expression efficiency can be improved by inserting intron 1 of corn alcohol dehydrogenase gene or the like between the promoter and the gene to be expressed.

Examples of the host cell include plant cells such as potato, tobacco, corn, rice, rape, soybean, tomato, wheat, barley, rye, alfalfa, flax and the like. As the method for introducing a recombinant vector, any method for introducing DNA into plant cells can be used. Examples include a method using *Agrobacterium* (Japanese Published Unexamined Patent Application No. 140885/84, Japanese Published Unexamined Patent Application No. 70080/85, WO 94/00977), electroporation method [*Cytotechnology,* 3, 133 (1990), Japanese Published Unexamined Patent Application No. 251887/85], a method using a particle gun (gene gun) (Japanese Patent No. 2606856, Japanese Patent No. 2517813) and the like.

A cell or organ of the gene-introduced plant can be cultured in a large amount by using a jar fermentor. Also, a gene-introduced plant (transgenic plant) can be constructed by re-differentiating the gene-introduced plant cell.

The polypeptide of the present invention can also be produced by using an animal. For example, the polypeptide of the present invention can be produced in a gene-introduced animal in accordance with known methods [*American Journal of Clinical Nutrition,* 63, 639S (1996), *American Journal of Clinical Nutrition,* 63, 627S (1996), *Bio/Technology,* 9, 830 (1991)].

Any promoter which can be expressed in an animal can be used, for example, mammary gland cell-specific promoters such as α-casein promoter, β-lactoglobulin promoter, whey acidic protein promoter and the like are suitably used.

The polypeptide of the present invention can be produced by culturing a transformant derived from a microorganism, animal cell or plant cell having a recombinant vector into which a DNA encoding the polypeptide is inserted, in accordance with a general culturing method, to thereby produce and accumulate the polypeptide, and then recovering the polypeptide from the resulting culture mixture.

When the transformant is an animal or plant, the polypeptide can be produced by rearing or cultivating it in accordance with a general rearing or cultivating method to thereby produce and accumulate the polypeptide, and then recovering the polypeptide from the animal or plant.

That is, in an animal, the polypeptide having the novel β1,3-N-acetylglucosaminyltransferase activity can be obtained by, for example, rearing a non-human transgenic animal retaining the DNA of the present invention to thereby produce and accumulate the polypeptide having the novel β1,3-N-acetylglucosaminyltransferase activity encoded by the recombinant DNA, in the animal, and then recovering the polypeptide from the animal. Examples of the production and accumulation region in the animal include milk, eggs and the like.

In a plant, the polypeptide having the novel β1,3-N-acetylglucosaminyltransferase activity can be obtained by, for example, cultivating a transgenic plant having the DNA of the present invention to thereby produce and accumulate the polypeptide having the novel β1,3-N-acetylglucosaminyltransferase activity encoded by the recombinant DNA, in the plant, and then recovering the polypeptide from the plant.

When the transformant for use in the production of the polypeptide of the present invention is prokaryote such as *Escherichia coli* or the like, or eukaryote such as yeast or the like, the medium for culturing such an organism may be either a natural medium or a synthetic medium, so long as it contains carbon sources, nitrogen sources, inorganic salts and the like which can be assimilated by the organism and can be used for the efficient culture of the transformant.

The carbon sources include those which can be assimilated by the transformant. Examples include carbohydrates such as glucose, fructose, sucrose, molasses containing them, starch, starch hydrolysate and the like; organic acids such as acetic acid, propionic acid and the like; alcohols such as ethanol, propanol and the like.

Examples of the nitrogen sources include ammonia, various ammonium salts of inorganic acids and organic acids such as ammonium chloride, ammonium sulfate, ammonium acetate, ammonium phosphate and the like; other nitrogen-containing compounds, as well as peptone, meat extract, yeast extract, corn steep liquor, casein hydrolysate, soybean meal and soybean meal hydrolysate and various fermented cells and hydrolysates thereof.

Examples of the inorganic sals include potassium dihydrogen phosphate, dipotassium hydrogen phosphate, magnesium phosphate, magnesium sulfate, sodium chloride, ferrous sulfate, manganese sulfate, copper sulfate, calcium carbonate and the like.

Culturing is carried out under aerobic condition such as shaking culture, submerged spinner culture under aeration or the like. The culturing temperature is preferably from 15 to 40° C., and the culturing time is generally from 16 to 96 hours. During culturing, the pH is controlled at 3.0 to 9.0. The pH is adjusted using an inorganic or organic acid, an alkali solution, urea, calcium carbonate, ammonia and the like.

If necessary, antibiotics such as ampicillin, tetracycline and the like may be added to the medium during culturing.

When a microorganism transformed with an expression vector obtained using an inducible promoter as the promoter is cultured, an inducer may be added to the medium, if necessary. For example, isopropyl-β-D-thiogalactopyranoside (IPTG) or the like may be added to the medium when a microorganism transformed with an expression vector obtained using lac promoter is cultured, or indoleacrylic acid (IAA) or the like may be added to the medium when a microorganism transformed with an expression vector obtained by using trp promoter is cultured.

When the transformant for use in the production of the polypeptide of the present invention is an animal cell, generally-used media such as RPMI 1640 medium [*The Journal of the American Medical Association,* 199, 519 (1967)], Eagle's MEM medium [*Science,* 122, 501 (1952)], DMEM medium [*Virology,* 8, 396 (1959)], 199 Medium [*Proceeding of the Society for the Biological Medicine,* 73, 1 (1950)] or any one of these media further supplemented with fetal calf serum or the like can be used.

Culturing is carried out generally at pH 6 to 8 and at 30 to 40° C. in the presence of 5% $CO_2$ for 1 to 7 days. If necessary, antibiotics such as kanamycin, penicillin and the like may be added to the medium during culturing.

Regarding the medium for use in culturing of a transformant obtained using an insect cell as the host, usually used TNM-FH medium (manufactured by PharMingen), Sf-900 II SFM medium (manufactured by GIBCO BRL), ExCell 400 or ExCell 405 (both manufactured by JRH Biosciences), Grace's Insect Medium [*Nature,* 195, 788 (1962)] or the like can be used.

Culturing is carried out at pH 6 to 7 and at 25 to 30° C. for 1 to 5 days. In addition, antibiotics such as gentamicin and the like may be added to the medium during culturing, if necessary.

Regarding the method for expression of the gene, in addition to the case of expressing the full-length polypeptide, it can also be expressed as a partial polypeptide containing a region having the β1,3-N-acetylglucosaminyltransferase activity. In general, a glycosyltransferase has the topology of type II membrane protein and comprises an N-terminal cytoplasmic region containing several to several ten amino acids, a membrane-binding region having a highly hydrophobic amino acid sequence, a stem region containing several to several ten amino acids and the remaining C-terminal part comprising most of the polypeptide and containing a catalytic region. It is considered that the stem region and the remaining C-terminal part comprising most of the polypeptide and containing a catalytic region are exposed to the Golgi body cavity. The boundary between the stem region and catalytic region can be experimentally examined by preparing an N-terminus-deleted polypeptide and examining the degree of the deletion by which the activity disappears. On the other hand, the amino acid sequence of the stem region and catalytic region can be presumed by comparing with that of a similar glycosyltransferase having information on the stem region and catalytic region.

As for the novel β1,3-N-acetylglucosaminyltransferase of the present invention, it was presumed that the polypeptide having the amino acid sequence represented by SEQ ID NO:1 comprises an N-terminal cytoplasmic region containing 9 amino acids, a subsequent membrane-binding region rich in hydrophobic nature containing 19 amino acids, a stem region containing at least 12 amino acids and the remaining C-terminal part comprising most of the polypeptide and containing a catalytic region, each of the polypeptides having the amino acid sequences represented by SEQ ID NOS:2 and 3 comprises an N-terminal cytoplasmic region containing 11 amino acids, a subsequent membrane-binding region rich in hydrophobic nature containing 21 amino acids, a stem region containing at least 12 amino acids and the remaining C-terminal part comprising most of the polypeptide and containing a catalytic region, and the polypeptide having the amino acid sequence represented by SEQ ID NO:4 comprises an N-terminal cytoplasmic tail region containing 29 amino acids, a subsequent membrane-binding region rich in hydrophobic nature containing 20 amino acids, a stem region containing at least 12 amino acids and the remaining C-terminal part comprising most of the polypeptide and containing a catalytic region.

The stem region was presumed based on the comparison of the homology of the amino acid sequence with those of other β1,3-N-acetylglucosaminyltransferases and a β1,3-galactosyltransferase, and the information on the stem regions of other β1,3-N-acetylglucosaminyltransferases and a β1,3-galactosyltransferase (Example 4 in this specification, Japanese Published Unexamined Patent Application No. 181759/94).

Accordingly, it is considered that a polypeptide containing an amino acid sequence of positions 41-397 of SEQ ID NO:1, polypeptides containing an amino acid sequence of positions 45-372 of SEQ ID NOS:2 and 3 and a polypeptide containing an amino acid sequence of positions 62-378 of SEQ ID NO:4 contain catalytic regions.

In addition to its direct expression, the above full-length polypeptide or partial polypeptide containing a region having a β1,3-N-acetylglucosaminyltransferase activity (catalytic region) can also be expressed as a secreted protein or a fusion protein in accordance with the method described in *Molecular Cloning,* 2nd Ed. or the like. Examples of the protein to be fused include β-galactosidase, protein A, IgG binding region of protein A, chloramphenicol acetyltransferase, poly(Arg), poly(Glu), protein G, maltose-binding protein, glutathione S-transferase, polyhistidine chain (His-tag), S peptide, DNA binding protein domain, Tac antigen, thioredoxin, green fluorescent protein, FLAG peptide, epitopes of antibodies of interest and the like [*Jikken Igaku,* 13, 469 (1995)].

When the polypeptide of the present invention is produced in a host cell or on the outer membrane of a host cell, the polypeptide can be positively secreted extracellularly in accordance with the method of Poulson et al. [*J. Biol. Chem.,* 264, 17619 (1989)], the method of Lowe et al. [*Proc. Natl. Acad. Sci. USA,* 86, 8227 (1989), *Genes Develop.,* 4, 1288 (1990)], or the methods described in Japanese Published Unexamined Patent Application No. 336963/93, WO 94/23021 and the like.

That is, the polypeptide of the present invention can be positively secreted by expressing it in a form in which a signal peptide is added to the upstream of a polypeptide containing an active region of the polypeptide of the present invention, in accordance with recombinant DNA techniques.

Specifically, it is considered that the polypeptide of the present invention can be positively secreted extracellulary by adding a signal peptide to the upstream of a polypeptide having an amino acid sequence presumably containing a catalytic region and expressing the product. In addition, a tag for use in the purification and detection can be added between the signal peptide and the catalytic region, or to the C-terminus of a polypeptide containing the catalytic region.

Examples of the tag for use in the purification and detection include β-galactosidase, protein A, IgG binding region of protein A, chloramphenicol acetyltransferase, poly(Arg), poly(Glu), protein G, maltose-binding protein, glutathione S-transferase, polyhistidine chain (His-tag), S peptide, DNA binding protein domain, Tac antigen, thioredoxin, green fluorescent protein, FLAG peptide, epitopes of antibodies of interest and the like [A. Yamakawa, *Jikken Igaku,* 13, 469-474 (1995)].

In addition, its production can be increased in accordance with the method described in Japanese Published Unexamined Patent Application No. 227075/90 using a gene amplification system in which a dihydrofolate reductase gene or the like is used.

General methods for isolation and purification of enzymes can be used for isolating and purifying the polypeptide of the present invention from a culture of a transformant for use in the production of the polypeptide of the present invention. For example, when the polypeptide of the present invention is accumulated in a soluble form inside the cells of the transformant for use in the production of the polypeptide of the present invention, the cells in the culture are collected by centrifugation, the cells are washed and then the cells are disrupted by using ultrasonic oscillator, French press, Manton Gaulin homogenizer, dynomill or the like to obtain a cell-free extract.

A purified product can be obtained from a supernatant prepared by centrifuging the cell-free extract, by employing techniques, such as solvent extraction; salting out and desalting with ammonium sulfate or the like; precipitation with organic solvents; anion exchange chromatography which uses a resin such as diethylaminoethyl (DEAE)-Sepharose, DIAION HPA-75 (manufactured by Mitsubishi Chemical), etc.; cation exchange chromatography in which a resin such as S-Sepharose FF is used (manufactured by Pharmacia), etc.; hydrophobic chromatography in which a resin such as butyl-Sepharose, phenyl-Sepharose, etc. is used; gel filtration in which a molecular sieve is used; affinity chromatography; chromatofocusing; electrophoresis such as isoelectric focusing, etc.; and the like.

Also, when the polypeptide is expressed as an inclusion body in the cells, the cells are recovered, disrupted and centrifuged in the same manner, the polypeptide is recovered from the thus obtained precipitated fraction in the usual manner and then the inclusion body of the polypeptide is solubilized by using a polypeptide denaturing agent. The polypeptide is made into normal tertiary structure by diluting or dialyzing the solubilized solution in or against a solution which does not contain the polypeptide denaturing agent or contains the polypeptide denaturing agent but in such a low concentration that the protein is not denatured, and then its purified product is obtained by the above isolation and purification method.

When the polypeptide is secreted extracellularly, the culture is treated by centrifugation or the like means to obtain a soluble fraction. A purified preparation of the polypeptide can be obtained from the soluble fraction by a method similar to the above method for its isolation and purification from a cell-free extract supernatant.

Alternatively, the polypeptide can be purified in accordance with the general purification method of glycosyltransferases [*Methods in Enzymology,* 83, 458].

Also, the polypeptide of the present invention can be purified by producing it as a fusion protein with other protein and then treating the product with affinity chromatography in which a substance having affinity for the fused protein is used. For example, the polypeptide of the present invention can be purified by producing it as a fusion protein with protein A and then treating the fusion protein with an affinity chromatography in which immunoglobulin G is used, in accordance with the method of Lowe et al. [*Proc. Natl. Acad. Sci. USA,* 86, 8227 (1989), *Genes Develop.,* 4, 1288 (1990)] or the method described in Japanese Published Unexamined Patent Application No. 336963/93 or WO 94/23021. Also, the polypeptide of the present invention can be purified by producing it as a fusion protein with FLAG peptide and then treating the product with an affinity chromatography in which anti-FLAG antibody is used [*Proc. Natl. Acad. Sci. USA,* 86, 8227 (1989), *Genes Develop.,* 4, 1288 (1990)].

In addition, it can also be purified by affinity chromatography in which an antibody for the polypeptide itself is used.

Also, the β1,3-N-acetylglucosaminyltransferase of the present invention can be produced in accordance with known method [*J. Biomolecular NMR,* 6, 129-134, *Science,* 242, 1162, *J. Biochem.,* 110, 166 (1991)] by using an in vitro transcription translation system.

In addition, the polypeptide of the present invention can also be produced by the chemical synthesis method such as Fmoc method (fluorenylmethyloxycarbonyl method), tBoc method (t-butyloxycarbonyl method) and the like. Also, it can be chemically synthesized using a peptide synthesizing machine manufactured, e.g., by Advanced ChemTech, PER- KIN ELMER, Pharmacia Biotech, Protein Technology Instrument, Synthecell-Vega, PerSeptive, Shimadzu or the like.

The purified polypeptide of the present invention can be structurally analyzed in the method generally used in protein chemistry, such as the method described in *Protein Structure Analysis for Gene Cloning* (edited by H. Hirano, published by Tokyo Kagaku Dojin, 1993).

A β1,3-N-acetylglucosaminyltransferase activity of the novel polypeptide of the present invention can be measured in accordance with known measuring methods [*J. Biol. Chem.,* 268, 27118 (1993), *J. Biol. Chem.,* 267, 2994 (1992), *J. Biol. Chem.,* 263, 12461 (1988), *Jpn. J. Med. Sci. Biol.,* 42, 77 (1898)].

A β1,3-galactosyltransferase activity of the polypeptide of the present invention can be measured in accordance with known measuring methods [*J. Biol. Chem.,* 258, 9893 (1983), *J. Biol. Chem.,* 262, 15649 (1987), *Archi. Biochem. Biophys.,* 270, 630 (1989), *Archi. Biochem. Biophys.,* 274, 14 (1989), Japanese Published Unexamined Patent Application No. 181759/94, *J. Biol. Chem.,* 273, 58 (1998), *J. Biol. Chem.,* 273, 433 (1998), *J. Biol. Chem.,* 273, 12770 (1998), *J. Biol. Chem.,* 274, 12499 (1999)].

(4) Production of a Sugar Chain Having a Structure in which N-Acetylglucosamine is Added to a Galactose Residue Via a β1,3-Linkage and Production of a Complex Carbohydrate Containing the Sugar Chain Sugar chains or complex carbohydrates can be produced by culturing a transformant selected from the transformants derived from microorganisms, animal cells, plant cells and insect cells, obtained in the above (3), in a medium to produce and accumulate a sugar chain having a structure in which N-acetylglucosamine is added to a galactose residue via a β1,3-linkage or a complex carbohydrate containing the sugar chain, in the culture, and then recovering the sugar chain or complex carbohydrate from the culture.

Examples of the structure in which N-acetylglucosamine is added to a galactose residue via a β1,3-linkage include a GlcNAcβ1-3Galβ1-4GlcNAc structure, a GlcNAcβ1-3Galβ1-3GlcNAc structure, a GlcNAcβ1-3Galβ1-4Glc structure, a $(Gal\beta1\text{-}4GlcNAc\beta1\text{-}3)_n$Galβ1-4GlcNAc structure (n≥1), a $(Gal\beta1\text{-}4GlcNA\beta1\text{-}3)_n$Galβ1-4Glc structure (n≥1) or the like.

The culturing of the transformants can be carried out in accordance with the above (3), Among the above transformants, by simultaneously producing the polypeptide of the present invention and an recombinant glycoprotein of interest (e.g., a recombinant glycoprotein for medical use) in a transformant capable of synthesizing sugar chains, a sugar chain having a structure in which N-acetylglucosamine is added to a galactose residue via a β1,3-linkage can be added to the recombinant glycoprotein.

Also, a sugar chain having a structure in which N-acetylglucosamine is added to a galactose residue via a β1,3-linkage or a complex carbohydrate to which the sugar chain is added can be produced in accordance with the method of the above (3) by using an animal or plant obtained in the above (3).

That is, in an animal, a sugar chain having a structure in which N-acetylglucosamine is added to a galactose residue via a β1,3-linkage or a complex carbohydrate to which the sugar chain is added can be produced by, for example, rearing a non-human transgenic animal retaining the DNA of the present invention to thereby produce and accumulate the sugar chain having a structure in which N-acetylglucosamine is added to a galactose residue via a β1,3-linkage or a complex carbohydrate to which the sugar chain is added, in the animal, and then recovering the product from the animal.

Examples of the production and accumulation region in the animal include milk, eggs and the like of the animal.

In a plant, a sugar chain having a structure in which N-acetylglucosamine is added to a galactose residue via a β1,3-linkage or a complex carbohydrate to which the sugar chain is added can be produced by, for example, cultivating a transgenic plant having the DNA of the present invention to produce and accumulate the sugar chain having a structure in which N-acetylglucosamine is added to a galactose residue via a β1,3-linkage or a complex carbohydrate to which the sugar chain is added, in the plant, and then recovering the product from the plant.

A reaction product in which N-acetylglucosamine is added to a galactose residue existing at the non-reducing end of a sugar chain or galactose monosaccharide via a β1,3-linkage can be produced in the following method, in an aqueous medium by using the polypeptide of the present invention obtained by the method described in the above (3) as an enzyme source.

That is, the reaction product can be produced by using galactose monosaccharide, an oligosaccharide having a galactose residue at its non-reducing terminal or a complex carbohydrate having a galactose residue at the non-reducing terminal of its sugar chain as an acceptor substrate and by using the polypeptide of the present invention obtained by the method described in the above (3) as an enzyme source, by allowing the acceptor substrate, the enzyme source and UDP-GlcNAc to be present in an aqueous medium to thereby produce and accumulate a reaction product in which N-acetylglucosamine is added to galactose or a galactose residue of the acceptor substrate via a β1,3-linkage, in the aqueous medium, and then recovering the reaction product from the aqueous medium.

When the activity capable of producing 1 μmol of GlcNAcβ1-3Galβ1-4GlcNAcβ1-3Galβ1-4Glc within 1 minute at 37° C. using lacto-N-neotetraose (Galβ1-4GlcNAcβ1-3Galβ1-4Glc) as a substrate is defined as one unit (U), the enzyme source is used at a concentration of 0.1 mU/l to 10,000 U/l, preferably 1 mU/l to 1,000 U/l.

Examples of the aqueous medium include a buffer such as water, phosphate, carbonate, acetate, borate, citrate, tris, etc.; alcohol such as methanol, ethanol, etc.; ester such as ethyl acetate, etc.; ketone such as acetone, etc.; amide such as acetamide, etc.; and the like. In addition, the culture of a transformant obtained by the culturing described in the above (2) or the milk obtained from a non-human transgenic animal described in the above (2) can also be used as an aqueous medium. If necessary, a surfactant or an organic solvent may be added to the aqueous medium.

The surfactant may be any agent which can accelerate the production of a sugar chain having a structure in which N-acetylglucosamine is added to a galactose residue via a β1,3-linkage or a complex carbohydrate to which the sugar chain is added. Examples include a nonionic surfactant such as polyoxyethylene octadecylamine (e.g., Nymeen S-215, manufactured by Nippon Oil & Fats), etc.; a cationic surfactant such as cetyltrimethylammonium bromide, alkyldimethyl benzylammoniumchloride (e.g., Cation F2-40E, manufactured by Nippon Oil & Fats), etc.; an anionic surfactant such as lauroyl sarcosinate, etc.; tertiary amine such as alkyldimethylamine (e.g., Tertiary Amine FB, manufactured by Nippon Oil & Fats), etc.; and the like, which may be used alone or as a mixture of two or more. The surfactant is used generally at a concentration of 0.1 to 50 g/l.

Examples of the organic solvent include xylene, toluene, aliphatic alcohol, acetone, ethyl acetate and the like, which are used generally at a concentration of 0.1 to 50 ml/l.

Examples of the UDP-GlcNAc include a commercially available preparation, a reaction solution made by using the activity of a microorganism or the like, and a preparation purified from the reaction solution. UDP-GlcNAc can be used at a concentration of 0.1 to 500 mmol/l.

Examples of the oligosaccharide having a galactose residue at its non-reducing terminal include Galβ1-4Glc, Galβ1-4GlcNAc, Galβ1-4GlcNAcβ1-3Galβ1-4Glc, Galβ1-4GlcNAcβ1-3Galβ1-4GlcNAc, Galβ1-4(Fucα1-3)GlcNAβ1-3Galβ1-4Glc, Galβ1-4(Fucα1-3)GlcNAβ1-3Galβ1-4GlcNAc, Galβ1-4GlcNAβ1-3Galβ1-4(Fucα1-3)Glc, Galβ1-4GlcNAcβ1-3Galβ1-4(Fucα1-3)GlcNAc, Galβ1-3GlcNAc, Galβ1-3GlcNAcβ1-3Galβ1-4Glc, Galβ1-3GlcNAβ1-3Galβ1-4GlcNAc, Galβ1-3GlcNAβ1-3Galβ1-4(Fucα1-3)Glc, Galβ1-3GlcNAβ1-3Galβ1-4(Fucα1-3)GlcNAc, Galβ1-4GlcNAβ1-3(GlcNAβ1-6)Galβ1-4Glc, Galβ1-4GlcNAβ1-3(GlcNAβ1-6)Galβ1-4GlcNAc, Galβ1-4GlcNAβ1-3(Galβ1-4GlcNAβ1-6)Galβ1-4Glc, Galβ1-4GlcNAβ1-3(Galβ1-4GlcNAβ1-6)Galβ1-4GlcNAc, Galβ1-3GlcNAβ1-3(GlcNAβ1-6)Galβ1-4Glc, Galβ1-3GlcNAβ1-3(GlcNAβ1-6)Galβ1-4GlcNAc, Galβ1-3GlcNAβ1-3(Galβ1-4GlcNAβ1-6)Galβ1-4Glc and Galβ1-3GlcNAβ1-3(Galβ1-4GlcNAβ1-6)Galβ1-4GlcNAc, or an oligosaccharide having any one of the structures of these oligosaccharides at the non-reducing terminal of its sugar chain. Examples of the complex carbohydrate having a galactose residue at the non-reducing terminal of its sugar chain include a complex carbohydrate containing a sugar chain having any one of the structures of the above oligosaccharides at the non-reducing terminal of the sugar chain, a complex carbohydrate containing an asialo complex N-linked sugar chain and the like.

The acceptor substrate can be used at a concentration of 0.01 to 500 mmol/l.

If necessary, an inorganic salt such as $MnCl_2$, etc., β-mercaptoethanol, polyethylene glycol and the like can be added in the production reaction.

The production reaction is carried out at pH 5 to 10, preferably pH 6 to 8, and at 20 to 50° C. for 1 to 96 hours.

A part of a sugar chain can be recovered from the sugar chain or complex carbohydrate produced by the above method by the known enzymatic method or the chemical method [*Second Series Biochemical Experiment Course*, Vol. 4, Methods for Complex Carbohydrate Experiments I, II, edited by Japanese Biochemical Society, Tokyo Kagaku Dojin (1986); *Glycobiology Experiment Protocol*, edited by N. Taniguchi, A. Suzuki, K. Furukawa and K. Sugawara, Shujun-sha (1996)].

(5) Use of the DNA or Oligonucleotide of the Present Invention for Treatment, Diagnosis and the Like of Diseases The DNA of the present invention can be used in the treatment of diseases, such as inhibition of inflammation and metastasis, in accordance with antisense RNA/DNA technique [*Bioscience and Industry,* 50, 322 (1992), Chemistry, 46, 681 (1991), *Biotechnology,* 9, 358 (1992), *Trends in Biotechnology,* 10, 87 (1992), *Trends in Biotechnology,* 10, 152 (1992), *Cell Engineering,* 16, 1463 (1997)] or triple helix technique [*Trends in Biotechnology,* 10, 132 (1992)].

Also, inflammation and cancer can be diagnosed by measuring the expression level of the DNA of the present invention in the Northern hybridization method (*Molecular Cloning,* 2nd Ed.), PCR method [*PCR Protocols*, Academic Press (1990)] or real time PCR method [*Jikken Igaku* (Supplement), 15, 46 (1997)]. Particularly, quantitative PCR method [*Proc. Natl. Acad. Sci. USA,* 87, 2725 (1990)] and real time PCR method are excellent in determination property. For example, production of the polypeptide of the present invention can be inhibited by administering the DNA or oligonucleotide of the present invention or a derivative thereof.

That is, it is possible to inhibit transcription of the DNA encoding the polypeptide of the present invention or to inhibit translation of mRNAs encoding the polypeptide of the present invention, by using the DNA or oligonucleotide of the present invention or a derivative thereof described in the above (1).

Also, the expression level of the DNA encoding the polypeptide of the present invention can be determined in the Northern hybridization method or PCR method by using the DNA of the present invention or the oligonucleotide prepared from the DNA.

In addition, it is possible to obtain a promoter region of the gene in the known method [*New Cell Engineering Experiment Protocol*, edited by Anticancer Study Division, Institute of Medical Science, Tokyo University, Shujun-sha (1993)] using the DNA of the present invention as a probe.

Currently, a large number of sequences of function-unknown human chromosomal genes are registered for data bases. Accordingly, there is a possibility that a human chromosomal gene encoding the polypeptide of the present invention can be identified and its structure can be found, by comparing a human cDNA sequence encoding the polypeptide of the present invention with sequences of human chromosomal genes registered for data bases. When a chromosomal gene sequence identical to the cDNA sequence is registered, promoter region, exon and intron structures of the chromosomal gene encoding the polypeptide of the present invention can be determined by comparing the cDNA sequence with the chromosomal gene sequence.

Examples of the promoter region include all promoter regions which is involved in the transcription of the gene encoding the polypeptide of the present invention in mammalian cells. Specific examples include promoter regions which take part in the transcription of the gene encoding the polypeptide of the present invention in human leukocytes, human colon cancer cells and human pancreatic cancer cells.

It is known that polymorphism and mutation exist in the glycosyltransferase genes. For example, regarding the glycosyltransferase involved in the determination of ABO blood type, the following three kinds of enzymes are formed due to differences in amino acid sequences based on the genetic polymorphism: an α1,3-N-acetylgalactosamine transferase involved in the synthesis of type A antigen, an α1,3-galactosyltransferase involved in the synthesis of type B antigen, and an enzyme which has no activity and is involved in the production of type O (H) sugar chain [*Nature,* 345, 229-233 (1990)].

Also, in α1,3-fucosyltransferase (Fuc-T III) which is involved in the determination of Lewis blood group, it is known that enzymes whose activity is reduced or deleted are formed due to differences in amino acid sequences based on the gene polymorphism [*J. Biol. Chem.,* 269, 29271 (1994), *Blood,* 82, 2915 (1993), *J. Biol. Chem.,* 269, 20987 (1994), *J. Biol. Chem.,* 272, 21994 (1997)].

It is known that polymorphism of the Fuc-T III gene has a close relation to the expression of sialyl Lewis a sugar chain which is a cancer-related sugar chain antigen in colon cancer [*Cancer Res.,* 56, 330 (1996), *Cancer Res.,* 58, 512 (1998)].

Accordingly, it is considered that diagnosis of diseases and prediction of prognosis can be carried out by examining polymorphism of Fuc-T III.

Since the novel β1,3-N-acetylglucosaminyltransferase of the present invention is involved in the synthesis of poly-N- acetyllactosamine, it is considered that it is involved in the synthesis of sialyl Lewis x sugar chain in leukocyte and cancer-related sugar chains (sialyl Lewis x sugar chain, sialyl Lewis a sugar chain, sialyl Lewis c sugar chain, dimeric Lewis a sugar chain) in cancer cells. Accordingly, it is considered that diagnosis of inflammation, cancer or metastasis, or prediction of prognosis cancer can be carried out by examining the expression level and polymorphism of the gene.

Also, it can be used in the diagnosis of other diseases by examining the relationship between the polymorphism of the gene and the diseases in organs where the gene is expressed.

The polymorphism of the gene can be analyzed by using gene sequence information of the gene. Specifically, the gene polymorphism can be analyzed in accordance with Southern blot technique, direct sequencing method, PCR method, DNA chip method and the like [*Rinsho Kensa,* 42, 1507 (1998), *Rinsho Kensa,* 42, 1565 (1998)].

(6) Production of an Antibody Capable of Recognizing the Polypeptide of the Present Invention (i) Production of a Polyclonal Antibody A polyclonal antibody can be produced by using the purified sample of the full length or a partial fragment of the polypeptide obtained by the method of the above (3) or a peptide having an amino acid of a part of the protein of the present invention as an antigen and administering it to an animal.

Rabbits, goats, 3- to 20-week-old rats, mice, hamsters and the like can be used as the animal to be administered. It is preferred that the dose of the antigen is 50 to 100 μg per one animal.

When a peptide is used as an antigen, it is preferred to use the peptide as an antigen after binding it to keyhole limpet haemocyanin, bovine thyroglobulin or the like carrier protein by a covalent bond. The peptide to be used as an antigen can be synthesized using a peptide synthesizer.

The antigen is administered 3 to 10 times at one- to two-week intervals after the first administration. Three to seven days after each administration, a blood sample is collected from the venous plexus of the fundus of the eye, and the serum is tested by enzyme immunoassay [*Enzyme-linked Immunosorbent Assay* (*ELISA*): published by Igaku Shoin, (1976), *Antibodies—A Laboratory Manual*, Cold Spring Harbor Laboratory (1988)] and the like as to whether it is reactive with the antigen used for immunization.

A polyclonal antibody can be obtained by collecting a serum sample from non-human mammal in which the serum showed a sufficient antibody titer against the antigen used for immunization, and separating and purifying the serum.

Examples of the method for its separation and purification include centrifugation, salting out with 40 to 50% saturated ammonium sulfate, caprylic acid precipitation [*Antibodies—A Laboratory Manual*, Cold Spring Harbor Laboratory (1988)] and chromatography using a DEAE-Sepharose column, an anion exchange column, a protein A- or G-column, a gel filtration column or the like, which may be used alone or in combination.

(ii) Production of a Monoclonal Antibody (a) Preparation of Antibody Producing Cells A rat whose serum showed a sufficient antibody titer against the partial fragment of the polypeptide of the present invention used in the immunization is used as the supply source of antibody producing cells.

Three to seven days after the final administration of the antigen substance to the rat which showed the antibody titer, the spleen is excised. The spleen is cut to pieces in MEM medium (manufactured by Nissui Pharmaceutical), and cells are unbound using a pair of forceps and centrifuged at 1,200 rpm for 5 minutes and then the supernatant is discarded.

Splenocytes in the thus obtained precipitation fraction are treated with a Tris-ammonium chloride buffer (pH 7.65) for 1 to 2 minutes for eliminating erythrocytes and then washed three times with MEM medium, and the thus obtained splenocytes are used as an antibody producing cells.

(b) Preparation of Myeloma Cells

As the myeloma cells, established cell lines obtained from mouse or rat are used.

Examples include 8-azaguanine-resistant mouse (BALB/c-derived) myeloma cell lines P3-X63Ag8-U1 (hereinafter referred to as "P3-U1") [*Curr. Topics Microbiol. Immunol.,* 81, 1 (1978), *Eur. J. Immunol.,* 6, 511 (1976)], SP2/O-Ag14 (SP-2) [*Nature,* 276, 269 (1978)], P3-X63-Ag8653 (653) [*J. Immunol.,* 123, 1548 (1979)], P3-X63-Ag8 (X63) [*Nature,* 256, 495 (1975)] and the like.

The cell lines are subcultured in an 8-azaguanine medium [prepared by supplementing RPMI-1640 medium with glutamine (1.5 mmol/l), 2-mercaptoethanol ($5\times10^{-5}$ mol/l), gentamicin (10 μg/ml) and fetal calf serum (FCS) (manufactured by CSL, 10%) and further supplementing the resulting medium (hereinafter referred to as "normal medium") with 8-azaguanine (15 μg/ml)], and they are cultured in the normal medium 3 to 4 days before the cell fusion, and $2\times10^{7}$ or more of the cells are used for the cell fusion.

(c) Preparation of a Hybridoma

The antibody producing cells obtained in (a) and the myeloma cells obtained in (b) are washed thoroughly with MEM medium or PBS (1.83 g of disodium hydrogenphosphate, 0.21 g of potassium dihydrogenphosphate and 7.65 g of sodium chloride, 1 liter of distilled water, pH 7.2) and mixed in a proportion of antibody producing cells:myeloma cells=5 to 10:1, and the mixture is centrifuged at 1,200 rpm for 5 minutes and then the supernatant is discarded.

Cells in the thus obtained precipitation fraction are thoroughly loosened, and a mixture of 2 g of polyethylene glycol-1000 PEG-1000), 2 ml of MEM and 0.7 ml of dimethyl sulfoxide (DMSO) is added to the cells in an amount of 0.2 to 1 ml per $10^{8}$ antibody producing cells under stirring at 37° C., and then 1 to 2 ml of MEM medium is added several times at 1 to 2 minute intervals. After the addition, the whole volume is adjusted to 50 ml by adding MEM medium.

After centrifugation of the thus prepared solution at 900 rpm for 5 minutes, the supernatant is discarded.

Cells in the thus obtained precipitation fraction are gently loosened and then suspended in 100 ml of HAT medium [prepared by supplementing the normal medium with hypoxanthine ($10^{-4}$ mol/l), thymidine ($1.5\times10^{-5}$ mol/l) and aminopterin ($4\times10^{-7}$ mol/l)] by repeated drawing up into a measuring pipette and discharging from a measuring pipette.

The suspension is dispensed in 100 μl/well portions into a 96-well culture plate and cultured at 37° C. for 7 to 14 days in a 5% $CO_2$ incubator.

After culturing, a portion of the culture supernatant is taken out and subjected to an enzyme immunoassay described in *Antibodies—A Laboratory Manual*, Cold Spring Harbor Laboratory, Chapter 14 (1988) or the like, and hybridomas which specifically react with the partial fragment polypeptide of the polypeptide of the present invention are selected.

As an example of the enzyme immunoassay, the following method is shown.

The partial fragment of the polypeptide of the present invention used as the antigen in carrying out the immunization is coated on an appropriate plate, allowed to react with a first antibody, namely a hybridoma culture supernatant or the purified antibody obtained in the following (d), further allowed to react with a second antibody, namely an anti-rat or anti-mouse immunoglobulin antibody labeled with biotin, an enzyme, a chemiluminescence substance, a radioactive compound or the like, and then subjected to the reaction corresponding to the label, and those which react specifically with the polypeptide of the present invention are selected as hybridomas that produce the monoclonal antibody for the polypeptide of the present invention.

Using the hybridomas, cloning is repeated twice by limiting dilution using HT medium (a medium prepared by eliminating aminopterin from HAT medium) for the first cloning and the normal medium for the second, and those in which high antibody titer is constantly observed are selected as hybridomas that produce an anti-polypeptide antibody for the polypeptide of the present invention.

(d) Preparation of a Monoclonal Antibody

The hybridoma cells capable of producing a monoclonal antibody for the polypeptide of the present invention obtained in (c) are injected into the abdominal cavity of 8 to 10-week-old mice or nude mice treated with pristane [by intraperitoneal administration of 0.5 ml of 2,6,10,14-tetramethylpentadecane (pristane) followed by 2 weeks of feeding] at a dose of 5 to $20\times10^6$ cells per animal. The hybridoma causes ascites tumor in 10 to 21 days. The ascitic fluid is collected from the ascites tumor-carrying mice and centrifuged at 3,000 rpm for 5 minutes to remove the solid matter.

The monoclonal antibody can be obtained by purifying it from the thus obtained supernatant by the same method used in the purification of a polyclonal antibody.

The subclass of the antibody is determined using a mouse monoclonal antibody typing kit or a rat monoclonal antibody typing kit. The amount of the protein is calculated by the Lowry method or from the absorbance at 280 nm.

(7) Use of the Antibody of the Present Invention (a) The polypeptide of the present invention can be detected by using the antibody of the present invention. Examples of detection methods include the ELISA method by using a microtiter plate, the fluorescent antibody technique, the Western blot technique and the like.

(b) The antibody of the present invention can be used in the immunological staining of cells capable of expressing the polypeptide of the present invention.

(c) The antibody of the present invention can be used in the diagnosis of inflammation and cancer.

(8) Application to Screening Method

Since the novel β1,3-N-acetylglucosaminyltransferase polypeptide of the present invention is involved in the synthesis of a poly-N-acetyllactosamine sugar chain, it is possible to increase or decrease the amount of a poly-N-acetyllactosamine sugar chain which is synthesized in cells, by using a compound capable of increasing or inhibiting the β1,3-N-acetylglucosaminyltransferase activity of the polypeptide.

Also, it is possible to control the amount of a poly-N-acetyllactosamine sugar chain which is synthesized in cells, by controlling the expression of the polypeptide with a compound capable of accelerating or inhibiting transcription process of the gene encoding the polypeptide or translation process of a protein from the transcription product.

Since it is known that a sialyl Lewis x sugar chain and a sialyl Lewis a sugar chain existing on a poly-N-acetyllactosamine sugar chain are ligands for selectin, it is considered that a compound capable of inhibiting the synthesized amount of a poly-N-acetyllactosamine sugar chain is useful for anti-inflammation and metastasis inhibition. On the other hand, it is considered that a compound capable of increasing the synthesis amount of a poly-N-acetyllactosamine sugar chain is useful for the production of a poly-N-acetyllactosamine sugar chain and a complex carbohydrate to which a poly-N-acetyllactosamine sugar chain is added.

Such compounds can be obtained by the methods shown in the following (a) to (e).

(a) By using a polypeptide having the novel β1,3-N-acetylglucosaminyltransferase activity of the present invention, prepared in accordance with the method described in the above (3) (a purified preparation, or a cell extract or culture supernatant of a transformant capable of expressing the polypeptide), as an enzyme and in the presence of a test sample, the β1,3-N-acetylglucosaminyltransferase activity is measured by known methods [*J. Biol. Chem.,* 268, 27118 (1993), *J. Biol. Chem.,* 267, 2994 (1992), *J. Biol. Chem.,* 263, 12461 (1988), *Jpn. J. Med. Sci. Biol.,* 42, 77 (1989)], and a compound which has the activity of increasing or decreasing the β1,3-N-acetylglucosaminyltransferase activity is selected and obtained.

(b) A cell capable of expressing the polypeptide of the present invention or the transformant described in (3) is cultured for 2 hours to 1 week by the culturing method described in (2) in the presence of a test sample, and then the amount of a poly-N-acetyllactosamine sugar chain on the cell surface is measured by using an antibody (anti-i antibody or anti-I antibody) or a lectin (LEA, PWM or DSA), which recognizes the sugar chain to thereby select and obtain a compound which has the activity of increasing or decreasing the sugar chain content.

Examples of the method for measuring using the antibody or lectin include detection methods, such as ELISA method by using a microtiter plate, the fluorescent antibody technique, the Western blot technique, the immunological staining or the like can. It can also be measured by using FACS.

(c) A cell capable of expressing the polypeptide of the present invention is cultured for 2 hours to 1 week by the culturing method described in (2) in the presence of a test sample, and then amount of the polypeptide in the cell is measured using the antibody of the present invention described in (5) to thereby select and obtain a compound which has the activity of increasing or decreasing the polypeptide content.

Examples of the measuring method by using the antibody of the present invention include detection methods, such as ELISA method by using a microtiter plate, the fluorescent antibody technique, the Western blot technique, the immunological staining or the like.

(d) A cell capable of expressing the polypeptide of the present invention is cultured for 2 hours to 1 week by the culturing method described in (2) in the presence of a test sample, and then amount of the transcription product of the gene encoding the polypeptide in the cell is measured by using a method such as the Northern hybridization, PCR or the like described in (4) to thereby select and obtain a compound which has the activity of increasing or decreasing the transcription product content.

(e) A plasmid, which contains a DNA consisting of a reporter gene linked downstream of the promoter obtained in (4), is prepared by the known method and introduced into an animal cell described in (3) in accordance with the methods described in (2) and (3) to obtain a transformant. The transformant is cultured for 2 hours to 1 week by the culturing method described in (2) in the presence of a test sample, and then the expression level of the reporter gene in the cell is measured by known methods [*New Cell Engineering Experiment Protocol*, edited by Anticancer Study Division, Institute of Medical Science, Tokyo University, Shujun-sha (1993), *Biotechniques,* 20, 914 (1996), *J. Antibiotics,* 49, 453 (1996), *Trends in Biochemical Sciences,* 20, 448 (1995), *Cell Engi-*

*neering,* 16, 581 (1997)] to thereby select and obtain a compound which has the activity of increasing or decreasing the expression level.

Examples of the reporter gene include a chloramphenicol acetyltransferase gene, a β-galactosidase gene, a β-lactamase gene, a luciferase gene, a green fluorescent protein (GFP) gene and the like.

(9) Production of a Knockout Animal

By using a vector containing the DNA of the present invention, a mutant clone can be produced in which a DNA encoding the polypeptide of the present invention, existing on the chromosome in embryonic stem cell of the animal of interest such as calf, sheep, goat, pig, horse, domestic fowl, mouse or the like, is inactivated or substituted with an optional sequence [e.g., *Nature,* 350, 6315, 243 (1991)], by the known homologous recombination technique [e.g., *Nature,* 326, 6110, 295 (1987), Cell, 51, 3, 503 (1987) and the like].

By using the thus prepared embryonic stem cell clone, a chimeric individual consisting of the embryonic stem cell clone and normal cell can be prepared by technique such as the injection chimera method, the aggregation chimera method or the like using blastocyst of an animal fertilized egg. An individual having an mutation of interest in the DNA encoding the polypeptide of the present invention, existing on chromosomes of the whole body cells, can be obtained by the crossing of the chimeric individual with normal individual, and a homologous individual (knockout animal) in which the mutation is induced in both of the homologous chromosomes can be obtained by crossing the individuals.

In this way, it is possible to introduce a mutation into a site of interest in the DNA encoding the polypeptide of the present invention existing on chromosome in an animal individual. For example, by introducing mutation, such as nucleotide substitution, deletion, insertion or the like, into the translation region of a chromosomal DNA encoding the polypeptide of the present invention, the activity of the product can be changed.

Also, it is possible to modify the degree and time of expression, tissue specificity and the like by introducing similar mutation into the expression-controlling region. In addition, it is possible to positively control the expression time, expression region, expression level and the like by a combination with Cre-loxP system.

As such examples, an example in which a gene of interest was deleted only in a specified region in the brain using the promoter capable of expressing in the region [*Cell,* 87, 7, 1317 (1996)] and an example in which a gene of interest was deleted organ-specifically at a desired time by using an adenovirus capable of expressing Cre [*Science,* 278, 5335 (1997)] are known.

Accordingly, regarding the chromosomal DNA encoding the polypeptide of the present invention, it is also possible in this manner to prepare an animal controlling its expression at an optional time in an optional tissue, or having an optional insertion, deletion or substitution in its translation region or expression-controlling region.

In such an animal, symptoms of various diseases caused by the polypeptide of the present invention can be induced at an optional time, at an optional degree and in an optional region.

Thus, the knockout animal of the present invention becomes an animal model markedly useful in the treatment and prevention of various diseases caused by the polypeptide of the present invention. Particularly, it is markedly useful as a model for the evaluation of therapeutic drugs and preventive drugs for such diseases and also of functional foods, health foods and the like.

BRIEF DESCRIPTION OF THE DRAWINGS

FIG. 1 is a graph showing a comparison of the nucleotide sequence of positions 1-477 of G4 cDNA with the nucleotide sequence of positions 1-451 of G4-2 cDNA.

FIG. 2 is a graph showing a comparison of the nucleotide sequence of positions 478-1077 of G4 cDNA with the nucleotide sequence of positions 452-1051 of G4-2 cDNA.

FIG. 3 is a graph showing a comparison of the nucleotide sequence of positions 1078-1677 of G4 cDNA with the nucleotide sequence of positions 1052-1651 of G4-2 cDNA.

FIG. 4 is a graph showing a comparison of the nucleotide sequence of positions 1678-2205 of G4 cDNA with the nucleotide sequence of positions 1652-2180 of G4-2 cDNA.

Figure 5:
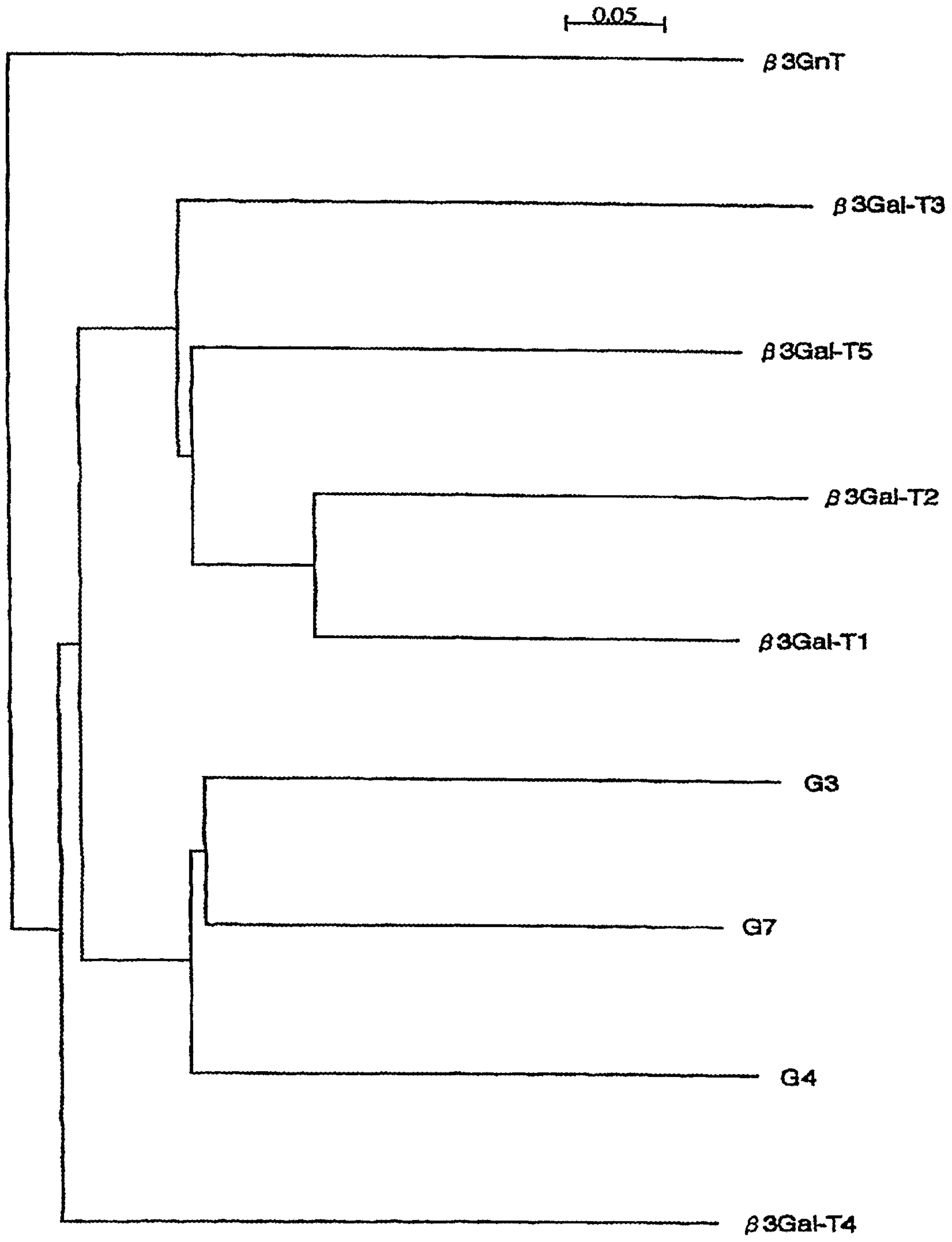
FIG. 5 is a dendrogram showing a comparison of the amino acid sequences of G3, G4, G4-2 and G7 polypeptides, known β1,3-galactosyltransferases (β3Gal-T1, β3Gal-T2, β3Gal-T3, β3Gal-T4, (β3Gal-T5) and a known β1,3-N-acetylglucosaminyltransferase (β3GnT). Only amino acid sequences of regions where homology was found are used and compared. That is, they are compared by excluding cytoplasmic region, membrane-binding region and stem region.

EXPLANATION OF SYMBOLS bp: base pairs
kb: kilobase pairs
G418/Km: transposon 5 (Tn5)-derived G418, kanamycin resistance gene
Ap: pBR322-derived ampicillin resistance gene
Tc: pBR322-derived tetracycline resistance gene
P1: pBR322-derived P1 promoter
Ptk: herpes simplex virus (HSV) thymidine kinase (tk) gene promoter
Sp. BG: rabbit β-globin gene splicing signal
A. BG: rabbit β-globin gene poly(A) addition signal
A. SE: simian virus 40 (SV40) early gene poly(A) addition signal
A. Atk: poly(A) addition signal of the herpes simplex virus (HSV) thymidine kinase (tk) gene
Pmo: long terminal repeat (LTR) promoter of Moloney mouse leukemia virus
EBNA-1: EBNA-1 gene of Epstein-Barr virus
oriP: replication origin of Epstein-Barr virus
S: gene moiety encoding the signal peptide of immunoglobulin K
F: gene moiety encoding FLAG peptide
G3: DNA (full length or partial length) encoding the β1,3-N-acetylglucosaminyltransferase G3 obtained by the present invention
G4: DNA (full length or partial length) encoding the β1,3-N-acetylglucosaminyltransferase G4 or β1,3-N-acetylglucosaminyltransferase G4-2 obtained by the present invention
G7: DNA (full length or partial length) encoding the β1,3-N-acetylglucosaminyltransferase G7 obtained by the present invention

BEST MODE FOR CARRYING OUT THE INVENTION

Examples are shown below. Unless otherwise indicated, known methods described in *Molecular cloning,* 2nd Ed., were used as gene manipulation techniques.

Example 1

Search for a Candidate Gene Having a Possibility of Encoding a Protein Homologous to a GlcNAc β1,3-N-Galactosyltransferase (β3Gal-T1)

The β3Gal-T1 (alias WM1) is a β1,3-galactosyltransferase which is involved in the synthesis of Galβ1-3GlcNAc structure (Japanese Published Unexamined Patent Application No. 181759/94). As a result of the search of a gene having homology with the gene of this enzyme or a gene possibly encoding a protein having homology with this enzyme at the amino acid level based on gene data bases by using the programs of Blast [*J. Mol. Biol.,* 215 (1990)] and FrameSearch (manufactured by Compugen), several EST (expressed sequence tag) sequences were found. Since they were classified into three types based on their sequences, it was considered that three kinds of candidate genes are present. The candidate genes were named G3, G4 and G7, respectively. As the gene data bases, the data base of GenBank and a patented sequence data base GENESEQ (Derwent, Inc.) were used.

An attempt was made to clone fragments of these candidate genes by designing primer sets specific for the above three sequences. As the primer sets, F-3-5 with R-3-5, F-4-5 with R-4-5 and F-7-5a with R-7-3a were used. Sequences of respective primers are shown in SEQ ID NOS:9 to 14.

Example 2

Cloning of a Candidate Gene G3

(1) Cloning of a cDNA Fragment for a Candidate Gene G3

By preparing primers specific for the candidate gene G3 (F-3-5 and R-3-5: their sequences are shown in SEQ ID NOS:9 and 10), PCR was carried out using a single-stranded cDNA prepared from an organ or a cell or a cDNA library as the template, and the presence of cDNA having the corresponding sequence was examined. As a result, a DNA fragment of about 600 bp was amplified when a leukocyte cDNA library (manufactured by Clontech) or a gastric mucosa cDNA library was used as the template. The specific method is shown below.

The leukocyte cDNA library (phage library: manufactured by Clontech) was divided into respective pools of about 40,000 independent clones, and then PCR was carried out using phage particles (about $1\times10^7$) of each pool as the template. After 49.5 μl of a reaction solution [10 mmol/l Tris-HCl (pH 8.3), 50 mmol/l KCl, 1.5 mmol/l $MgCl_2$, 0.2 mmol/l dNTP, 0.001% (w/v) gelatin and 0.2 μmol/l gene-specific primer] containing the phage particles (about $1\times10^7$) which had been treated at 99° C. for 10 minutes was heated at 97° C. for 5 minutes, it was cooled on ice for 5 minutes. Next, recombinant Taq DNA polymerase (manufactured by TaKaRa) was added thereto, and 30 cycles of the reaction using a reaction system constituted by 1 minute at 94° C., 1 minute at 65° C. and 2 minutes at 72° C. as 1 cycle were carried out.

The human gastric mucosa cDNA library was produced as follows. A cDNA library was produced by synthesizing cDNA from human gastric mucosa poly(A) % RNA in the cDNA Synthesis System (manufactured by GIBCO BRL), adding an EcoRI-NotI-SalI adapter (Super Choice System for cDNA Synthesis; manufactured by GIBCO BRL) to its both termini, inserting it into the EcoRI site of a cloning vector λZAPII (λZAPII/EcoRI/CIAP Cloning Kit, manufactured by STRATAGENE) and then carrying out in vitro packaging by using Gigapack III Gold Packaging Extract manufactured by STRATAGENE.

The gastric mucosa cDNA library (phage library) was divided into respective pools of about 50,000 independent clones, and then PCR was carried out by using phage particles (about $1\times10^7$) of each pool as the template. The method was the same as the above method.

The DNA fragment of about 600 bp amplified from a leukocyte cDNA library was inserted into a T-vector pT7Blue (manufactured by Novagen) to construct a plasmid pT7B-G3FR. As a result of the determination of a full nucleotide sequence of a cDNA fragment contained in pT7B-G3FR, it was confirmed that the sequence of the cDNA fragment coincided with one of the EST sequences found in Example 1. For the determination of nucleotide sequence, a DNA sequencer manufactured by LI-COR (dNA sequencer model 4000L), a DNA sequencer 377 manufactured by PERKIN ELMER and a reaction kit for each sequencer were used.

(2) Cloning of a Full-Length cDNA for the Candidate Gene G3

In order to obtain a full-length cDNA for G3, a digoxigenin-labeled probe was produced by PCR DIG probe synthesis Kit (manufactured by Boehringer Mannheim). After 39 μl of a reaction solution containing 1 μg of pT7B-G3FR and 0.2 μmol/l of primers (F-3-5 and R-3-5) was heated at 97° C. for 5 minutes, it was cooled on ice for 5 minutes. Next, 1 unit of recombinant Taq DNA polymerase (manufactured by TaKaRa) was added thereto, and 30 cycles of the reaction using a reaction system constituted by 1 minute at 94° C., 1 minute at 65° C. and 1 minute at 72° C. as 1 cycle were carried out. A composition of the reaction solution was as described in the instructions attached to the kit.

A pool of the gastric mucosa cDNA library (about 50,000 independent clones) in which amplification was found in the above (1) was subjected to plaque hybridization by using the digoxigenin-labeled probe.

A filter on which plaque-derived DNA samples had been transferred was soaked in 25 ml of a buffer containing 5× concentration of SSPE [composition of 1×SSPE comprises 180 mmol/l sodium chloride, 10 mmol/l sodium dihydrogenphosphate and 1 mmol/l ethylenediaminetetraacetic acid (EDTA) (pH 7.4)], 5× concentration of Denhart's solution [composition of 1× Denhart's solution comprises 0.02% (w/v) bovine serum albumin, 0.02% (w/v) Ficoll 400 and 0.02% (w/v) polyvinyl pyrrolidone], 0.5% sodium dodecyl sulfate (SDS) and 20 μg/ml sermon sperm DNA (hereinafter referred to as "hybridization buffer"), and pre-hybridization was carried out at 65° C. for 1 hour.

Next, the filter was soaked in 10 ml of the hybridization buffer containing 5 μl of the digoxigenin-labeled probe prepared in the above, and hybridization was carried out at 65° C. for 16 hours.

Thereafter, the filter was washed twice under conditions of soaking it in a buffer containing 2×SSPE and 0.1% SDS at 65° C. for 10 minutes, once under conditions of soaking it in a buffer containing 1×SSPE and 0.1% SDS at 65° C. for 15 minutes and then twice under conditions of soaking it in a buffer containing 0.2×SSPE and 0.1% SDS at 65° C. for 10 minutes.

As a result of the plaque hybridization, one hybridized independent clone was obtained. Phage DNA was prepared from this clone by using a kit manufactured by Qiagen (QIAGEN Lambda System). The phage DNA was digested with XbaI and SalI, and the resulting XbaI-SalI fragment of about 1.9 kb was subcloned between XbaI-SalI of pBluescript II SK(+). The thus constructed plasmid was named pBS-G3.

(3) Determination of a Nucleotide Sequence of the cDNA Inserted into Plasmid pBS-G3

A full nucleotide sequence of the cDNA contained in the pBS-G3 obtained in the above (2) was determined by the following method.

By using primers (M13-20 primer and reverse primer) specific for a sequence in pBluescript II SK(+), 5' side and 3' side sequences of the cDNA were determined. Synthetic DNAs specific for the determined sequences were produced, and further nucleotide sequences of the cDNA were determined by using the DNAs as primers. The full nucleotide sequence of the cDNA was determined by repeating this procedure.

For determination of nucleotide sequence, a DNA sequencer manufactured by LI-COR (dNA sequencer model 4000L) and a reaction kit (Sequitherm EXCEL II™ Long-Read™ DNA-sequencing kit-Lc: manufactured by AR BROWN), or a DNA sequencer 377 manufactured by PERKIN ELMER and a reaction kit (ABI Prism™ BigDye™ Terminator Cycle Sequencing Ready Reaction kit: manufactured by Applied Biosystems), were used. The full nucleotide sequence (1,912 bp) of the cDNA contained in pBS-G3 is shown in SEQ ID NO:5.

The cDNA encoded a polypeptide containing 397 amino acids having structure characteristic of the glycosyltransferases. The polypeptide was named G3 polypeptide, and its amino acid sequence is shown in SEQ ID NO:1.

The polypeptide showed 19% to 24% homology at amino acid level with the five human β1,3-galactosyltransferases so far cloned (β3Gal-T1, β3Gal-T2, β3Gal-T3, β3Gal-T4 and (β3Gal-T5) [Japanese Published Unexamined Patent Application No. 181759/94, *J. Biol. Chem.,* 273, 58 (1998), *J. Biol. Chem.,* 273, 433 (1998), *J. Biol. Chem.,* 273, 12770 (1998), *J. Biol. Chem.,* 274, 12499 (1999)].

The homology analysis was carried out using a Search Homology of sequence analysis soft GENETYX-MAC 10.1.

Also, the polypeptide showed homology of about 15% at amino acid level with the β1,3-N-acetylglucosaminyltransferase (β3GnT) so far cloned [*Proc. Natl. Acad. Sci. USA,* 96, 406 (1999)], and it was considered that the polypeptide comprises an N-terminal cytoplasmic region containing 9 amino acids, a subsequent membrane-binding region rich in hydrophobic nature containing 19 amino acids, a stem region containing at least 12 amino acids and the remaining C-terminal part comprising most part of the polypeptide and containing a catalytic region.

Also, based on the comparison of its amino acid sequence with that of the glycosyltransferase having homology and the information on the stem region and catalytic region of the glycosyltransferase (Japanese Published Unexamined Patent Application No. 181759/94), it was considered that the stem region comprises at least 12 amino acids. Accordingly, it is considered that the polypeptide having an amino acid sequence of positions 41-397 contains a catalytic region.

Based on these results and the results of Example 8 which will be described later, it was considered that this polypeptide is a novel β1,3-N-acetylglucosaminyltransferase.

The nucleotide sequence of SEQ ID NO:5 almost coincided with the sequence publicized by WO 98/44112. Also, amino acid sequence of the polypeptide (SEQ ID NO:1) encoded by this nucleotide sequence coincided with the sequence publicized by WO 98/44112.

However, the published patent predicts that the polypeptide is a secretory protein which is clearly a mistake, because it is actually a type II membrane protein. Also, this publication predicts that the polypeptide is a cardiac and pancreatic protein belonging to the skeletal muscle-derived growth factor super family based on its homology with other proteins, but it does not reveal its actual activity. The published patent describes general methods for producing the polypeptide in *E. coli*, insect cells and animal cells, but does not describe data on actual expression of the polypeptide. The present invention found for the first time that the polypeptide is a β1,3-N-acetylglucosaminyltransferase and has usefulness for the synthesis of sugar chains.

*Escherichia coli* mM294/pBS-G3 as *E. coli* having pBS-G3 has been deposited on Apr. 7, 1999, in National Institute of Bioscience and Human Technology, Agency of Industrial Science and Technology (postal code 305-8566, 1-1-3, Higashi, Tsukuba-shi, Ibaraki, Japan) as FERM BP-6694.

Example 3

Cloning of a Candidate Gene G4

(1) Cloning of a cDNA Fragment for a Candidate Gene G4

Primers specific for the candidate gene G4 (F-4-5 and R-4-5: their sequences are shown in SEQ ID NOS:11 and 12) were produced, PCR was carried out by using a single-stranded cDNA prepared from an organ or a cell or a cDNA library as the template, and the presence of cDNA having the corresponding sequence was examined. As a result, a DNA fragment of about 200 bp was amplified when a gastric mucosa cDNA library was used as the template. A specific method is the same as the method described in Example 1, except that the primers were changed.

The amplified DNA fragment of about 200 bp was inserted into a T-vector pT7Blue (manufactured by Novagen) to construct a plasmid pT7B-G4FR. As a result of the determination of a full nucleotide sequence of the cDNA fragment contained in pT7B-G4FR, it was confirmed that the sequence of the cDNA fragment coincided with one of the EST sequences found in Example 1. For determination of the nucleotide sequence, a DNA sequencer manufactured by LI-COR (dNA sequencer model 4000L), a DNA sequencer 377 manufactured by PERKIN ELMER and a reaction kit for each sequencer were used.

(2) Cloning of a Full-Length cDNA for the Candidate Gene G4

In order to obtain a full-length cDNA for G4, a digoxigenin-labeled probe was produced using PCR DIG probe synthesis kit (manufactured by Boehringer Mannheim). After 39 μl of a reaction solution containing 1 μg of pT7B-G4FR and 0.2 μmol/l of primers (F-4-5 and R-4-5) was heated at 97° C. for 5 minutes, it was cooled on ice for 5 minutes. Next, 1 unit of recombinant Taq DNA polymerase (manufactured by TaKaRa) was added thereto, and 30 cycles of the reaction using a reaction system constituted by 1 minute at 94° C., 1 minute at 65° C. and 1 minute at 72° C. as one cycle were carried out. A composition of the reaction solution was based on the instructions attached to the kit.

A pool of the gastric mucosa cDNA library (about 50,000 independent clones) in which amplification was found in the above (1) was subjected to plaque hybridization by using the digoxigenin-labeled probe.

A filter on which plaque-derived DNA samples had been transferred was soaked in 25 ml of the hybridization buffer, and pre-hybridization was carried out at 65° C. for 1 hour. Next, the filter was soaked in 10 ml of the hybridization buffer containing 5 μl of the digoxigenin-labeled probe produced in the above and hybridization was carried out at 65° C. for 16 hours. Thereafter, the filter was washed twice under conditions of soaking it in a buffer containing 2×SSPE and 0.1% SDS at 65° C. for 10 minutes, once under conditions of soaking it in a buffer containing 1×SSPE and 0.1% SDS at 65° C. for 15 minutes and then twice under conditions of soaking it in a buffer containing 0.2×SSPE and 0.1% SDS at 65° C. for 10 minutes.

As a result of the plaque hybridization, one hybridized independent clone was obtained. By carrying out in vivo excision in accordance with a manual provided by Stratagene, a plasmid pBS-G4-2 was recovered from the clone.

In the same manner, a human placenta cDNA library was prepared, and a plasmid pBS-G4 was obtained from the library.

(3) Determination of Nucleotide Sequences of the cDNAs Inserted into Plasmids pBS-G4 and pBS-G4-2

Full nucleotide sequences of the cDNAs molecules contained in the pBS-G4 and pBS-G4-2 obtained in the above (2) was determined by the following method.

By using primers (M13-20 primer and reverse primer) specific for a sequence in pBluescript II SK(−), 5' side and 3' side sequences of the cDNAs were determined. Synthetic DNAs specific for the determined sequences were produced, and further nucleotide sequences of the cDNAs were determined by using the DNAs as primers. Full nucleotide sequences of the cDNAs were determined by repeating this procedure.

For determination of the nucleotide sequence, a DNA sequencer manufactured by LI-COR (dNA sequencer model 4000L) and a reaction kit (Sequitherm EXCEL II™ Long-Read™ DNA-sequencing kit-Lc: manufactured by AR BROWN), or a DNA sequencer 377 manufactured by PERKIN ELMER and a reaction kit (ABI Prism™ BigDye™ Terminator Cycle Sequencing Ready Reaction kit: manufactured by Applied Biosystems), were used.

A full nucleotide sequence (2,205 bp) of the cDNA contained in pBS-G4 is shown in SEQ ID NO:6. The cDNA encoded a polypeptide composed of 372 amino acids having a structure characteristic of the glycosyltransferase. The polypeptide was named G4 polypeptide, and its amino acid sequence is shown in SEQ ID NO:2.

A full nucleotide sequence (2,180 bp) of the cDNA contained in pBS-G4-2 is shown in SEQ ID NO:7. The cDNA encoded a polypeptide containing 372 amino acids having a structure characteristic of the glycosyltransferase. The polypeptide was named G4-2 polypeptide, and its amino acid sequence is shown in SEQ ID NO:3.

The cDNA contained in pBS-G4 was named G4 cDNA, and the cDNA contained in pBS-G4-2 was named G4-2 cDNA.

The nucleotide sequence of the 5' non-translation region was different between G4 cDNA and G4-2 cDNA, and substitution of at least two nucleotides was found (cf. FIGS. 1 to 4). In the translation region, the 1111th nucleotide of G4 cDNA was adenine, but the corresponding nucleotide in G4-2 cDNA was substituted with guanine. Accordingly, the 328th amino acid of G4 polypeptide is His, while the 328th amino acid of G4-2 polypeptide is substituted with Arg.

The fact that the nucleotide sequence of the 5' non-translation region is different between G4 cDNA and G4-2 cDNA indicates that different promoters are acting in the placenta and stomach. It is considered that other nucleotide substitutions are caused by individual difference, somatic cell mutation or error of reverse transcriptase. As shown in the following Example, both of the proteins encoded by G4 cDNA and G4-2 cDNA possessed a β1,3-N-acetylglucosaminyltransferase activity.

Each of the G4 and G4-2 polypeptides showed 22% to 26% homology at amino acid level with the five human β1,3-galactosyltransferases so far cloned (β3Gal-T1, β3Gal-T2, β3Gal-T3, β3Gal-T4 and (β3Gal-T5) [Japanese Published Unexamined Patent Application No. 181759/94, *J. Biol. Chem.*, 273, 58 (1998), *J. Biol. Chem.*, 273, 433 (1998), *J. Biol. Chem.*, 273, 12770 (1998), *J. Biol. Chem.*, 274, 12499 (1999)]. The homology analysis was carried out by using a Search Homology of sequence analysis soft GENETYX-MAC 10.1.

Also, each of these polypeptides showed homology of about 17.5% at amino acid level with the β1,3-N-acetylglucosaminyltransferase (β3GnT) so far cloned [*Proc. Natl. Acad. Sci. USA*, 96, 406 (1999)]. It was considered that each of the polypeptides comprises an N-terminal cytoplasmic region containing 11 amino acids, a subsequent membrane-binding region rich in hydrophobic nature containing 21 amino acids, a stem region containing at least 12 amino acids and the remaining C-terminal pert comprising most of the polypeptide and containing a catalytic region. Based on the comparison of their amino acid sequences with that of the glycosyltransferase having homology and the information on the stem region and catalytic region of the glycosyltransferase (Japanese Published Unexamined Patent Application No. 181759/94), it was considered that the stem region comprises at least 12 amino acids. Accordingly, it is considered that the polypeptide having an amino acid sequence of positions 45-372 contains a catalytic region.

Based on these results and the results of Examples 8, 9, 10 and 12 which will be described later, it was considered that each of these polypeptides is a novel β1,3-N-acetylglucosaminyltransferase.

The nucleotide sequence of SEQ ID NO:6 or 7 almost coincided with the sequence publicized by WO 98/44112. Also, amino acid sequence of the polypeptide (SEQ ID NO:2) encoded by the nucleotide sequence of SEQ ID NO:6 coincided with the sequence published by WO 98/21328. However, the published patent merely describes that the polypeptide is a type II membrane protein, but does not reveal actual activity of the polypeptide. The present invention found for the first time that the polypeptide is a β1,3-N-acetylglucosaminyltransferase and has usefulness for the synthesis of sugar chains.

*Escherichia coli* mM294/pBS-G4 as *E. coli* having pBS-G4-2 has been deposited on Apr. 7, 1999, in National Institute of Bioscience and Human Technology, Agency of Industrial Science and Technology (postal code 305-8566, 1-1-3, Higashi, Tsukuba-shi, Ibaraki, Japan) as FERM BP-6695.

Example 4

Cloning of a Candidate Gene G7

(1) Cloning of a cDNA for a Candidate Gene G7

Primers specific for the candidate gene G7 (F-7-5a and R-7-3a: their sequences are shown in SEQ ID NOS:13 and 14) were produced, PCR was carried out by using a single-stranded cDNA prepared from various organs or cells, or various cDNA libraries as the template, and the presence of cDNA having the corresponding sequence was examined. As a result, a DNA fragment of about 1.3 kb was amplified when a single-stranded cDNA derived from a human neuroblastoma cell line SK-N-MC was used as the template. The specific method is shown below.

The cell line SK-N-MC was obtained from American Type Culture Collection (ATCC). Total RNA was prepared from the SK-N-MC cells in accordance with a general method [*Biochemistry,* 18, 5294 (1977)]. A single-stranded cDNA was synthesized from 5 μg of the total RNA using a kit (SUPERSCRIPT™ Preamplification System; manufactured by BRL). The reaction was carried out in 21 μl, and the solution after the reaction was diluted 50 times with water and stored at −80° C. until its use.

After 40 μl of a reaction solution [10 mmol/l Tris-HCl (pH 8.3), 50 mmol/l KCl, 1.5 mmol/l $MgCl_2$, 0.2 mmol/l dNTP, 0.001% (w/v) gelatin and 0.2 μmol/l gene-specific primer] containing 10 μl of the single-stranded cDNA was heated at 97° C. for 5 minutes, it was cooled on ice for 5 minutes. Next, 1 unit of recombinant Taq DNA polymerase (manufactured by TaKaRa) was added thereto, and 30 cycles of the reaction by using a reaction system constituted by 30 seconds at 94° C., 1 minute at 60° C. and 2 minutes at 72° C. as 1 cycle were carried out.

The thus amplified DNA fragment of about 1.3 kb was inserted into a T-vector pT7Blue (manufactured by Novagen) to construct a plasmid pT7B-G7.

(2) Determination of a Nucleotide Sequence of the cDNA Inserted into Plasmid pT7B-G7

The full nucleotide sequence of the cDNA contained in pT7B-G7 obtained in the above (1) was determined by the following method.

By using primers (M13-20 primer and reverse primer) specific for a sequence in pT7Blue, 5' side and 3' side sequences of the cDNA were determined. Synthetic DNAs specific for the determined sequences were produced, and further nucleotide sequences of the cDNA were determined using the DNAs as primers. The full nucleotide sequence of the cDNA was determined by repeating this procedure.

For determination of the nucleotide sequence, a DNA sequencer manufactured by LI-COR (dNA sequencer model 4000L) and a reaction kit (Sequitherm EXCEL II™ Long-Read™ DNA-sequencing kit-Lc: manufactured by AR BROWN), or a DNA sequencer 377 manufactured by PERKIN ELMER and a reaction kit (ABI Prism™ BigDye™ Terminator Cycle Sequencing Ready Reaction kit: manufactured by Applied Biosystems), were used.

The full nucleotide sequence (1,296 bp) of the cDNA contained in pT7B-G7 is shown in SEQ ID NO:8.

The cDNA encoded a polypeptide composed of 378 amino acids having a structure characteristic of the glycosyltransferase. The polypeptide was named G7 polypeptide, and its amino acid sequence is shown in SEQ ID NO:4.

The G7 polypeptide showed 22% to 25% homology at amino acid level with the five human β1,3-galactosyltransferases so far cloned (β3Gal-T1, β3Gal-T2, β3Gal-T3, β3Gal-T4 and (β3Gal-T5) [Japanese Published Unexamined Patent Application No. 181759/94, *J. Biol. Chem.,* 273, 58 (1998), *J. Biol. Chem.,* 273, 433 (1998), *J. Biol. Chem.,* 273, 12770 (1998), *J. Biol. Chem.,* 274, 12499 (1999)].

The homology analysis was carried out by using a Search Homology of sequence analysis soft GENETYX-MAC 10.1.

Also, the polypeptide showed homology of about 14.8% at amino acid level with the human β1,3-N-acetylglucosaminyltransferase (β3GnT) so far cloned [*Proc. Natl. Acad. Sci. USA,* 96, 406 (1999)], and it was considered that it comprises an N-terminal cytoplasmic region containing 29 amino acids, a subsequent membrane-binding region rich in hydrophobic nature containing 20 amino acids, a stem region containing at least 12 amino acids and the remaining C-terminal pert comprising most of the polypeptide and containing a catalytic region. Based on the comparison of its amino acid sequence with that of the glycosyltransferase having homology and the information on the stem region and catalytic region of the glycosyltransferase (Japanese Published Unexamined Patent Application No. 181759/94), it was considered that the stem region comprises at least 12 amino acids. Accordingly, it is considered that the polypeptide having an amino acid sequence of positions 62-378 contains a catalytic region.

Based on these results and the results of Examples 8 which will be described later, it was considered that the polypeptide is a novel β1,3-N-acetylglucosaminyltransferase.

*Escherichia coli* mM294/pT7B-G7 as *E. coli* having pT7B-G7 has been deposited on Apr. 7, 1999, in National Institute of Bioscience and Human Technology, Agency of Industrial Science and Technology (postal code 305-8566, 1-1-3, Higashi, Tsukuba-shi, Ibaraki, Japan) as FERM BP-6696.

Example 5

Homology Analysis on Amino Acid Sequences

A dendrogram was created using the amino acid sequences of G3, G4-2 and G7 polypeptides, amino acid sequences of known human β1,3-galactosyltransferases (β3Gal-T1, β3Gal-T2, β3Gal-T3, β3Gal-T4 and (β3Gal-T5) and the amino acid sequence of known human β1,3-N-acetylglucosaminyltransferase (β3GnT) (cf. FIG. 5). The dendrogram was created using CLUSTAL X Multiple Sequence Alignment Program (ftp://ftp-igbmc.u-strasbg.fr/pub/ClustalX/). As a result, it was found that the G3, G4-2 and G7 polypeptides form one subgroup. The G3 polypeptide showed 39.6% and 44.5% of homology with G4-2 and G7 polypeptides, respectively. The G4-2 polypeptide showed 42.5% homology with the G7 polypeptide.

Example 6

Construction of Expression Plasmids for Animal Cell

In order to express each polypeptide encoded by the G3, G4, G4-2 and G7 cDNAs obtained in Examples 2 to 4, expression plasmids were constructed by inserting each cDNA into an expression vector pAMo [*J. Biol. Chem.,* 268, 22782 (1993), alias pAMoPRC3Sc (Japanese Published Unexamined Patent Application No. 336963/93)].

Figure 6:
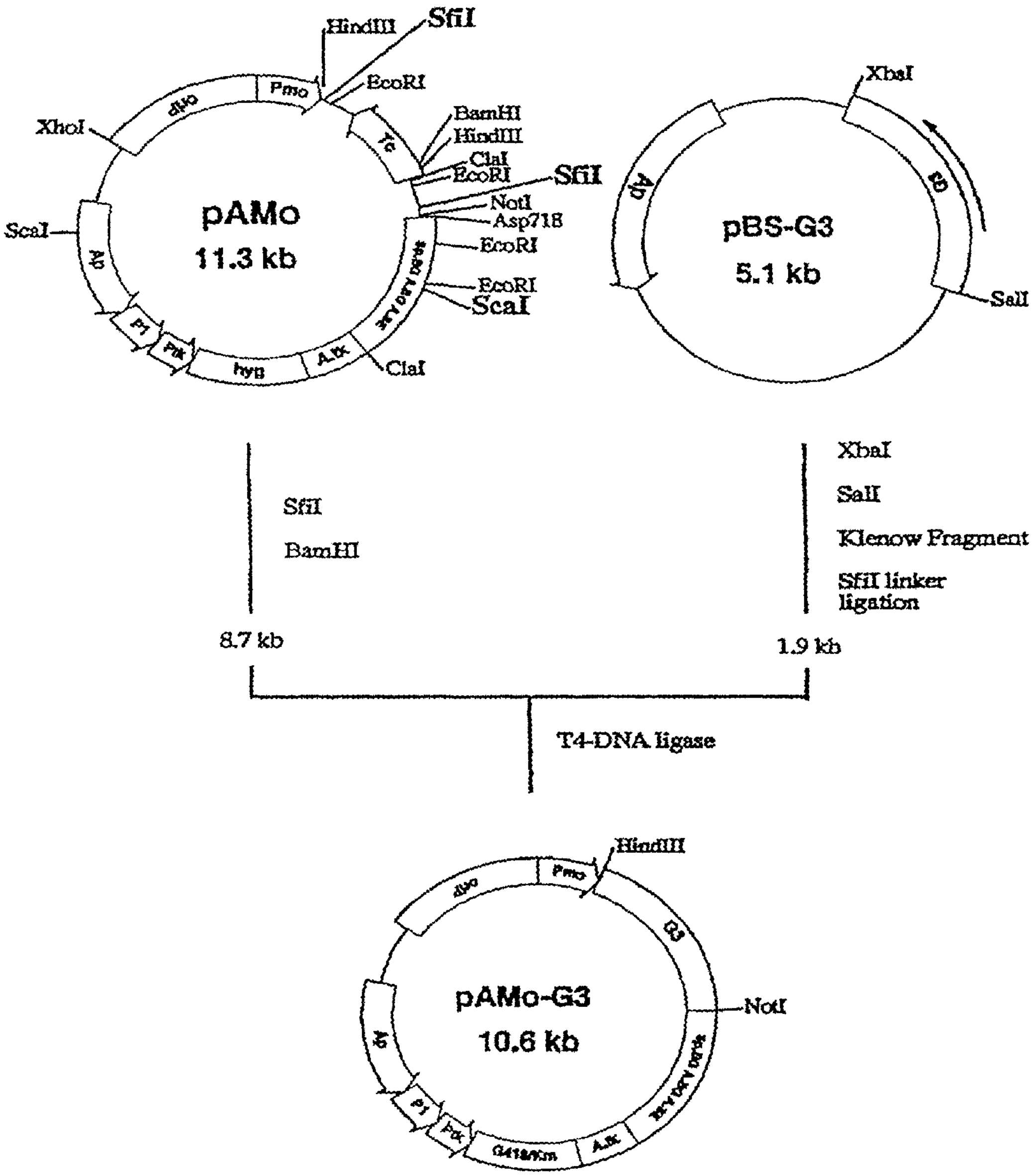
FIG. 6 is a graph showing construction steps of a plasmid pAMo-G3.

(1) Construction of Plasmid pAMo-G3 for Expressing G3 Polypeptide (cf. FIG. 6)

pBS-G3 was digested with restriction enzymes XbaI and SalI and then treated with DNA polymerase Klenow fragment to form blunt ends. Thereafter, SfiI linkers (SEQ ID NOS:15 and 16) were added thereto to obtain an SfiI fragment of about 1.9 kb. On the other hand, pAMo was digested with SfiI and BamHI and then an SfiI fragment of 8.7 kb was obtained. By linking these 2 fragments, an expression plasmid pAMo-G3 was constructed.

Synthesis and phosphorylation of the SfiI linkers (SEQ ID NOS:15 and 16) were carried out in accordance with a general method (Japanese Published Unexamined Patent Application No. 336963/93).

Figure 7:
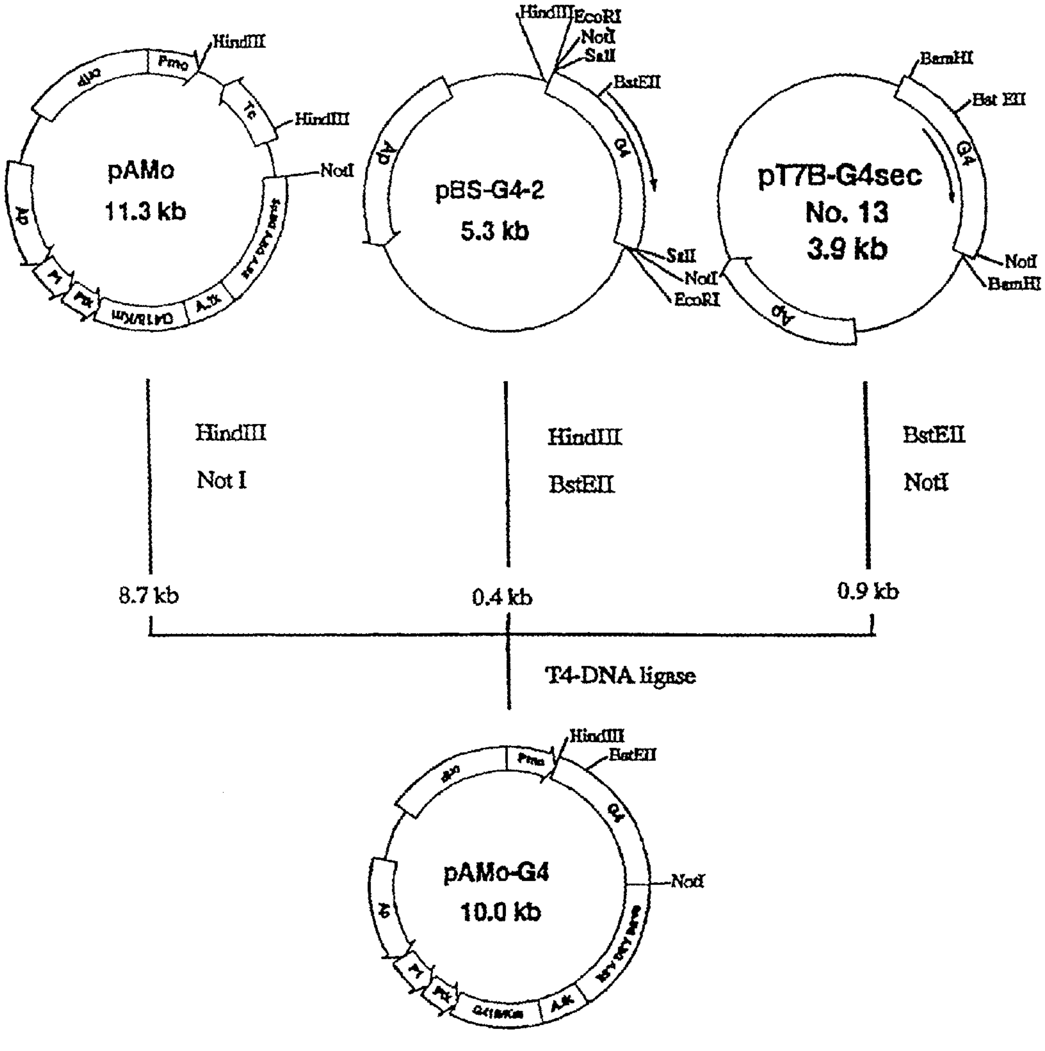
FIG. 7 is a graph showing construction steps of a plasmid pAMo-G4.

(2) Construction of Plasmid pAMo-G4 for Expressing G4 Polypeptide (cf. FIG. 7)

pBS-G4 was digested with restriction enzymes HindIII and BstEII and then a HindIII-BstEII fragment of 0.4 kb was obtained. Also, pT7B-G4sec was digested with restriction enzymes BstEII and NotI and then a BstEII-NotI fragment of 0.9 kb was obtained. The pT7B-G4sec was constructed by the method shown in Example 9(1) which will be described later. On the other hand, pAMo was digested with HindIII and NotI and then a HindIII-NotI fragment of 8.7 kb was obtained. By linking these 3 fragments, an expression plasmid pAMo-G4 was constructed.

Figure 8:
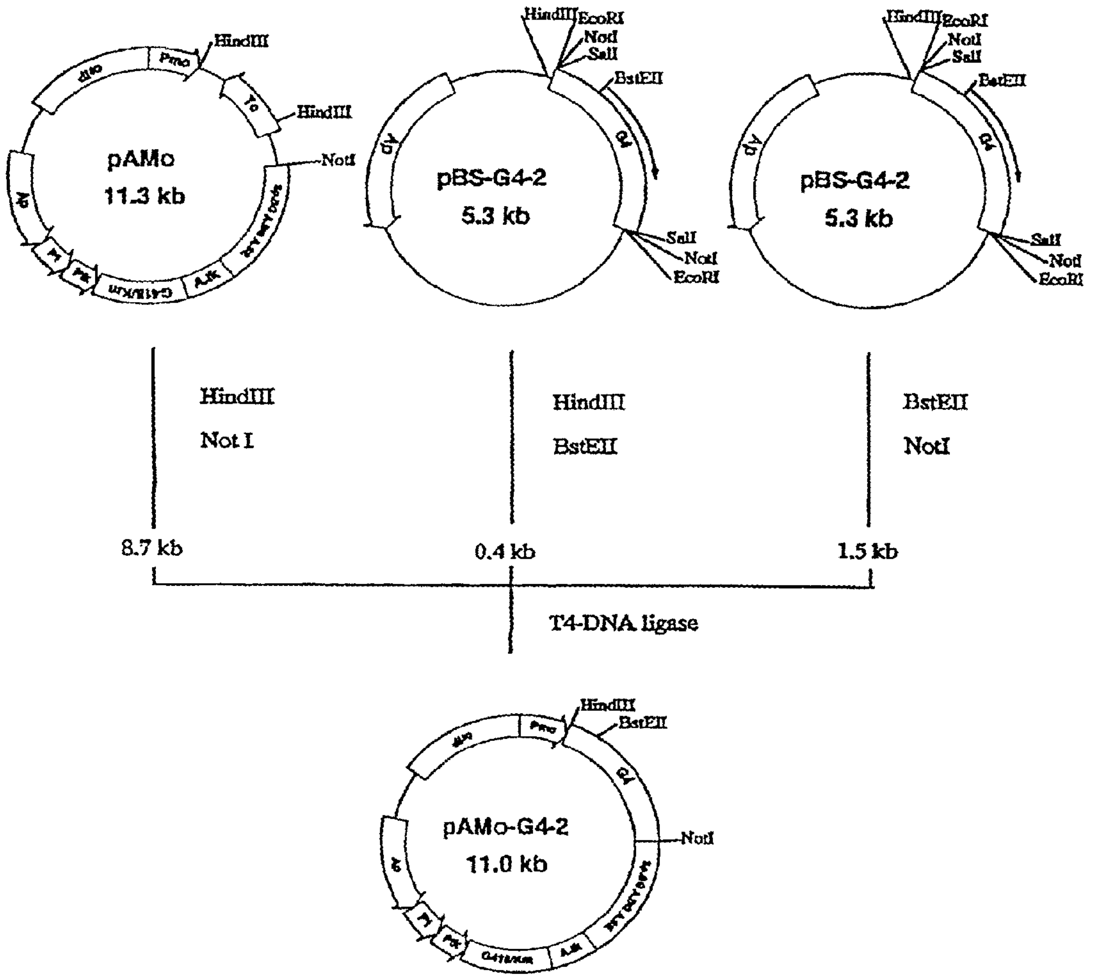
FIG. 8 is a graph showing construction steps of a plasmid pAMo-G4-2.

(3) Construction of Plasmid pAMo-G4-2 for Expressing G4-2 Polypeptide (cf. FIG. 8)

pBS-G4-2 was digested with restriction enzymes HindIII and BstEII and then a HindIII-BstEII fragment of 0.4 kb was obtained. Also, pBS-G4-2 was digested with restriction enzymes BstEII and NotI and then a BstEII-NotI fragment of 1.5 kb was obtained. On the other hand, pAMo was digested with HindIII and NotI and then a HindIII-NotI fragment of 8.7 kb was obtained. By linking these 3 fragments, an expression plasmid pAMo-G4-2 was constructed.

Figure 9:
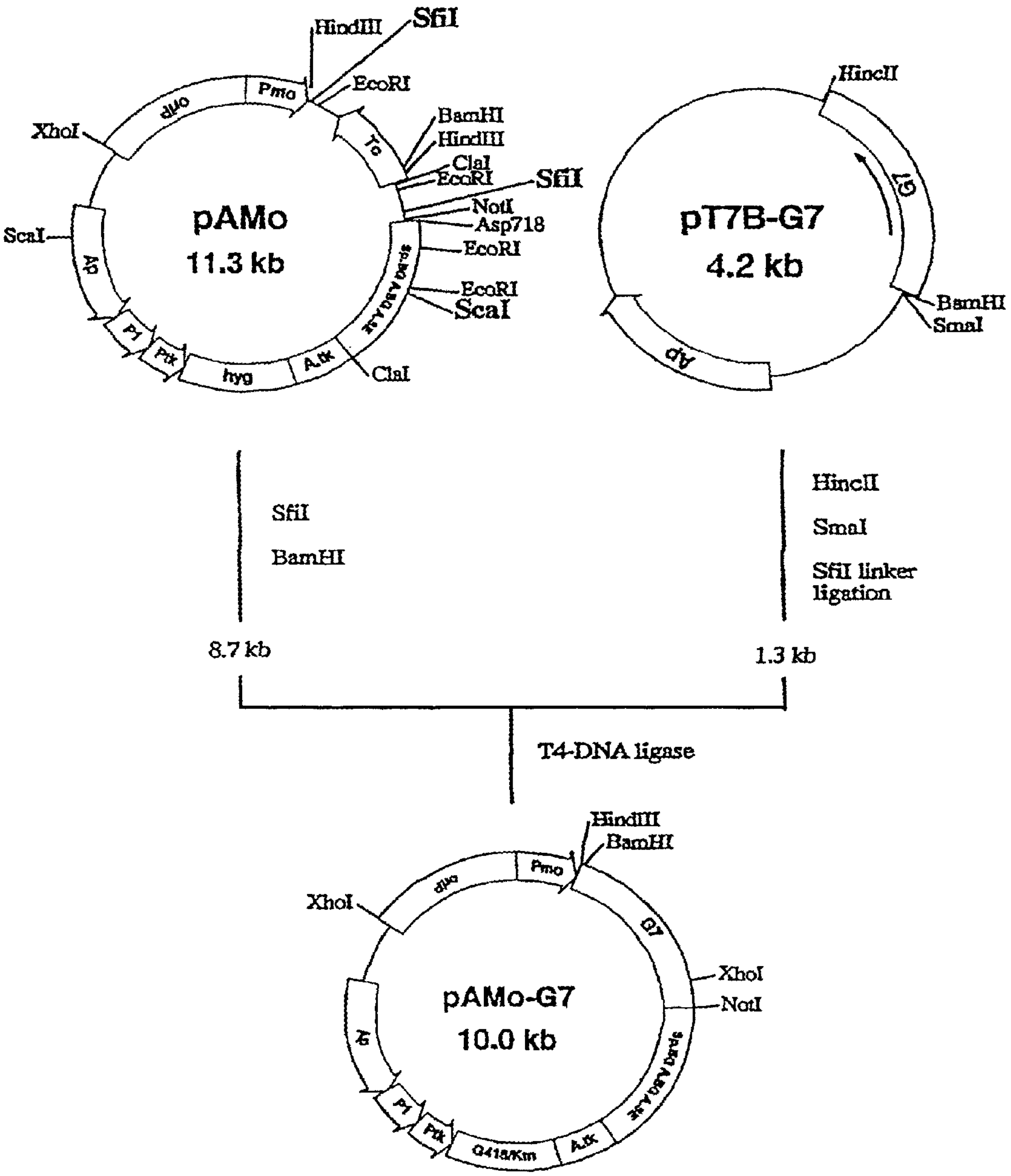
FIG. 9 is a graph showing construction steps of a plasmid pAMo-G7.

(4) Construction of Plasmid pAMo-G7 for Expressing G7 Polypeptide (cf. FIG. 9)

pT7B-G7 was digested with restriction enzymes SmaI and HincII and then SfiI linkers (SEQ ID NOs:15 and 16) were added thereto to obtain an SfiI fragment of about 1.3 kb. On the other hand, pAMo was digested with SfiI and BamHI and then an SfiI fragment of 8.7 kb was obtained. By linking these 2 fragments, an expression plasmid pAMo-G7 was constructed.

Example 7

Synthesis of Poly-N-acetyllactosamine Sugar Chain in Cultured Human Cells Transformed by a Plasmid Expressing Each Polypeptide of G3, G4, G4-2 and G7

(1) Acquisition of Stable Transformants

Each of a control plasmid (pAMo) and various expression plasmids constructed in Example 6 (pAMo-G3, pAMo-G4, pAMo-G4-2 and pAMo-G7) was dissolved in a buffer containing 10 mmol/l Tris-HCl (pH 8.0) and 1 mmol/l EDTA (sodium ethylenediaminetetraacetate) (hereinafter referred to as "TE buffer") to give a concentration of 1 μg/μl and then introduced into Namalwa KJM-1 cell [*Cytotechnology,* 1, 151 (1988)] by electroporation method [*Cytotechnology,* 3, 133 (1990)] to obtain respective transformants.

After introducing 4 μg per $1.6\times10^6$ cells of each plasmid, the cells were suspended in 8 ml of RPMI 1640/ITPSG medium [RPMI 1640 medium (manufactured by Nissui Pharmaceutical) supplemented with 1/40 volume of 7.5%

$NaHCO_3$, 3% of 200 mmol/l L-glutamine solution (manufactured by GIBCO), 0.5% penicillin/streptomycin solution (manufactured by GIBCO, 5,000 units/ml penicillin and 5,000 μg/ml streptomycin), N-2-hydroxyethylpiperazine-N'-2-ethanesulfonic acid (N-2-hydroxyethylpiperazine-N'-2-hydroxypropane-3-sulfonic acid; HEPES) (10 mmol/l), insulin (3 μg/ml), transferrin (5 μg/ml), sodium pyruvate (5 mmol/l), sodium selenite (125 nmol/l) and galactose (1 mg/ml)] and cultured at 37° C. for 24 hours in a $CO_2$ incubator. Thereafter, G418 (manufactured by GIBCO) was added thereto to give a concentration of 0.5 mg/ml, followed by culturing for 14 days to obtain a stable transformant. Each of the thus obtained transformants was subcultured in RPMI 1640/ITPSG medium containing 0.5 mg/ml of G418.

(2) Measurement of the Amount of Poly-N-Acetyllactosamine Sugar Chains Expressed in Each Transformant The amount of poly-N-acetyllactosamine sugar chains expressed in each transformant can be analyzed using FACS after fluorescence staining by using antibodies or lectins capable of recognizing poly-N-acetyllactosamine sugar chains. Anti-i antibody (Den) can be used as an antibody which recognize poly-N-acetyllactosamine sugar chain. As the lectin which recognizes poly-N-acetyllactosamine sugar chain, LEA, PWM and DSA can be used.

An example of the method in which a lectin (LEA or PWM) capable of recognizing a poly-N-acetyllactosamine sugar chain is used is shown below.

The transformed cells ($5\times10^6$ cells for each transformant) were suspended in 100 μl of PBS (8 g/l NaCl, 0.2 g/l KCl, 1.15 g/l $Na_2HPO_4$ (anhydrous) and 0.2 g/l $KH_2PO_4$) containing 20 mU of *Clostridium perfringens* neuraminidase (N 2133 manufactured by SIGMA), followed by reacting at 37° C. for 1 hour to thereby carrying out the sialidase treatment of the transformed cells.

The cells (about $1\times10^6$) were transferred into a microtube (1.5 ml: manufactured by Eppendorf) and centrifuged (550×g for 7 minutes) to collect the cells.

The cells were washed with 0.9 ml of a 0.1% sodium azide-containing phosphate buffer PBS (A-PBS: 8 g/l NaCl, 0.2 g/l KCl, 1.15 g/l $Na_2HPO_4$ (anhydrous), 0.2 g/l $KH_2PO_4$, 0.1% sodium azide), and then 20 μl of FITC-labeled LEA (manufactured by EY Laboratories) diluted to 10 μg/ml with A-PBS or FITC-labeled PWM (manufactured by EY Laboratories) diluted to 100 μg/ml with A-PBS was added to the washed cells and suspended, subsequently carrying out the reaction at 4° C. for 1 hour.

After the reaction, the cells were washed once with 0.9 ml of A-PBS and then suspended in 0.6 ml of A-PBS to carry out the FACS (fluorescence activated cell sorter) analysis using FACSCaliber (manufactured by Becton Dickinson Immunocytometry Systems USA). As a control test, the same analysis was carried out by using A-PBS instead of the lectins.

Figure 10:
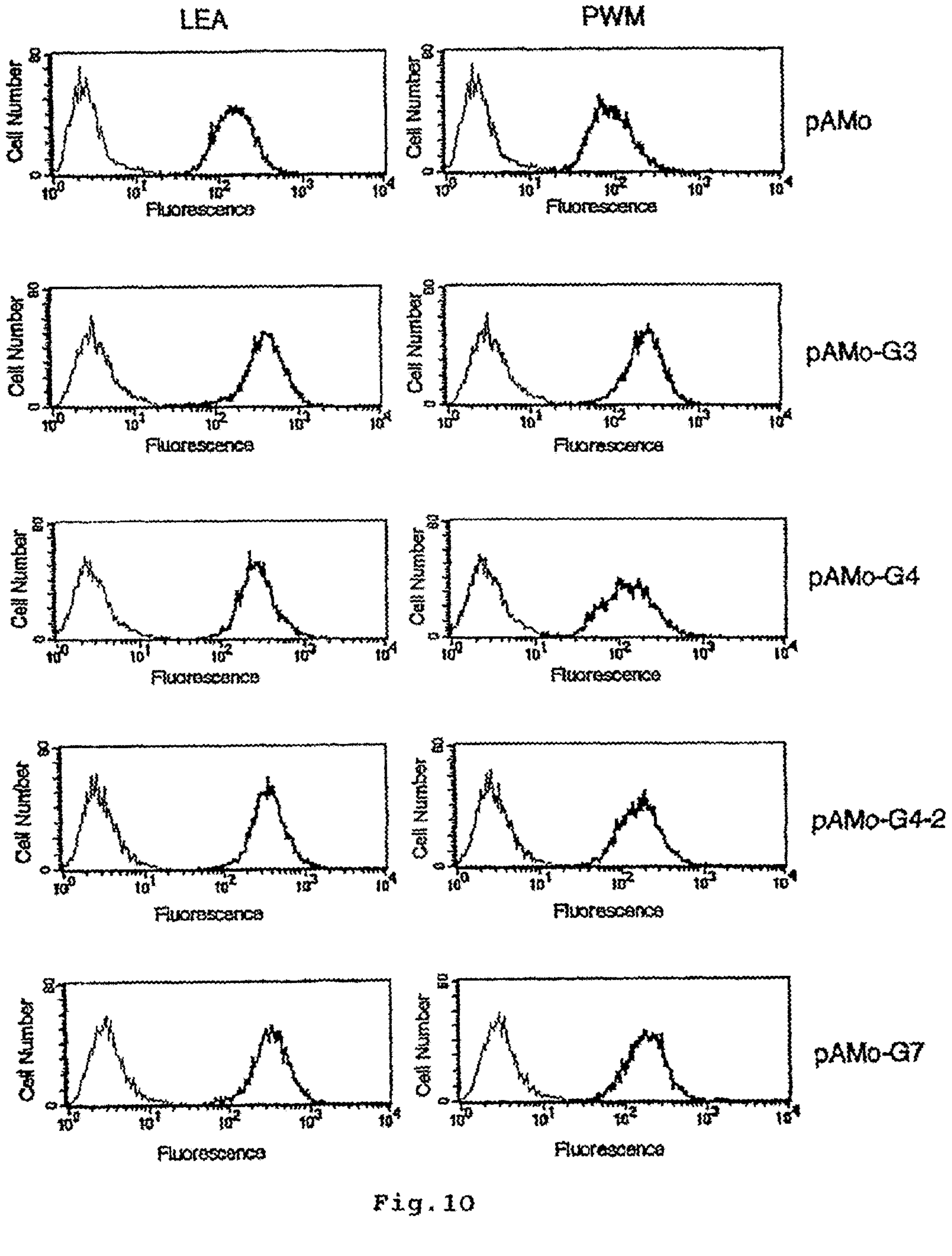
FIG. 10 is a result obtained by introducing an expression plasmid (pAMo-G3, pAMo-G4, pAMo-G4-2 or pAMo-G7) and a control plasmid pAMo respectively into Namalwa KJM-1 cell, carrying out indirect fluorescent antibody staining using LEA lectin (thick line), PWM lectin (thick line) or A-PBS (thin line) and then analyzing them using FACS.

In the cells into which pAMo-G3, pAMo-G4, pAMo-G4-2 or pAMo-G7 was introduced, reactivity for LEA was higher in comparison with the pAMo-introduced cells (FIG. 10). Also, in the cells into which pAMo-G3, pAMo-G4, pAMo-G4-2 or pAMo-G7 was introduced, reactivity for PWM was higher in comparison with the pAMo-introduced (FIG. 10).

The results show that poly-N-acetyllactosamine sugar chains were newly synthesized on sugar chains of cell surface glycoproteins or glycolipids by expressing cDNA of G3, G4, G4-2 or G7 in Namalwa KJM-1 cell.

Also, it shows that poly-N-acetyllactosamine sugar chains were newly synthesized on sugar chains of glycoproteins or oligosaccharides secreted from cells in which cDNA of G3, G4, G4-2 or G7 is expressed. Accordingly, it is possible to add a sugar chain containing a poly-N-acetyllactosamine to a glycoprotein produced as a secreted form by secreting and producing a useful glycoprotein by use of cells in which cDNA of G3, G4, G4-2 or G7 is expressed as a host.

On the other hand, when the fluorescence staining was carried out on the transformed cells by using DU-PAN-2 which is an antibody for sialyl Lewis c sugar chains, reactivity of the antibody was not changed. The method was carried out in accordance with a general method [*J. Biol. Chem.,* 274, 12499 (1999)].

Example 8

Measurement of β1,3-N-Acetylglucosaminyltransferase Activity in Cultured Human Cells Transformed by a Plasmid Capable of Expressing G3, G4, G4-2 or G7 Polypeptide The β1,3-N-acetylglucosaminyltransferase activity was examined by using a cell extract of stable transformants which were transformed by a plasmid capable of expressing G3, G4, G4-2 or G7 polypeptide obtained in Example 7.

The transformed cells (about $2\times10^7$) were transferred into a microtube (1.5 ml: manufactured by Eppendorf) and centrifuged (550×g for 7 minutes) to collect the cells. The cells were washed with 0.9 ml of PBS, the washed cells were suspended in a solution (100 μl) composed of 20 mmol/l HEPES (pH 7.2) and 1% Triton X-100 and then the cells were disrupted by a sonicator (Bioruptor; manufactured by Cosmo Bio). After standing at 4° C. for 1 hour, a supernatant was obtained by centrifugation (550×g for 7 minutes). The supernatant was used as an enzyme sample. The β1,3-N-acetylglucosaminyltransferase activity was measured by using this enzyme sample.

Preparation of a pyridylaminated sugar chain substrates and activity measurement were carried out in accordance with known methods [Japanese Published Unexamined Patent Application No. 181757/94, Japanese Published Unexamined Patent Application No. 823021/94, *J. Biol. Chem.,* 269, 14730 (1994), *J. Biol. Chem.,* 267, 2994 (1992)].

Specifically, the reaction was carried out at 37° C. for 16 hours in 30 μl of an assay solution [200 mmol/l of MOPS (pH 7.5), 50 mmol/l of UDP-GlcNAc (SIGMA), 20 mmol/l of $MnCl_2$, 0.3% Triton X-100, 50 μM of a pyridylaminated sugar chain substrate and 10 μl of the above cell lysate], and then products were detected by a high performance liquid chromatography (HPLC).

As a substrate, lacto-N-neotetraose (Galβ1-4GlcNAcβ1-3Galβ1-4Glc; hereinafter referred to as "LNnT") fluorescence-labeled with aminopyridine was used.

LNnT was purchased from Oxford Glycosystems. Fluorescence labeling of the oligosaccharide was carried out in accordance with the general method [*Agric. Biol. Chem.,* 54, 2169 (1990)].

After carrying out the reaction by using the assay solution with or without UDP-GlcNAc (sugar donor), HPLC was carried out and peaks appeared only in the assay solution containing UDP-GlcNAc were defined as products.

The assay solution after completion of the reaction was treated at 100° C. for 5 minutes and then centrifuged at 10,000×g for 5 minutes, and a portion (5 μl) of the thus obtained supernatant was applied to HPLC.

The HPLC was carried out by using TSK-gel ODS-80Ts column (4.6×300 mm; Tosoh); 0.02 M ammonium acetate buffer (pH 4.0) was used as an eluate at elution temperature 50° C. and flow rate 0.5 ml/min.

Products were detected by using a fluorescence spectrum photometer FP-920 (JASCO Corporation) (excitation wavelength 320 nm, radiation wavelength 400 nm). In identifying the product, coincidence of its elution time with that of a standard sugar chain was used as the index. As a standard sugar chain, aminopyridylated GlcNAcβ1-3Galβ1-4GlcNAcβ1-3Galβ1-4Glc was used.

The amount of products was measured by using pyridylaminated lactose as a standard and comparing their fluorescence intensity.

As a result of the activity measurement by using a cell extract of stable transformants which were introduced with a control plasmid (pAMo) or each expression plasmid (pAMo-G3, pAMo-G4, pAMo-G4-2 or pAMo-G7), ratio of a substrate (LNnT) converted into a product (GlcNAcβ1-3Galβ1-4GlcNAcβ1-3Galβ1-4Glc) in cells transformed by an expression plasmid for G3, G4, G4-2 or G7 polypeptide was increased to be 2.7%, 2.8%, 2.8% and 2.3% respectively, while it was 1.8% in the control plasmid-introduced cells. That is, it was found that the β1,3-N-acetylglucosaminyltransferase activity was higher in the cells transformed by an expression plasmid for G3, G4, G4-2 or G7 polypeptide in comparison with the control plasmid-introduced cells.

Based on these results, it was confirmed that the G3, G4, G4-2 or G7 polypeptide is a novel β1,3-N-acetylglucosaminyltransferase. The result shows a possibility that a sugar chain in which N-acetylglucosamine is added via a β1,3-linkage to the galactose residue existing at the non-reducing terminal of a sugar chain can be synthesized by using the G3, G4, G4-2 or G7 polypeptide.

Example 9

Secretion Production of FLAG Peptide-Fused β1,3-N-Acetylglucosaminyltransferase (G4) by Using Namalwa KJM-1 Cell as a Host (1) Construction of a FLAG Peptide-Fused Secretion Vector pAMoF2

A secretion vector pAMoF2 was constructed for expressing a protein as a secreted form fused with a FLAG peptide (SEQ ID NO:17) at N-terminal of the protein. DNAs encoding a signal sequence of an immunoglobulin K and the FLAG peptide were constructed by using 6 synthetic DNA fragments.

A HindIII-Asp718 fragment of about 8.7 kb was obtained by digesting pAMo with HindIII and Asp718. Six DNA fragments [IgK-1 (SEQ ID NO:18), IgK-2 (SEQ ID NO:19), IgK-3 (SEQ ID NO:20), IgK-4 (SEQ ID NO:21), IgK-5 (SEQ ID NO:22) and IgK-6 (SEQ ID NO:23)] were synthesized as linkers for linking the HindIII-digestion site and Asp718-digested site. Also, each of the restriction enzyme digestion sites of PmaCI, StuI and SnaBI was generated in the linkers constructed by these DNA fragments. The 6 DNA fragments were respectively synthesized by 380A DNA Synthesizer manufactured by Applied Biosystems. The thus synthesized DNA fragments were used after phosphorylation by using T4 polynucleotide kinase (manufactured by TaKaRa, the same shall apply hereinafter).

A plasmid pAMoF2 was constructed by linking the thus obtained 6 phosphorylated synthetic DNA fragments and the HindIII-Asp718 fragment of about 8.7 kb.

(2) Construction of a Plasmid pAMoF2-i52S

DNA shown by SEQ ID NO:24 (hereinafter referred to as "C12-7") and DNA shown by SEQ ID NO:25 (hereinafter referred to as "C12-9") were synthesized as primers for PCR (they can also be purchased from Sawaday Technology).

They are designed such that a BamHI site is generated in C12-7, and a NotI site in C12-9.

PCR was carried out by using a kit manufactured by TaKaRa (GeneAmp™ DNA Amplification Reagent Kit with AmpliTaq™ Recombinant Taq DNA Polymerase). A reaction solution was prepared in accordance with the method of the kit, and 10 cycles of a reaction at 94° C. for 30 seconds, 65° C. for 1 minute and 72° C. for 2 minutes, and subsequent reaction at 72° C. for 7 minutes were carried out by using a DNA thermal cycler (PERKIN ELMER CETUS DNA Thermal Cycler; available from TaKaRa). As a template, 10 ng of a plasmid pAMo-i [*Proc. Natl. Acad. Sci. USA,* 94, 14294 (1997)] was used. A DNA fragment of about 1.1 kb was obtained by the PCR.

A plasmid pT7B-i52S No. 3 was constructed by linking the PCR-amplified DNA fragment of about 1.1 kb and a T-vector pT7Blue (manufactured by Novagen).

Next, a plasmid pAMoF2-i52S was constructed.

A StuI-BanIII fragment of about 7.2 kb was obtained by digesting pAMoF2 with StuI and BanIII. A BanIII-NotI fragment of about 1.7 kb was obtained by digesting pAMo with BanIII and NotI. After digesting pT7B-i52S No. 3 with BamHI, the 5' cohesive end formed by the BamHI digestion was changed to blunt end using *E. coli* DNA polymerase I Kleow fragment and then the fragment was digested with NotI to thereby obtain a BamHI (blunt end)-NotI fragment of about 1.1 kb.

The plasmid pAMoF2-i52S was constructed by linking the thus obtained StuI-BanIII fragment of about 7.2 kb, BanIII-NotI fragment of about 1.7 kb and BamHI (blunt end)-NotI fragment of about 1.1 kb.

Figure 11:
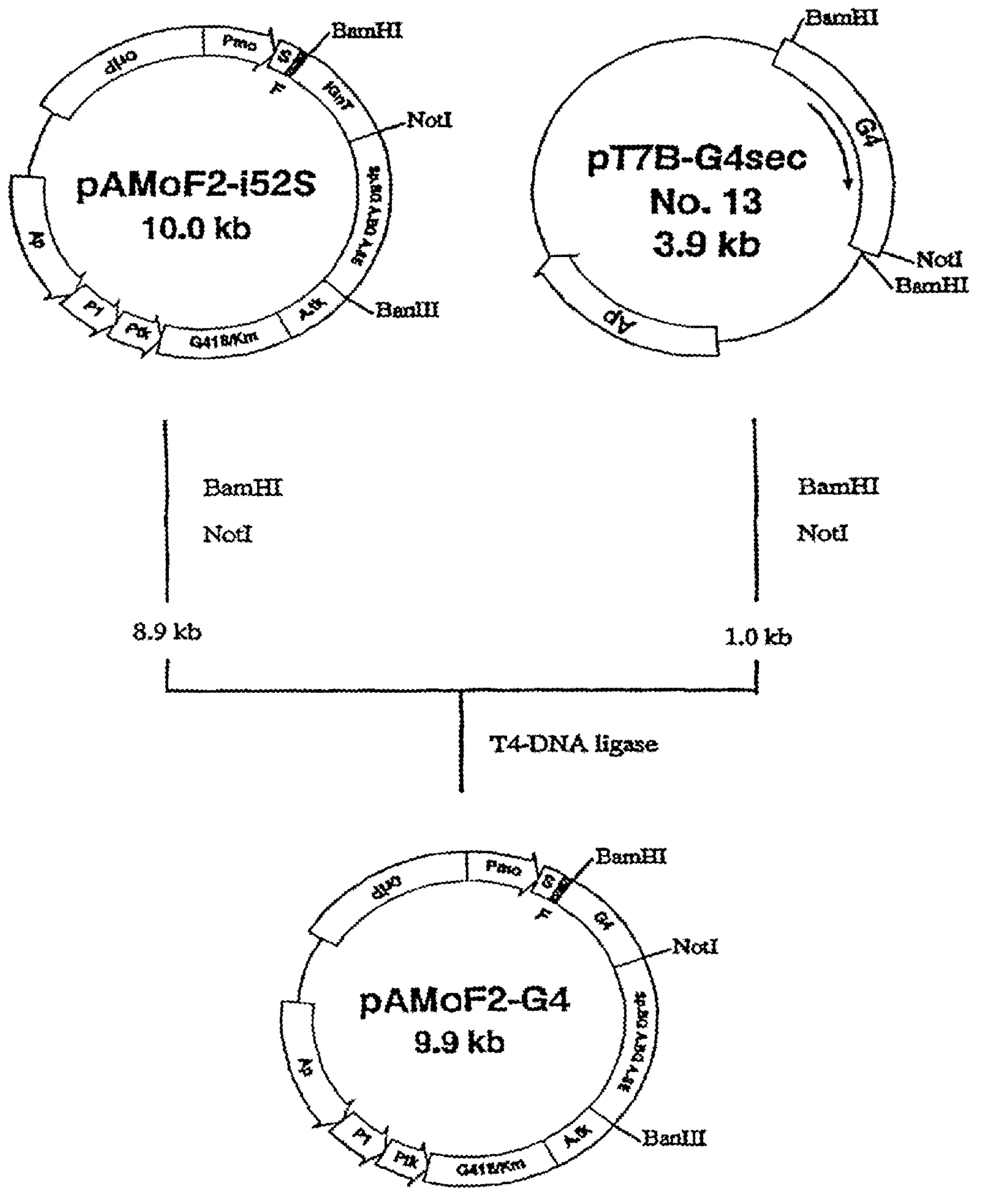
FIG. 11 is a graph showing construction steps of a plasmid pAMoF2-G4.

(3) Construction of a Plasmid pAMoF2-G4 for Secreted Expression of FLAG Peptide-Fused G4 Polypeptide (cf. FIG. 11)

It was considered based on its primary sequence that the cloned β1,3-N-acetylglucosaminyltransferase (G4) comprises an N-terminal cytoplasmic region containing 11 amino acids, a subsequent membrane-binding region rich in hydrophobic nature containing 21 amino acids, a stem region containing at least 12 amino acids and the remaining C-terminal pert comprising most of the polypeptide containing a catalytic region.

Accordingly, secreted expression of the G4 polypeptide was attempted by removing the N-terminal cytoplasmic region containing 11 amino acids, the membrane-binding region containing 21 amino acids and a part of the stem region (5 amino acids), and adding an immunoglobulin signal sequence and the FLAG peptide to the removed regions.

First, a plasmid pT7B-G4sec was constructed by preparing a DNA region encoding a region considered to have the catalytic activity of G4 polypeptide (from the 38th glutamic acid to the 372nd tyrosine in SEQ ID NO:2) by PCR and then inserting it into a T-vector pT7Blue (manufactured by Novagen). A specific method is described below.

G4-SF and G4-SR (their sequences are shown in SEQ ID NOs:26 and 27) were synthesized as primers for PCR (they can also be purchased from Sawaday Technology).

PCR was carried out using a kit manufactured by TaKaRa (GeneAmp™ DNA Amplification Reagent Kit with AmpliTaq™ Recombinant Taq DNA Polymerase). The reaction solution was prepared in accordance with the method of the kit, and 10 cycles of a reaction at 94° C. for 30 seconds, 65° C. for 1 minute and 72° C. for 2 minutes, and subsequent reaction at 72° C. for 7 minutes were carried out using a DNA thermal cycler (PERKIN ELMER CETUS DNA Thermal Cycler; available from TaKaRa). As a template, 20 ng of the plasmid pBS-G4 constructed in Example 3 was used.

A reaction solution was subjected to agarose gel electrophoresis to recover a DNA fragment of about 1.0 kb. A plasmid pT7B-G4sec (No. 13) was constructed by inserting the DNA fragment into a T-vector pT7Blue (manufactured by Novagen).

The absence of errors by the PCR was confirmed by determining nucleotide sequence of the DNA fragment inserted into pT7B-G4sec (No. 13).

Since the primers are designed such that a BamHI site is generated in G4-SF, and a NotI site in G4-SR, a PCR-amplified fragment moiety can be cut out by digesting pT7B-G4sec (No. 13) with restriction enzymes BamHI and NotI. By digesting pT7B-G4sec (No. 13) with restriction enzymes BamHI and NotI, a BamHI-NotI fragment of 1.0 kb encoding a region considered to have the catalytic activity of G4 polypeptide (from the 38th glutamic acid to the 372nd tyrosine in SEQ ID NO:2) was obtained. On the other hand, a BamHI-NotI fragment of 8.9 kb was obtained by digesting the plasmid pAMoF2-i52S with restriction enzymes BamHI and NotI. By linking these two fragments, pAMoF2-G4 was constructed (FIG. 11).

(4) Secreted Production of FLAG Peptide-Fused G4 Polypeptide in Namalwa KJM-1 Cell A control plasmid pAMoF2 and a plasmid pAMoF2-G4 for secretion expression of FLAG peptide-fused G4 polypeptide constructed in the above were prepared using a plasmid preparation kit manufactured by Qiagen (/plasmid/maxi kit; trademark number 41031).

The thus prepared plasmid was subjected to ethanol precipitation and then dissolved in TE buffer to give a concentration of 1 μg/μl.

A stable transformant was obtained by introducing each plasmid into Namalwa KJM-1 cell by the method described in Example 7.

The thus obtained transformant was suspended in 30 ml of RPMI 1640 medium containing 0.5 mg/ml G418 and 2% fetal calf serum to give a density of $5\times10^4$ cells/ml, followed by culturing at 37° C. for 10 days in a $CO_2$ incubator.

After culturing, the cells were removed by centrifugation at 160×g for 10 minutes and 1,500×g for minutes to recover the supernatant. The culture supernatant can be stored at −80° C. and used by thawing it when used.

Since a β1,3-N-acetylglucosaminyltransferase encoded by the plasmid pAMoF2-G4 is expressed as a secreted form fused with the FLAG peptide, it can be easily purified using Anti-FLAG M1 Affinity Gel (manufactured by Cosmo Bio).

To the culture supernatant obtained in the above, sodium azide, sodium chloride and calcium chloride were added to give final concentrations of 0.1%, 150 mmol/l and 2 mmol/l, respectively, and then 30 μl of Anti-FLAG M1 Affinity Gel (manufactured by Cosmo Bio) was added thereto, followed by gently stirring overnight at 4° C. After stirring, Anti-FLAG M1 Affinity Gel was recovered by centrifugation at 160×g for 10 minutes, and the gel was washed twice with 1 ml of a buffer containing 50 mmol/l Tris-HCl (pH 7.4), 150 mmol/l sodium chloride and 1 mmol/l calcium chloride.

After washing, the gel was treated at 4° C. for 30 minutes by adding 30 μl of a buffer containing 50 mmol/l Tris-HCl (pH 7.4), 150 mmol/l sodium chloride and 2 mmol/l EDTA to thereby elute the protein adsorbed to the gel. Thereafter, a supernatant was obtained by centrifugation at 160×g for 10 minutes. The gel was again mixed with 30 μl of the buffer containing 50 mmol/l of Tris-HCl (pH 7.4), 150 mmol/l of sodium chloride and 2 mmol/l of EDTA, treated at 4° C. for 10 minutes and then centrifuged at 160×g for 10 minutes to obtain the supernatant. Thereafter, this step was repeated again to carry out the elution step three times. To the eluate was added 1 mol/l calcium chloride to give a final concentration of 4 mmol/l.

(5) Measurement of a β1,3-N-Acetylglucosaminyltransferase Activity of a FLAG Peptide-Fused G4 Polypeptide A β1,3-N-acetylglucosaminyltransferase activity of FLAG peptide-fused G4 polypeptide expressed as a secreted form in Namalwa KJM-1 cell was measured by using 15 μl of the eluate prepared in the above (4). The method of Example 8 was used in the activity measurement. As a result, a β1,3-N-acetylglucosaminyltransferase activity was detected when the eluate derived from the culture supernatant of pAMoF2-G4-introduced Namalwa KJM-1 cell was used. The ratio of the substrate converted into the product was 0.51%. On the other hand, the activity was not detected when the eluate derived from the culture supernatant of Namalwa KJM-1 cell transformed by the vector pAMoF2 was used.

Based on the above result, it was shown that the FLAG peptide-fused G4 polypeptide expressed as a secreted form in Namalwa KJM-1 cell has a β1,3-N-acetylglucosaminyltransferase activity. The result shows that a β1,3-N-acetylglucosaminyltransferase (G4) can be produced as a secreted form fused with FLAG peptide in animal cell and that the produced fusion protein can be easily purified using Anti-FLAG M1 Affinity Gel. It also shows that synthesis of sugar chains can be made by using the produced fusion protein.

Example 10

Secreted Production of a FLAG Peptide-Fused β1,3-N-Acetylglucosaminyltransferase (G4) by Using Insect Cell as a Host Secreted expression of the FLAG peptide-fused G4 polypeptide shown in Example 8 in an insect cell was carried out.

(1) Production of a Recombinant Virus for Secreted Expression of the FLAG Peptide-Fused G4 Polypeptide in an Insect Cell A recombinant virus was produced by two steps comprising a step (step 1) in which a DNA encoding the protein of interest is inserted into a specific plasmid which is called a transfer vector and a step (step 2) in which the DNA-inserted transfer vector prepared in the step 1 and a wild type virus are co-transfected into an insect cell to obtain the recombinant virus by homologous recombination. The steps were carried out by the following procedure by using BaculoGold Starter Kit manufactured by PharMingen (product number PM-21001K).

Figure 12:
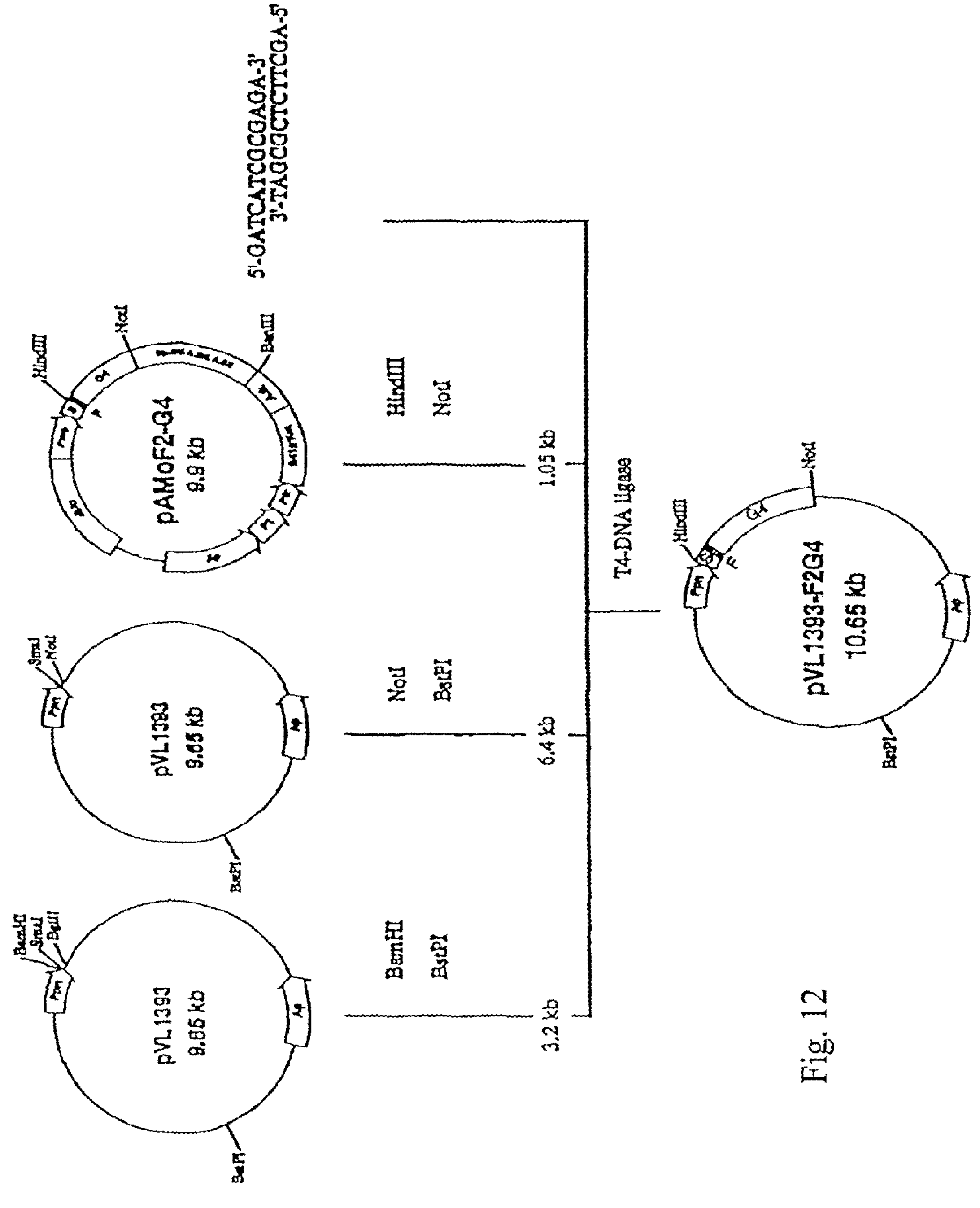
FIG. 12 is a graph showing construction steps of a plasmid pVL1393-F2G4.

Step 1 Insertion of a DNA Encoding a Secretable FLAG Peptide-Fused G4 Polypeptide into Transfer Vector (FIG. 12)

A plasmid pVL1393-F2G4 was constructed by inserting a DNA encoding the FLAG peptide-fused secretory G4 polypeptide shown in Example 9 between BamHI site and NotI site of a transfer vector pVL1393 (manufactured by PharMingen).

pAMoF2-G4 prepared in Example 9 was digested with restriction enzymes HindIII and NotI to obtain a HindIII-NotI fragment of 1.05 kb.

pVL1393 origin was digested with restriction enzymes BamHI and BstPI to obtain a BamHI-BstPI fragment of 3.2 kb.

pVL1393 origin was digested with restriction enzymes NotI and BstPI to obtain a NotI-BstPI fragment of 6.4 kb.

DNAs shown in SEQ ID NOs:28 and 29 were synthesized as linkers for linking BamHI site and HindIII site, and 5'-end phosphorylation was carried out using T4 polynucleotide kinase.

pVL1393-F2G4 was constructed by linking these three fragments and linkers (FIG. 12).

Step 2 Preparation of a Recombinant Virus

A recombinant baculovirus was prepared in the following manner by introducing a filamentous baculovirus DNA (BaculoGold baculovirus DNA, manufactured by PharMingen) and the above plasmid pVL1393-F2G4 into an insect cell Sf9 (manufactured by PharMingen) cultured in TNM-FH insect medium (manufactured by PharMingen), by the lipofectin method [*Protein, Nucleic Acid and Enzyme,* 37, 2701 (1992)].

After dissolving 1 to 5 μg of pVL1393-F2G4 and 15 ng of the filamentous baculovirus DNA in 12 μl of distilled water, a mixture of 6 μl (6 μg) of lipofectin (manufactured by GIBCO BRL) with 6 μl of distilled water was added thereto and allowed to stand at room temperature for 15 minutes.

About $2\times10^6$ of Sf9 cells were suspended in 2 ml of Sf900-II medium (manufactured by GIBCO BRL), and put into a cell culture plastic dish having a diameter of 35 mm, and an entire volume of the mixed solution of pVL1393-F2G4, filamentous baculovirus DNA and lipofectin was added thereto, followed by culturing at 27° C. for 3 days.

One milliliter of culture supernatant containing a recombinant virus was collected from the culture.

One milliliter of the TNM-FH insect medium was newly added to the dish after obtaining the culture supernatant, followed by further culturing at 27° C. for 4 days. After culturing, 1.5 ml of culture supernatant containing the recombinant virus was collected in the same manner.

(2) Acquisition of a Recombinant Virus Solution

About $8\times10^6$ of Sf9 cells were suspended in 5 ml of EX-CELL 400 medium (manufactured by JRH), put into a 25 $cm^2$ flask (manufactured by GREINER) and allowed to stand at room temperature for 30 minutes to adhere the cells to the flask, and then the supernatant was discarded and 1 ml of EX-CELL 400 medium and 1 ml of the recombinant virus-containing culture supernatant obtained in the above (1) were added to the resulting flask.

After the addition, the cells and virus particles were thoroughly brought into contact by gently shaking at room temperature for 1 hour and then 4 ml of the TNM-FH insect medium was added thereto, followed by culturing at 27° C. for 4 days.

By centrifuging the culture at 1,500×g for 10 minutes, recombinant virus-infected Sf9 cells and 5.5 ml of a solution containing recombinant virus particles were obtained.

About $2\times10^7$ of Sf9 cells were suspended in 15 ml of EX-CELL 400 medium, put into a 75 $cm^2$ flask (manufactured by GREINER) and allowed to stand at room temperature for 30 minutes to adhere the cells to the flask, and then the supernatant was discarded and 5 ml of EX-CELL 400 medium and 1 ml of the recombinant virus solution obtained in the above were added to the resulting flask.

After the addition, the cells and virus particles were thoroughly brought into contact by gently shaking at room temperature for 1 hour and then 10 ml of the TNM-FH insect medium was added thereto, followed by culturing at 27° C. for 4 days. By centrifuging the culture at 1,500×g for 10 minutes, recombinant virus-infected Sf9 cells and 15 ml of a solution containing recombinant virus particles were obtained.

The virus titer of the recombinant virus solution can be calculated by the following method (BaculoGold Starter Kit Manual provided by PharMingen).

About $6\times10^7$ of Sf9 cells are suspended in 4 ml of EX-CELL 400 medium, put into a cell culture plastic dish of 60 mm in diameter and allowed to stand at room temperature for 30 minutes to adhere the cells to the dish, and then the supernatant is discarded and 400 μl of EX-CELL 400 medium and 100 μl of the recombinant virus solution diluted to $10^{-4}$ or $10^{-5}$ with EX-CELL 400 medium are added to the resulting dish.

After the addition, the cells and virus particles are thoroughly brought into contact by gently shaking the dish at room temperature for 1 hour.

After the contact, the medium is removed from the dish, and a mixed solution of 2 ml of EX-CELL 400 medium containing 2% low melting point agarose (Agarplaque Agarose, manufactured by PharMingen) (kept at 42° C.) with 2 ml of TNM-FH Insect Medium (kept at 42° C.) is poured into the dish and allowed to stand at room temperature for 15 minutes.

After standing, the dish is wrapped with a vinyl tape in order to prevent drying, and the resulting dish is put into a sealable plastic container, followed by culturing at 27° C. for 5 days.

After culturing, 1 ml of PBS buffer containing 0.01% Neutral Red is added to the dish, followed by culturing for 1 day, and then the number of formed plaques is counted.

(3) Secreted Production and Purification of a FLAG Peptide-Fused G4 Polypeptide

Since the G4 polypeptide encoded by the recombinant virus derived from a plasmid pVL1393-F2G4 is expressed as a secreted form fused with FLAG peptide, it can be easily purified using Anti-FLAG M1 Affinity Gel (manufactured by Cosmo Bio).

About $2\times10^7$ of Sf21 cells were suspended in 15 ml of EX-CELL 400 medium, put into a 75 $cm^2$ flask (manufactured by GREINER) and allowed to stand at room temperature for 30 minutes to adhere the cells to the flask, and then the supernatant was discarded and 4 ml of EX-CELL 400 medium and 1 ml of the recombinant virus solution obtained in the above (2) were added to the resulting flask.

After the addition, the cells and virus particles were thoroughly brought into contact by gently shaking at room temperature for 1 hour, and then 10 ml of the TNM-FH insect medium was added thereto, followed by culturing at 27° C. for 4 days. By centrifuging the culture at 1,500×g for 10 minutes, 15 ml of a culture supernatant possibly containing the secreted G4 was obtained.

To 30 ml of the culture supernatant obtained in the above, sodium azide, sodium chloride and calcium chloride were added to give final concentrations of 0.1%, 150 mmol/l and 2 mmol/l, respectively, and then the mixture was mixed with 30 μl of Anti-FLAG M1 Affinity Gel (manufactured by Cosmo Bio), followed by gently stirring overnight at 4° C.

After stirring, Anti-FLAG M1 Affinity Gel was recovered by 10 minutes of centrifugation at 160×g, and the gel was washed twice with 1 ml of a buffer containing mmol/l of Tris-HCl (pH 7.4), 150 mmol/l of sodium chloride and 1 mmol/l of calcium chloride.

After the washing, the gel was treated at 4° C. for 30 minutes by adding 80 μl of a buffer containing 50 mmol/l Tris-HCl (pH 7.4), 150 mmol/l sodium chloride and 2 mmol/l EDTA to thereby elute the protein adsorbed to the gel. Thereafter, a supernatant was obtained by centrifugation at 160×g for 10 minutes. The gel was again mixed with 80 μl of the buffer containing 50 mmol/l Tris-HCl (pH 7.4), 150 mmol/l sodium chloride and 2 mmol/l EDTA, treated at 4° C. for 10 minutes, followed by centrifuging at 160×g for 10 minutes to obtain the supernatant. Thereafter, this step was repeated again to carry out the elution step three times. To the eluate, 1 mol/l calcium chloride was added to give a final concentration of 4 mmol/l.

Figure 13:
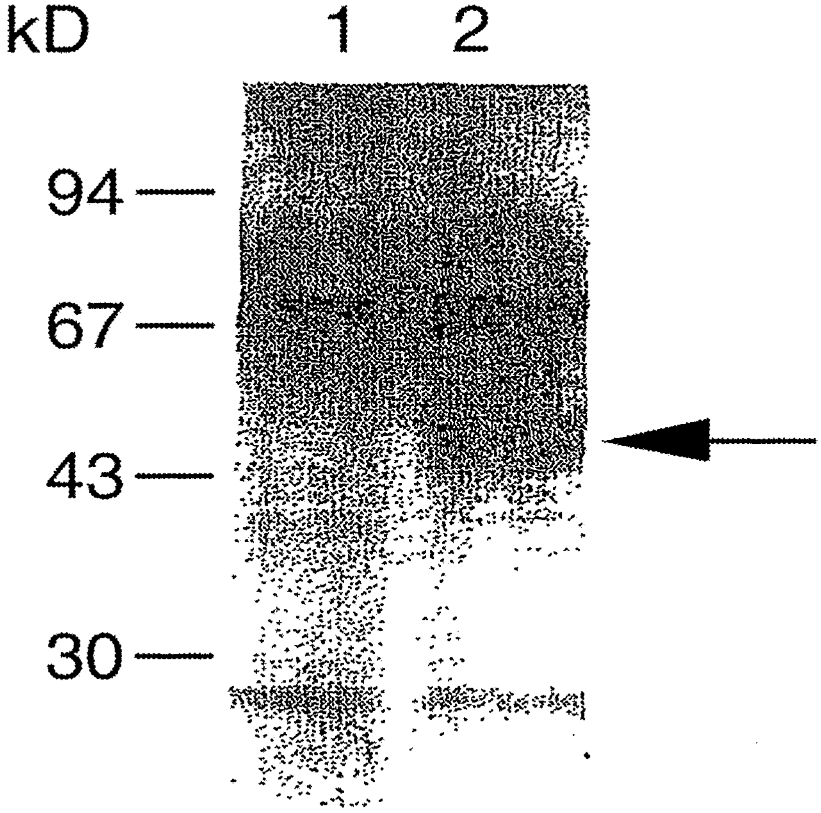
FIG. 13 is a graph showing a result obtained by purifying FLAG peptide-fused secreted G4 from a culture supernatant of Sf21 cell infected with a recombinant virus derived from a plasmid pVL1393-F2G4 by using Anti-FLAG M1 Affinity gel, and then subjecting it to SDS polyacrylamide gel electrophoresis (lane 2). As a control, a sample was prepared from a culture supernatant of Sf21 cell infected with a recombinant virus derived from a plasmid pVL1393 in the same manner and then subjected to SDS polyacrylamide gel electrophoresis (lane 1). The arrow shows the position of the produced secreted G4 polypeptide.

SDS-PAGE was carried out by using 15 μl of the thus prepared eluate, and then staining was carried out by using Coomassie Brilliant Blue (FIG. 13).

When the eluate prepared from the culture supernatant of Sf21 infected with the recombinant virus derived from pVL1393-F2G4 was used, a broad band ranging from 43 to 48 kD was found. On the other hand, such a band was not detected when the eluate prepared from the culture supernatant of Sf21 infected with the recombinant virus derived from a vector pVL1393 was used.

Based on the above result, it was shown that the FLAG peptide-fused G4 polypeptide is produced as a secreted form in culture supernatant and can be purified easily using Anti-FLAG M1 Affinity Gel.

(4) Measurement of β1,3-N-Acetylglucosaminyltransferase Activity of the FLAG Peptide-Fused G4 Polypeptide A β1,3-N-acetylglucosaminyltransferase activity of FLAG peptide-fused G4 polypeptide produced as a secreted form in the insect cell was measured using 15 μl of the eluate prepared in the above (3). The method of Example 8 was used for the activity measurement. As a result, a β1,3-N-acetylglucosaminyltransferase activity was detected when the eluate derived from the culture supernatant of the insect cell transformed by pVL1393-F2G4 was used. The ratio of the substrate converted into the product was 12.1%.

A β1,3-N-acetylglucosaminyltransferase activity was also detected when the resin before elution was used. The ratio of the substrate converted into the product was 21.0%. The result shows that a sugar chain can be synthesized even under conditions in which the enzyme is adsorbed to the resin.

On the other hand, the activity was not detected when the eluate derived from the culture supernatant of the insect cell introduced with a vector pVL1393 was used.

Based on the above result, it was shown that the FLAG peptide-fused G4 polypeptide expressed as a secreted form in the insect cell has a β1,3-N-acetylglucosaminyltransferase activity. The result shows that a β1,3-N-acetylglucosaminyltransferase (G4) can be produced as a secreted form fused with FLAG peptide in insect and that the produced fusion protein can be easily purified using Anti-FLAG M1 Affinity Gel. It also shows that synthesis of sugar chains can be made by using the produced fusion protein.

It was found from these results that the productivity is high when produced in the insect cell in comparison with the case of producing in Namalwa KJM-1 cell.

Example 11

Examination on the Substrate Specificity of a Secretory β1,3-N-Acetylglucosaminyltransferase (Secretory G4)

Examination on the substrate specificity of a β1,3-N-acetylglucosaminyltransferase (G4) was carried out by using the FLAG peptide-fused G4 polypeptide produced as a secreted form in Example 10.

(1) Analysis Using Pyridylaminated Oligosaccharides as Substrates

The method shown in Example 8 was used as the activity measuring method. Specifically, after the reaction at 37° C. for 14.5 hours in 30 μl of an assay solution [200 mmol/l of MOPS (pH 7.5), 20 mmol/l of UDP-GlcNAc (SIGMA), 20 mmol/l of $MnCl_2$, 50 μmol/l of pyridylaminated sugar chain substrate and 15 μl of the above eluate], products were detected by HPLC. As substrates, LNnT, lacto-N-tetraose (Galβ1-3GlcNAcβ1-3Galβ1-4Glc, hereinafter referred to as "LNT"), lacto-N-fucopentaose III (Galβ1-3(Fucα1-4)GlcNAβ1-3Galβ1-4Glc, hereinafter referred to as "LNFP-II"), lacto-N-fucopentaose III (Galβ1-4(Fucα1-3)GlcNAβ1-3Galβ1-4Glc, hereinafter referred to as "LNFP-III"), lacto-N-fucopentaose V (Galβ1-3GlcNAβ1-3Galβ1-4(Fucα1-3)Glc, hereinafter referred to as "LNFP-V") and lacto-N-difucohexaose II (Galβ1-3(Fucα1-4)GlcNAβ1-3Galβ1-4(Fucα1-3)Glc, hereinafter referred to as "LNDFH-II") (all manufactured by Oxford Glycosystems) were used after fluorescently labeling them with aminopyridine. Fluorescence labeling of these substrates were carried out in accordance with the usual method [*Agric. Biol. Chem.,* 54, 2169 (1990)].

For each substrate, the reaction was carried using the assay solution with or without UDP-GlcNAc (sugar donor), and then HPLC was carried out and peaks appeared only in the assay solution containing UDP-GlcNAc were defined as products.

The assay solution after completion of the reaction was treated at 100° C. for 5 minutes and then centrifuged at 10,000×g for 5 minutes, and a portion (5 μl) of the thus obtained supernatant was applied to HPLC.

The HPLC was carried out by using TSK-gel ODS-80Ts column (4.6×300 mm; Tosoh); 0.02 mol/l ammonium acetate buffer (pH 4.0) was used as the eluate at an elution temperature of 50° C. and at a flow rate of 0.5 ml/min.

Products were detected by using a fluorescence spectrum photometer FP-920 (JASCO Corporation) (excitation wavelength 320 nm, radiation wavelength 400 nm).

Relative activities when the activity on LNnT used as a substrate is defined as 100% are shown in Table 1. When LNnT was used as a substrate, the conversion ratio of the substrate into the product was 12.9%. It was found that the β1,3-N-acetylglucosaminyltransferase (G4) uses LNT and LNFP-V as a good substrate in addition to LNnT. It is known that already known β1,3-N-acetylglucosaminyltransferases use LNnT as a good substrate but hardly use LNT as a substrate [*J. Biol. Chem.,* 268, 27118 (1993), *Proc. Natl. Acad. Sci. USA,* 96, 406 (1999)]. In consequence, it was found that a β1,3-N-acetylglucosaminyltransferase (G4) is an enzyme having a substrate specificity which is clearly different from that of the already known β1,3-N-acetylglucosaminyltransferases.

It is known that a cancer-related sugar chain having dimeric Lewis a sugar chain antigen [Galβ1-3(Fucα1-4)GlcNAβ1-3Galβ1-3(Fucα1-4)GlcNAc] is expressed in large bowel cancer tissues and large bowel cancer cell lines, for example, the presence of a glycolipid having a structure of Galβ1-3(Fucα1-4)GlcNAβ1-3Galβ1-3(Fucα1-4)GlcNAβ1-3Galβ1-3Glc-Cer has been found [*J. Biol. Chem.,* 266, 8439-8446 (1991)]. Since the β1,3-N-acetylglucosaminyltransferase (G4) can efficiently transfer N-acetylglucosamine to the terminal galactose residue of the Galβ1-3GlcNAc structure too, it is considered that a β1,3-N-acetylglucosaminyltransferase (G4), but not the already known β1,3-N-acetylglucosaminyltransferases involved in the synthesis of the core sugar chain of the dimeric Lewis a sugar chain. As will be described later in Example 13(3) in detail, the G4 transcription products are highly expressed in a large bowel cancer cell line.

TABLE 1

| Substrate specificity of a β1,3-N-acetylglucosaminyltransferase (G4) with pyridylaminated oligosaccharides as substrates | | |
|---|---|---|
| Substrate | Sugar chain structure | Relative activity (%) |
| LNnT | Galβ1-4GlcNAcβ1-3Galβ1-4Glc | 100 |
| LNFP-III | Galβ1-4(Fucα1-3)GlcNAcβ1-3Galβ1-4Glc | 4.7 |
| LNT | Galβ1-3GlcNAcβ1-3Galβ1-4Glc | 84.5 |
| LNFP-II | Galβ1-3(Fucα1-4)GlcNAcβ1-3Galβ1-4Glc | 0 |
| LNFP-V | Galβ1-3GlcNAcβ1-3Galβ1-4(Fucα1-3)Glc | 65.1 |
| LNDFH-II | Galβ1-3(Fucα1-4)GlcNAcβ1-3Galβ1-4(Fucα1-3)Glc | 0 |

(2) Analysis Using Unlabeled Oligosaccharides as Substrates

The reaction using the glycosyltransferase was carried out as follows. The reaction was carried out at 37° C. for 16 hours in 40 μl of an assay solution [50 mmol/l MOPS (pH 7.5), 5 mmol/l UDP-GlcNAc (SIGMA), 5 mmol/l $MnCl_2$, 10 mmol/l sugar chain substrate and 10 μl of the above eluate]. Next, the reaction solution was treated at 100° C. for 5 minutes and then centrifuged at 10,000×g for 20 minutes to obtain the supernatant, and a portion thereof was analyzed using HPAE/PAD (High Performance Anion Pulsed Amperometoric Detection; manufactured by DIONEX). The specific method was carried out in the usual way [*Anal. Biochem.,* 189, 151 (1990), *J. Biol. Chem.,* 273, 433 (1998)].

As substrates, the following unlabeled oligosaccharides were used: lactose (Galβ1-4Glc), N-acetyllactosamine (Galβ1-4GlcNAc, hereinafter referred to as "LacNAc" in some cases), LNnT, LNT and lacto-N-neohexaose (Galβ1-4GlcNAcβ1-3Galβ1-4GlcNAcβ1-3Galβ1-4Glc, hereinafter referred to as "LNnH").

For each substrate, the reaction was carried using the assay solution with or without UDP-GlcNAc (sugar donor), and then HPLC was carried out and peaks appeared only in the assay solution containing UDP-GlcNAc were defined as products.

In identifying the product, coincidence of its elution time with that of a standard sugar chain was used as the index. As the standard sugar chains, GlcNAcβ1-3Galβ1-4Glc, GlcNAcβ1-3Galβ1-4GlcNAc and GlcNAcβ1-3Galβ1-4GlcNAcβ1-3Galβ1-4Glc were used.

Relative activities when the activity on LNnT used as a substrate is defined as 100% are shown in Table 2. When LNnT was used as a substrate, the conversion ratio of the substrate into the product was 1.7%. It was found that the β1,3-N-acetylglucosaminyltransferase (G4) uses LNT, LNnH and Galβ1-4Glc as good substrates in addition to LNnT. On the other hand, it did not use Galβ1-4GlcNAc as a substrate. It is known that already known β1,3-N-acetylglucosaminyltransferases use both Galβ1-4Glc and Galβ1-4GlcNAc as good substrates [*J. Biol. Chem.,* 268, 27118 (1993), *Proc. Natl. Acad. Sci. USA,* 96, 406 (1999)]. In consequence, it was found that a β1,3-N-acetylglucosaminyltransferase (G4) is an enzyme having a substrate specificity which is clearly different from that of the already known enzymes.

TABLE 2

| Substrate specificity of a β1,3-N-acetylglucosaminyltransferase (G4) with unlabeled oligosaccharides as substrates | | |
|---|---|---|
| Substrate | Sugar chain structure | Relative activity (%) |
| LNnT | Galβ1-4GlcNAcβ1-3Galβ1-4Glc | 100 |
| LNT | Galβ1-3GlcNAcβ1-3Galβ1-4Glc | 114 |
| LNnH | Galβ1-4GlcNAcβ1-3Galβ1-4GlcNAcβ1-3Galβ1-4Glc | 45 |
| Lactose | Galβ1-4Glc | 235 |
| LacNAc | Galβ1-4GlcNAc | 0 |

On the other hand, when β1,3-galactosyltransferase activity of the secretory G4 was measured by using GlcNAc and GlcNAβ1-3Galβ1-4Glc as receptor substrates, the activity was not detected.

The glycosyltransferase reaction was carried out as follows. The reaction was carried out at 37° C. for 16 hours in 40 μl of an assay solution [50 mmol/l MOPS (pH 7.5), 5 mmol/l UDP-GlcNAc (SIGMA), 5 mmol/l $MnCl_2$, 10 mmol/l of a sugar chain substrate and 10 μl of the above eluate]. Next, the reaction solution was treated at 100° C. for 5 minutes and then centrifuged at 10,000×g for 20 minutes to obtain the supernatant, and a portion thereof was analyzed by using HPAE/PAD (High Performance Anion Pulsed Amperometoric Detection; manufactured by DIONEX). The specific method was carried out in the usual way [*Anal. Biochem.,* 189, 151 (1990), *J. Biol. Chem.,* 273, 433 (1998)].

Example 12

Synthesis of a Poly-N-Acetyllactosamine Sugar Chain Using Secretory β1,3-N-Acetylglucosaminyltransferase (Secretory G4)

Synthesis of poly-N-acetyllactosamine sugar chain was carried out by using the FLAG peptide-fused G4 polypeptide produced as a secreted form in Example 10 and β1,4-galactosyltransferase.

(1) Two Step Reaction

By allowing the FLAG peptide-fused G4 polypeptide produced as a secreted form in Example 10 to react with LNnT, a sugar chain in which N-acetylglucosamine was added via a β1,3-linkage to the non-reducing terminal galactose residue of LNnT (GlcNAcβ1-3Galβ1-4GlcNAcβ1-3Galβ1-4Glc) was synthesized. Next, by allowing β1,4-galactosyltransferase (manufactured by SIGMA) purified from bovine milk to react with the sugar chain, a sugar chain in which galactose was added via a β1,4-linkage to the non-reducing terminal N-acetylglucosamine residue (Galβ1-4GlcNAcβ1-3Galβ1-4GlcNAcβ1-3Galβ1-4Glc) was synthesized. In the same manner, Galβ1-4GlcNAcβ1-3Galβ1-3GlcNAcβ1-3Galβ1-4Glc was synthesized by using LNT as a substrate. Also, Galβ1-4GlcNAβ1-3Galβ1-3GlcNAβ1-3Galβ1-4(Fucα1-3) Glc was synthesized by using LNFP-V [(Galβ1-3GlcNAβ1-3Galβ1-4(Fucα1-3)Glc) as a substrate. The specific reaction was carried out as follows.

The reaction was carried out at 37° C. for 14.5 hours in 30 μl of a reaction solution [200 mmol/l MOPS (pH 7.5), 20 mmol/l UDP-GlcNAc (SIGMA), 20 mmol/l $MnCl_2$, 50 μmol/l of a pyridylaminated sugar chain substrate and 15 μl of the above eluate]. As a substrate, LNnT, LNT or LNFP-V was used. After confirming formation of products by HPLC in the same manner as the method described in Example 11, β1,4-galactosyltransferase (20 mU) and UDP-Gal (20 mmol/l)

were added to the reaction solution and allowed to react at 37° C. for 14.5 hours. Formation of products was confirmed by HPLC.

(2) One-Pot Reaction

A sugar chain in which N-acetylglucosamine was added to the non-reducing end of the sugar chain (Galβ1-4GlcNAcβ1-3Galβ1-4GlcNAcβ1-3Galβ1-4Glc) was synthesized by allowing the FLAG peptide-fused G4 polypeptide produced as a secreted form in Example 10 to react simultaneously with LNnT and β1,4-galactosyltransferase (manufactured by SIGMA) purified from bovine milk. In the same manner, Galβ1-4GlcNAcβ1-3Galβ1-3GlcNAcβ1-3Galβ1-4Glc was synthesized using LNT as a substrate. Also, Galβ1-4GlcNAβ1-3Galβ1-3GlcNAβ1-3Galβ1-4(Fucα1-3)Glc was synthesized by using LNFP-V [(Galβ1-3GlcNAβ1-3Galβ1-4(Fucα1-3)Glc) as a substrate. The specific reaction was carried out as follows.

The reaction was carried out at 37° C. for 14.5 hours in 30 μl of a reaction solution [200 mmol/l MOPS (pH 7.5), 20 mmol/l UDP-GlcNAc (SIGMA), 20 mmol/l UDP-Gal (SIGMA), 20 mmol/l $MnCl_2$, 50 μmol/l of a pyridylaminated sugar chain substrate, 10 μl of the above eluate and 20 mU β1,4-galactosyltransferase]. As a substrate, LNnT, LNT or LNFP-V was used. Formation of products were confirmed by HPLC.

Example 13

Examination of the Expression Level of Transcripts of Each Gene for G3, G4 or G7 in Various Cells The transcription products of each gene for G3, G4 (G4-2) or G7 were determined by a semi-quantitative PCR method in accordance with a usual method [PCR Protocols, Academic Press (1990)]. Also, transcription products of β-actinconsidered to be expressed in each cell at a similar degree was simultaneously measured to thereby confirm that there are no great differences in the amount of mRNA among cells and the conversion efficiency of single-stranded cDNA from mRNA by reverse transcriptase among samples.

Transcription products of β-actin were measured by a quantitative PCR method in the usual way [*Proc. Natl. Acad. Sci. USA,* 87, 2725 (1990), *J. Biol. Chem.,* 269, 14730 (1994), Japanese Published Unexamined Patent Application No. 181759/94].

(1) Synthesis of Single-Stranded cDNAs Derived from Various Cells and Cell Lines As cell lines, colon cancer cell lines (WiDR, Colo205, SW1116, LS180, DLD-1), lung cancer cell lines (QG90, HLC-1, PC9), pancreatic cancer cell lines (Capan-1, Capan-2), a prostate cancer cell line PC-3, a gastric cancer cell line KATO III, T-cell lines (Jurkat, CCRF-CEM, HSB-2, PEER, Molt-3, Molt-4, HUT78, HPB-ALL), B-cell lines (Namalwa KJM-1, Daudi, Wa, CCRF-SB, Jiyoye, RPMI1788, RPMI8226, HO328-8, BALL-1, KOPN-K, IM-9), a melanoma cell line WM266-4, granulocyte/monocyte cell lines (THP-1, HL-60, U-937) and a neuroblastoma cell line SK-N-MC were used. QG90, HPB-ALL, Wa, SW1116 and Jurkat were obtained from Aichi Cancer Center. HLC-1 was obtained from Cancer Research Institute, Osaka University. HO328-8 was obtained from Food Chemistry, Department of Agriculture, Kyushu University. KOPN-K was obtained from Saitama Central Hospital. KATO III and PC-9 were obtained from Immune Biology Research Institute. CCRF-SB and RPMI8226 were obtained from Dainippon Pharmaceutical. BALL-1, PEER, Molt-4, Daudi, IM-9 and KY821 were obtained from JCRB. Other cells were obtained from ATCC.

Jurkat cells stimulated with phytohemagglutinin-P (PHA-P) and 12-O-tetradecanoylphorbol 13-acetate (TPA) were prepared as follows. Jurkat cells inoculated in a density of $4\times10^5$ cells/ml into RPMI 1640 medium containing 10% FCS were added with 1 μg/ml of PHA-P and 50 ng/ml of TPA, followed by culturing for 3 hours, 12 hours or 24 hours, and then the cells were recovered.

Also, polymorphonuclear leukocytes and mononuclear leukocytes were obtained by separating them from peripheral blood of a healthy adult by use of Polymorphprep™ as a kit manufactured by Nycomed Pharma. The thus obtained mononuclear leukocytes were further separated into monocyte and lymphocyte in accordance with the general method [*J. Immunol.,* 130, 706 (1983)].

Total RNA of each cell was prepared in accordance with the general method [*Biochemistry.,* 18, 5294 (1977)]. Single-stranded cDNA was synthesized from the total RNA using a kit (SUPER™ Preamplification System; manufactured by BRL). Single-stranded cDNA samples were synthesized from 5 μg of total RNA regarding the cell lines, and from 1 μg of total RNA regarding the leukocytes, and diluted 50 times and 10 times, respectively with water to be used as templates of PCR. As primers, an oligo(dT) primer or random primers were used. Regarding SK-N-MC, SK-N-SH, Colo205, SW1116, LS180, DLD-1, Capan-1 and Capan-2, random primers were used. An Oligo(dT) primer was used in other cases.

Also, single-stranded cDNAs were synthesized from mRNA preparations (manufactured by Clontech) derived from various human organs. Single-stranded cDNAs were synthesized from 1 μg of mRNA, diluted 240 times with water and used as a template of PCR. As a primers, an oligo(dT) primers was used. As mRNAs, mRNAs derived from the following 35 organs were used; 1: adrenal gland; 2: brain; 3: caudate nucleus; 4: hippocampus; 5: substantia nigra; 6: thalamus; 7: kidney; 8: pancreas; 9: pituitary gland; 10: small intestine; 11: bone marrow; 12: amygdala; 13: cerebellum; 14: callosal body; 15: fetal brain; 16: fetal kidney; 17: fetal liver; 18: fetal lung; 19: heart; 20: liver; 21: lung; 22: lymph node; 23: mammary gland; 24: placenta; 25: prostate; 26: salivary gland; 27: skeletal muscle; 28: spinal cord; 29: spleen; 30: stomach; 31: testis; 32: thymus; 33: thyroid; 34: trachea; and 35: uterus.

(2) Preparation of Standard and Internal Control for Quantitative PCR

Each of pBS-G3, pBS-G4-2 and pT7B-G7 was converted into linear DNA by digesting it with restriction enzymes capable of cutting out the cDNA moiety and then used as the standard for the determination. After confirming complete cutting of each plasmid, it was used by diluting it stepwise with water containing 1 μg/ml yeast transfer RNA. Specifically, pBS-G3 was digested with NotI and SalI, pBS-G4-2 with NotI and pT7B-G7 with HincII and SmaI.

Also, each of pUC119-ACT and pUC119-ACTd was converted into linear DNA by digesting it with restriction enzymes (HindIII and Asp718) capable of cutting out the cDNA moiety and then used respectively as the standard and internal control for the determination of transcription product of β-actin [*J. Biol. Chem.,* 269, 14730 (1994), Japanese Published Unexamined Patent Application No. 181759/94]. After confirming complete cutting of each plasmid, it was used by diluting it stepwise with water containing 1 μg/ml yeast transfer RNA.

(3) Determination of the Amount of Transcripts of Each Gene for G3, G4 or G7 by PCR PCR was carried out by using each single-stranded cDNAs prepared in the above (1) from various cells and cell lines as a template. As primers for PCR, F-3-5 and R-3-5 were used for detecting G3 transcription product, and F-4-5 and R-4-5 for detecting G4 transcription product and F-7-3a (SEQ ID NO:30) and R-7-3a for detecting G7 transcript. Also, a calibration curve was prepared by carrying out PCR in the same manner by using the standard prepared in the above (2) as templates.

The PCR was carried out by using Recombinant Taq DNA Polymerase (Gene Taq) manufactured by Nippon Gene, and 10× Gene Taq Universal Buffer and 2.5 mmol/l dNTP Mixture attached thereto, in accordance with the instructions. The reaction was carried out by using 20 μl of a reaction solution to which dimethyl sulfoxide was added to give a final concentration of 5%.

The reaction solution (19 μl) containing respective components other than Taq DNA polymerase was treated at 97° C. for 3 minutes by using a thermal cycler (DNA Enzine PTC-200 Peltier Thermal Cycler) manufactured by MJ RESEARCH and then rapidly cooled in ice. Next, 1 μl of 1/5-diluted Taq DNA polymerase was added to the reaction solution and then the reaction of 94° C. for 30 seconds, 60° C. for 1 minute and 72° C. for 2 minutes was repeated 26 to 30 cycles by using the thermal cycler of MJ RESEARCH. A portion (7 μl) of the reaction solution was subjected to agarose gel electrophoresis and then the gel was stained with SYBR Green I nucleic acid stain (manufactured by Molecular Probes). The amounts of the amplified DNA fragments were measured by analyzing patterns of the amplified DNA fragments by a fluoro imager (FluorImager SI; manufactured by Molecular Dynamics). In order to determine the amount of transcripts more accurately, similar PCR was carried out by changing the number of cycles of PCR. The amount of the standard was changed depending on the number of cycles of PCR.

The amount of β-actin transcript was determined in the same manner as described in literatures [*J. Biol. Chem.*, 269, 14730 (1994), Japanese Published Unexamined Patent Application No. 181759/94].

Figure 14:
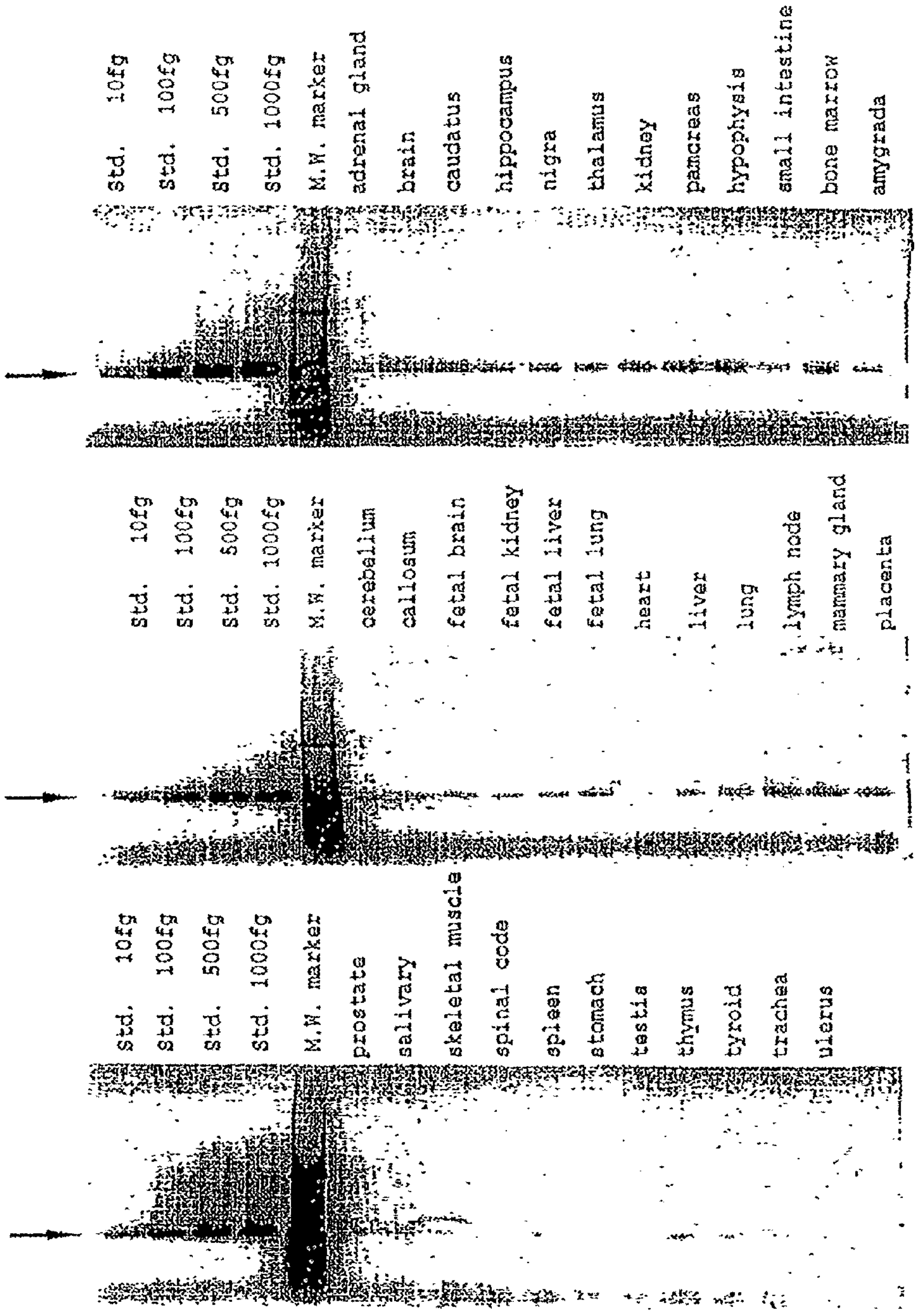
FIG. 14 is an electrophoresis pattern showing a result of the examination of the expression level of G3 transcript in 35 kinds of human organs, using a PCR method. The number of cycles of the PCR is 26. The arrow shows the position of the amplified fragment of target (564 bp).
Figure 15:
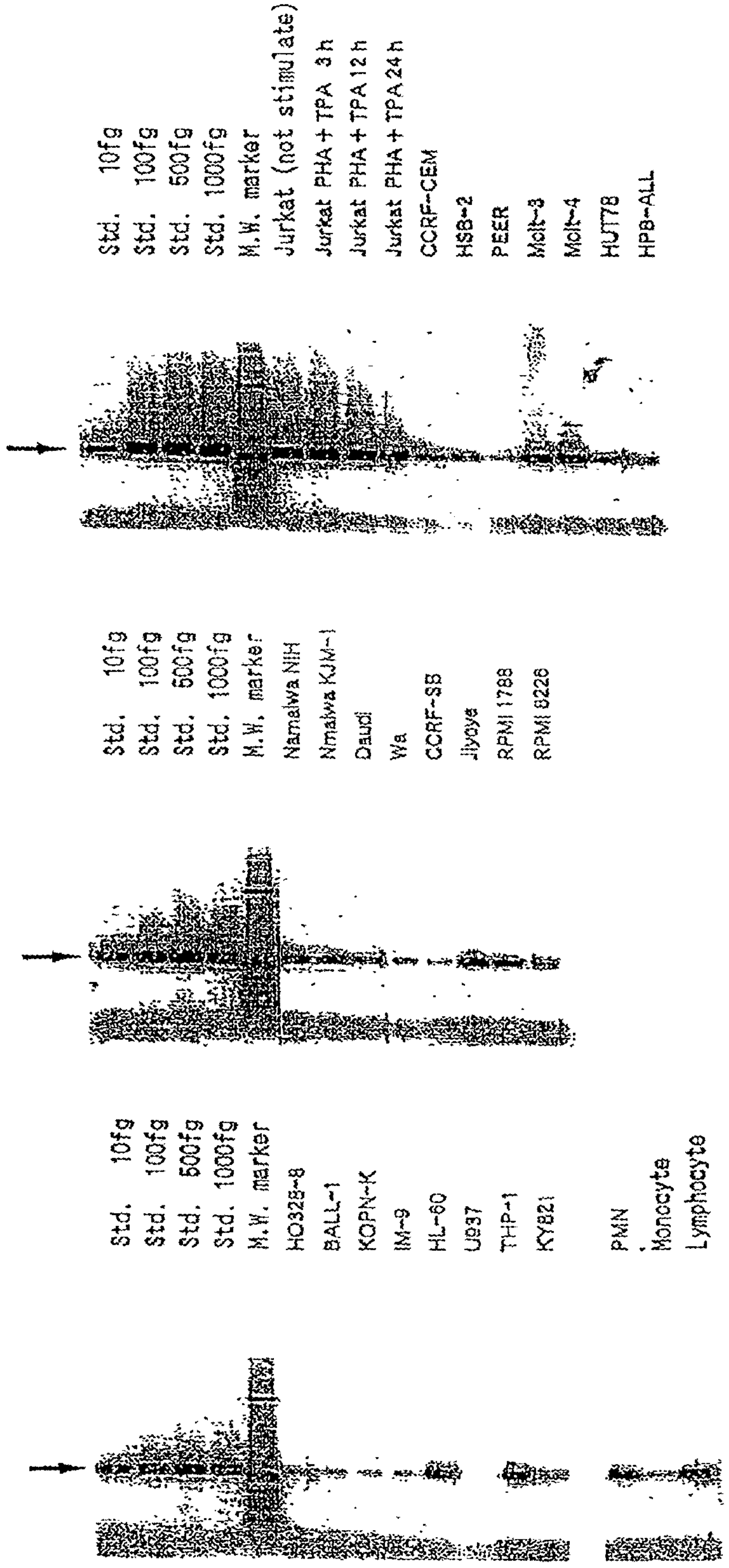
FIG. 15 is an electrophoresis pattern showing a result of the examination of the expression level of G3 transcript in various human leukocyte cell lines, human polynuclear leukocyte (PMN), human monocyte and human lymphocyte, using a PCR method. The number of cycles of the PCR is 28. The arrow shows the position of the amplified fragment of target (564 bp).

Although the expression level was low, G3 transcripts was expressed in all of the 35 human organs examined (FIG. 14). Its expression was also found in various human leukocyte cell lines and the polymorphonuclear leukocytes, monocytes and lymphocytes prepared from human peripheral blood (FIG. 15).

Figure 16:
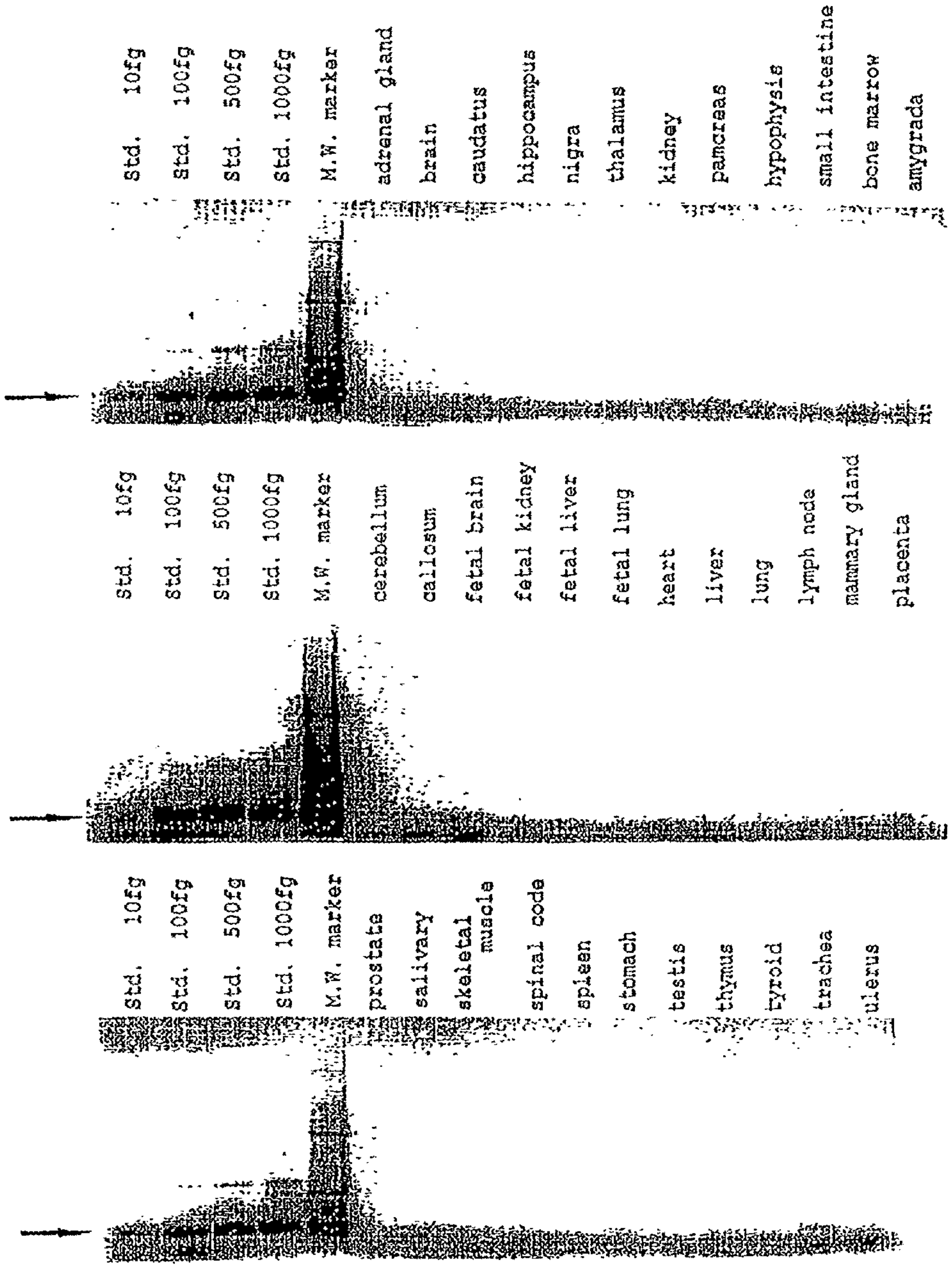
FIG. 16 is an electrophoresis pattern showing a result of the examination of the expression level of G4 transcript in 35 kinds of human organ, using a PCR method. The number of cycles of the PCR is 26. The arrow shows the position of the amplified fragment of target (202 bp).
Figure 17:
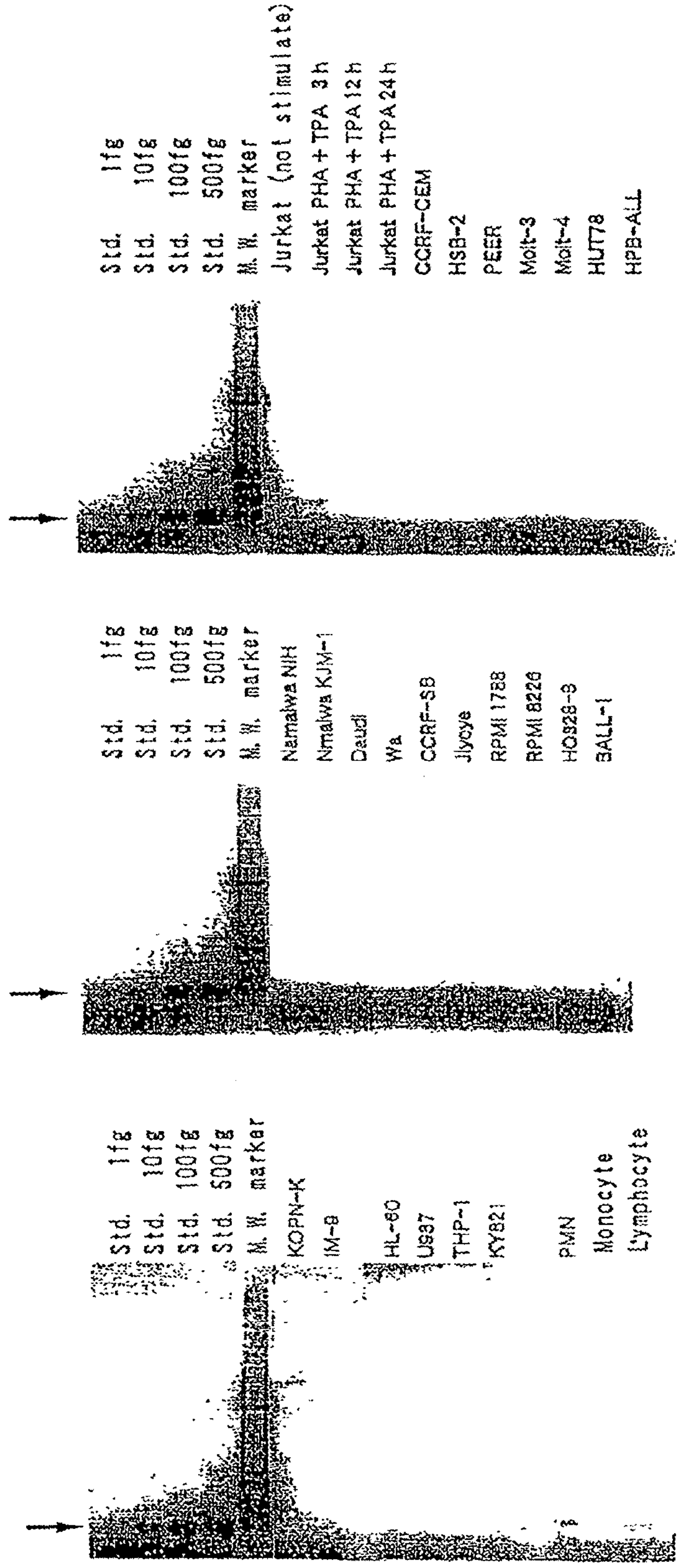
FIG. 17 is an electrophoresis pattern showing a result of the examination of the expression level of G4 transcript in various human leukocyte cell lines, human polynuclear leukocyte (PMN), human monocyte and human lymphocyte, by a PCR method. The number of cycles of the PCR is 28. The arrow shows the position of the amplified fragment of target (202 bp).

G4 transcript was expressed in a small amount in trachea, placenta and stomach among the 35 human organs shown in the above (1) (FIG. 16). Its expression was not found in various human leukocyte cell lines and polymorphonuclear leukocytes and lymphocytes prepared from human peripheral blood (FIG. 17).

Figure 18:
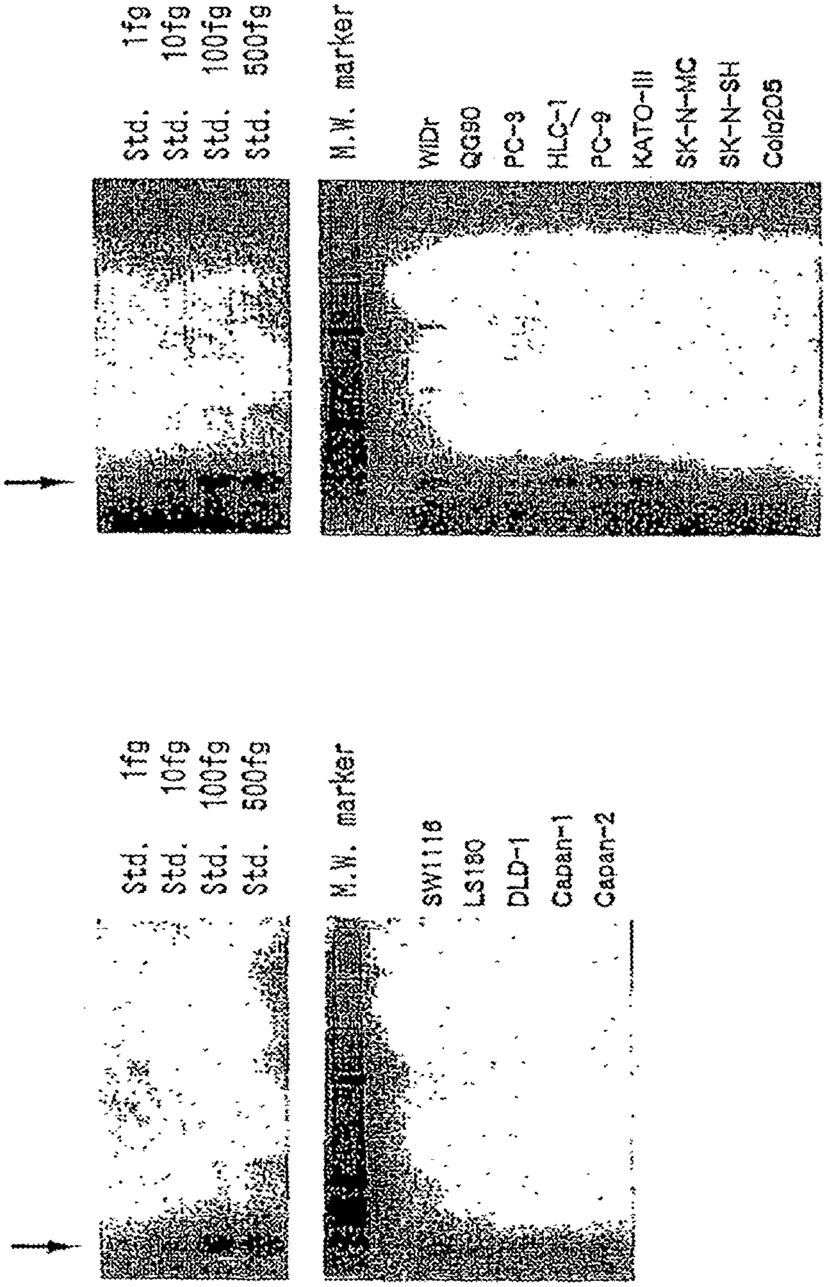
FIG. 18 is an electrophoresis pattern showing a result of the examination of the expression level of G4 transcript in various human cancer cell lines, by a PCR method. The number of cycles of the PCR is 27. The arrow shows the position of the amplified fragment of target (202 bp).

On the other hand, a relatively large amount of expression was found in colon cancer cell lines (WiDR, Colo205, SW1116, LS180, DLD-1), lung cancer cell lines (QG90, HLC-1, PC9), pancreatic cancer cell lines (Capan-1, Capan-2) and a gastric cancer cell line KATO III (FIG. 18). As an example, results of the determination are shown below. Values expressed as the ratio (%) of the expression level of G4 transcript in WiDR, QG90, PC-3, HLC-1, PC9, KATO III, SK-N-MC, SK-N-SH, Colo205, SW1116, LS180, DLD-1, Capan-1 and Capan-2 based on the expressed amount of β-actin transcript are 0.49, 0.29, 0.069, 0.34, 0.35, 0.94, 0.027, 0.0037, 0.10, 4.6, 0.95, 0.85, 0.67 and 0.92 in this order.

Figure 19:
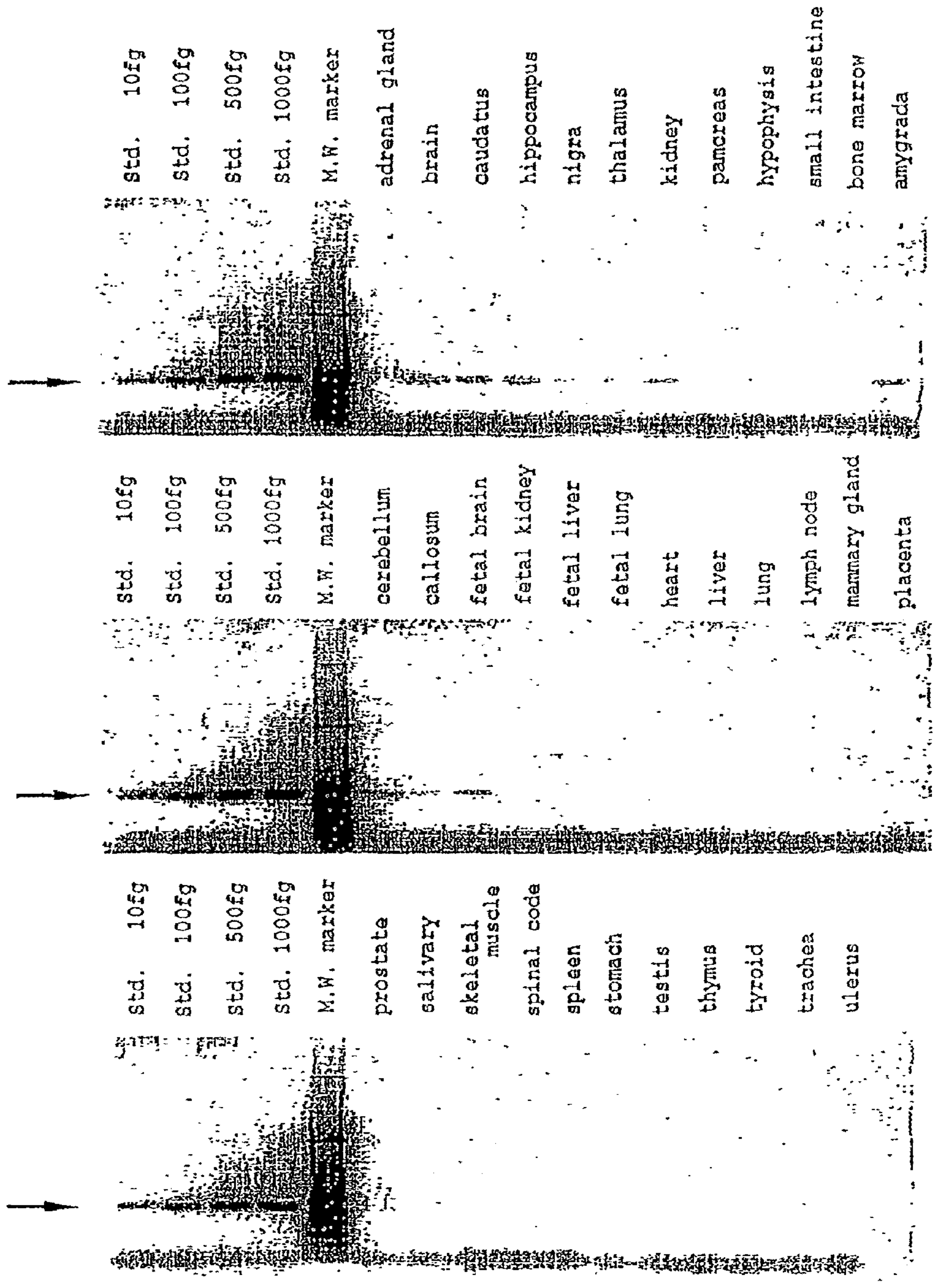
FIG. 19 is an electrophoresis pattern showing a result of the examination of the expression level of G7 transcript in 35 kinds of human organ, by a PCR method. The number of cycles of the PCR is 26. The arrow shows the position of the amplified fragment of target (456 bp).
Figure 20:
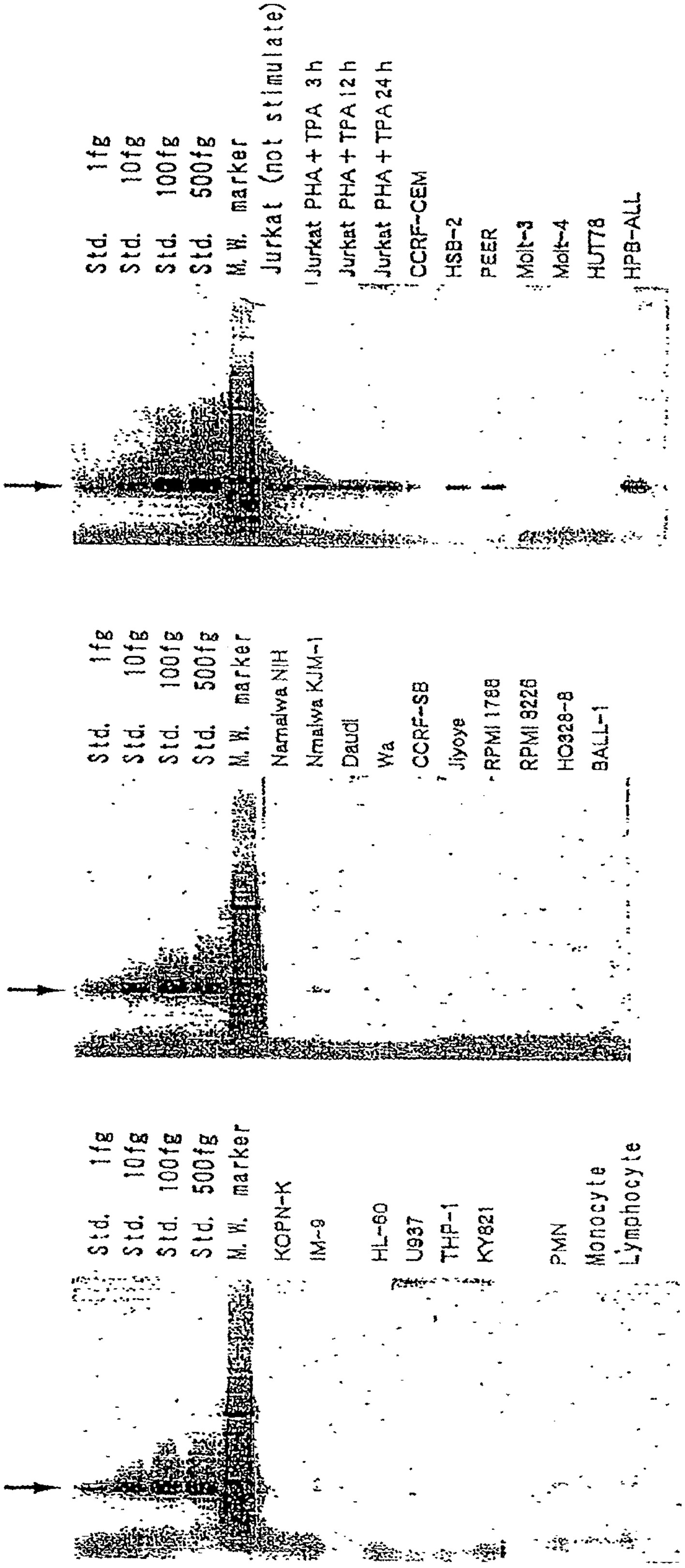
FIG. 20 is an electrophoresis pattern showing a result of the examination of the expression level of G7 transcript in various human leukocyte cell lines, human polynuclear leukocyte (PMN), human monocyte and human lymphocyte, by a PCR method. The number of cycles of the PCR is 28. The arrow shows the position of the amplified fragment of target (456 bp).

G7 transcript was expressed in a small amount in brain, caudate nucleus, hippocampus, kidney, amygdala, cerebellum and fetal brain among the 35 human organs shown in the above (1) (FIG. 19). Its expression was hardly found in polymorphonuclear leukocytes, monocytes and lymphocytes prepared from human peripheral blood (FIG. 20). Among the T-cell lines, a small amount of expression was found only in Jurkat and HPB-ALL, but the expression was not found in the B-cell lines (FIG. 20).

On the other hand, a relatively large amount of expression was found in a neuroblastoma cell line SK-N-MC and a prostate cancer cell line PC-3. A small amount of expression was found in colon cancer cell lines (Colo205, SW1116 and LS180) and pancreatic cancer cell lines (Capan-1 and Capan-2).

Based on the results, it was found that expression pattern of respective genes for G3, G4 and G7 is different from one another. Thus, it is considered that each of these three genes for G3, G4 and G7 encode a β1,3-N-acetylglucosaminyltransferase but each gene takes part in different functions in different tissues.

Since the expression level of the G3 transcript was large in leukocytes, it was suggested that G3 involved in the synthesis of a poly-N-acetyllactosamine sugar chain in leukocytes. Accordingly, there is a possibility that inflammation can be diagnosed by examining the expression level of G3 transcript or G3 polypeptide. Also, there is a possibility that inflammation can be controlled by controlling the expression of the G3 gene and inhibiting the activity of G3 polypeptide.

Also, since G3 transcript is expressed in mammary gland, there is a possibility that G3 involved in the synthesis of oligosaccharides having GlcNAcβ-1-3Gal structure contained in human milk such as LNnT, LNT and the like.

Regarding G4 transcript, since its expression level is increased in cell lines derived from colon cancer, pancreatic cancer and gastric cancer, there is a possibility that cancers can be diagnosed by examining the expression level of G4 transcript or G4 polypeptide. Also, there is a possibility that metastasis of cancer cells can be controlled by controlling the expression of G4 gene and inhibiting the activity of G4 polypeptide.

Regarding G7 transcript, since its expression level is increased in cell lines derived from neuroblastoma, prostatic cancer, colon cancer and pancreatic cancer, there is a possibility that diagnosis of cancers can be made by examining the expression level of G7 transcript or G7 polypeptide. Also, there is a possibility that metastasis of cancer cells can be controlled by controlling the expression of G7 gene and inhibiting the activity of G7 polypeptide.

Also, since the expression pattern of two β1,3-N-acetylglucosaminyltransferases so far cloned in various cells and tissues is different from that of three novel β1,3-N-acetylglucosaminyltransferases (G3, G4 and G7) obtained according to the present invention, it is considered that these three novel β1,3-N-acetylglucosaminyltransferases have functions different from those of the known enzymes.

Example 14

Production of a FLAG Peptide-Fused β1,3-N-Acetylglucosaminyltransferase (G3) as a Secreted Form Using Insect Cell as a Host Secreted expression of a FLAG peptide-fused G3 polypeptide in an insect cell was carried out in the same manner as in Example 10.

(1) Construction of a Plasmid pVL1393-F2G3

It was considered based on its primary sequence that G3 polypeptide comprises an N-terminal cytoplasmic region containing 9 amino acids, a subsequent membrane-binding region rich in hydrophobic nature containing 19 amino acids, a stem region containing at least 12 amino acids and the remaining C-terminal part comprising most of the polypeptide and containing a catalytic region. Accordingly, secreted expression of G3 polypeptide was attempted by removing the N-terminal cytoplasmic region containing 9 amino acids, the membrane-binding region containing 19 amino acids and a part of the stem region (2 amino acids), and adding a immunoglobulin signal sequence and FLAG peptide to the removed regions.

First, a plasmid pBlunt-G3 was constructed by preparing a DNA region encoding a region considered to have the catalytic activity of G3 polypeptide (from the 31st serine to the 397th cysteine in SEQ ID NO:1) by PCR and then inserting it into pCR-Blunt vector (manufactured by Invitrogen). The specific method is described below.

As primers for PCR, a DNA fragment shown by SEQ ID NO:31 (hereinafter referred to as "G3-1") and a DNA fragment shown by SEQ ID NO:32 (hereinafter referred to as "G3-2") were synthesized. They are designed such that a BamHI site is generated in G3-1, and a NotI site in G3-2.

PCR was carried out by using Pyrobest DNA Polymerase manufactured by TaKaRa and 10× Pyrobest Buffer and 2.5 mmol/l dNTP Mixture attached to the kit, in accordance with the instructions. Using a DNA thermal cycler (PERKIN ELMER CETUS DNA Thermal Cycler; manufactured by TaKaRa), 16 cycles of the reaction at 94° C. for 30 seconds, 65° C. for 1 minute and 72° C. for 2 minutes were carried out, followed by a reaction at 72° C. for 10 minutes. As a template, 20 ng of a plasmid pBS-G3 constructed in Example 2 was used. A DNA fragment of about 1.1 kb was obtained by the PCR. A plasmid pBlunt-G3 was constructed by inserting this DNA fragment into pCR-Blunt vector. The absence of errors by the PCR was confirmed by determining the nucleotide sequence of the DNA fragment inserted into pBlunt-G3.

By digesting pBlunt-G3 with restriction enzymes BamHI and NotI, a BamHI-NotI fragment of 1.1 kb encoding a region considered to have the catalytic activity of G3 polypeptide (from the 31st serine to the 397th cysteine in SEQ ID NO:1) was obtained. By digesting pVL1393 with restriction enzymes NotI and BstPI, a NotI-BstPI fragment of 6.4 kb was obtained. By digesting a plasmid pVL1393-F2G4 constructed in Example 10 with restriction enzymes BamHI and BstPI, a BamHI-BstPI fragment of 3.3 kb was obtained. pVL1393-F2G3 was constructed by linking these three fragments.

(2) Preparation of a Recombinant Virus

A recombinant virus was prepared for the secreted expression of the FLAG peptide-fused G3 polypeptide in an insect cell. A recombinant baculovirus was prepared by introducing a filamentous baculovirus DNA and the plasmid pVL1393-F2G3 constructed in the above (1) into an insect cell Sf9 by a lipofectin method. The method described in Example 10 was used.

(3) Secreted Production and Purification of a FLAG Peptide-Fused G3 Polypeptide

A FLAG peptide-fused G3 polypeptide was produced as a secreted form in the insect cell by using the recombinant virus prepared in the above (2). Thereafter, the polypeptide was purified from a culture supernatant containing the polypeptide. The method described in Example 10 was used.

Figure 21:
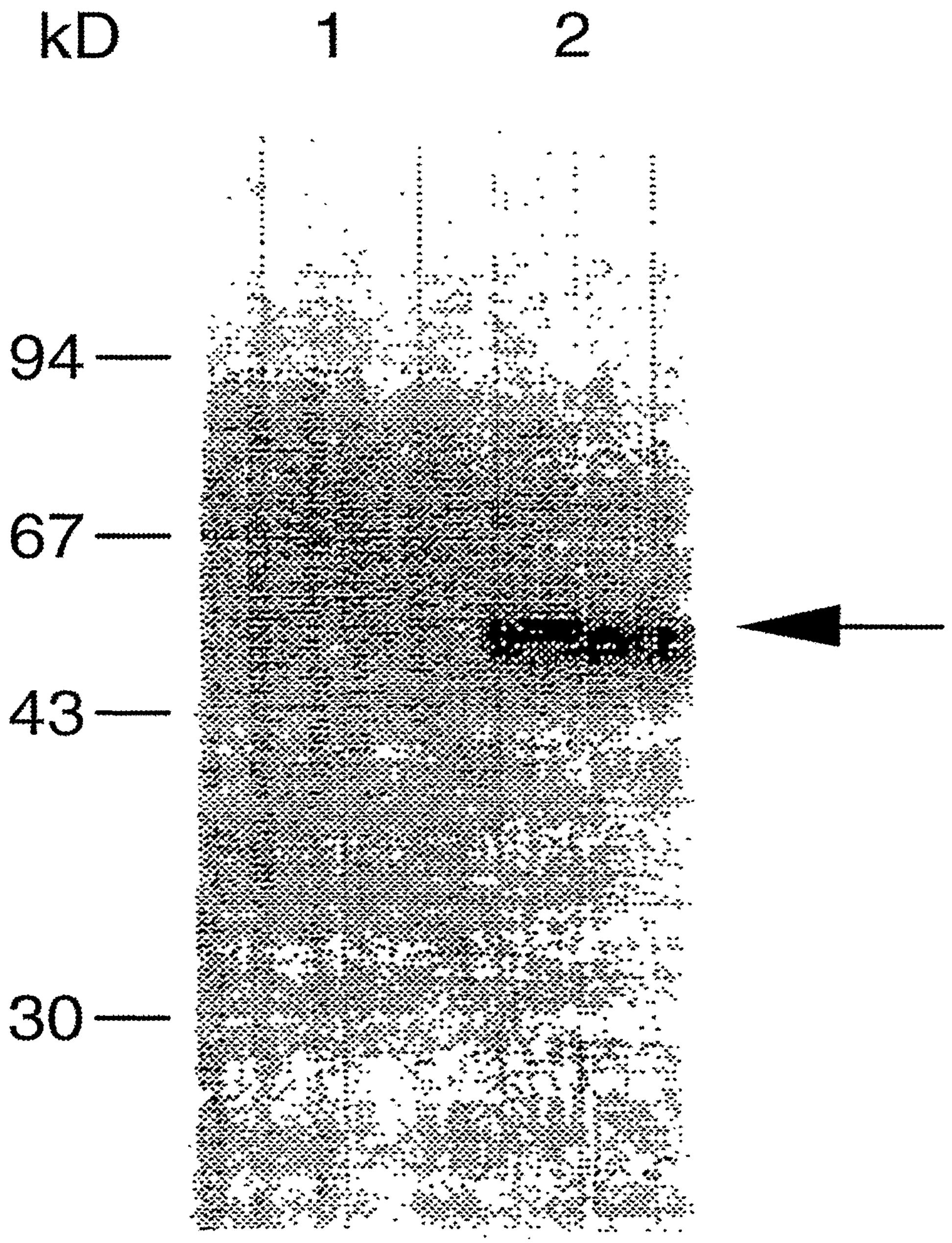
FIG. 21 is a graph showing a result obtained by purifying FLAG peptide-fused secreted G3 from a culture supernatant of Sf21 cell infected with a recombinant virus derived from a plasmid pVL1393-F2G3 by using Anti-FLAG M1 Affinity Gel, and then subjecting it to SDS polyacrylamide gel electrophoresis (lane 2). As a control, a sample was prepared from a culture supernatant of Sf21 cell infected with a recombinant virus derived from a plasmid pVL1393 in the same manner and then subjected to SDS polyacrylamide gel electrophoresis (lane 1). The arrow shows the position of the produced secreted G3 polypeptide.

SDS-PAGE was carried out by using 15 μl of a purified sample, and then staining was carried by using Coomassie Brilliant Blue (FIG. 21). When a purified sample prepared from the culture supernatant of Sf21 infected with the recombinant virus derived from pVL1393-F2G3 was used, bands ranging from 51 to 56 kD were found. It is considered that difference in the molecular weight of each band is based on the number and size of the added sugar chain. In G3 polypeptide, there are five N-glycosylation. On the other hand, such bands were not detected when a sample purified from the culture supernatant of Sf21 infected with the recombinant virus derived from the vector pVL1393 was used in the same manner.

Based on the above result, it was shown that the FLAG peptide-fused G3 polypeptide is produced as a secreted form in the insect cell culture supernatant and can be purified easily by use of Anti-FLAG M1 Affinity Gel.

(4) Measurement of a β1,3-N-Acetylglucosaminyltransferase Activity of a FLAG Peptide-Fused G3 Polypeptide A β1,3-N-acetylglucosaminyltransferase activity of FLAG peptide-fused G3 polypeptide was measured by using 15 μl of the purified sample prepared in the above (3). The method of Example 8 was used for the activity measurement. As a result, a β1,3-N-acetylglucosaminyltransferase activity was detected. The ratio of the substrate converted into the product was 100%. On the other hand, when the sample purified from the culture supernatant of Sf21 infected with a vector pVL1393 was used in the same manner, the activity was not detected.

Based on the above result, it was shown that the FLAG peptide-fused G3 polypeptide secreted expression in the insect cell has a β1,3-N-acetylglucosaminyltransferase activity. The result shows that a β1,3-N-acetylglucosaminyltransferase (G3) can be produced as a secreted form fused with FLAG peptide in insect, and that synthesis of sugar chains can be made by using the produced fusion protein.

Example 15

Examination on Substrate Specificity of a Secreted β1,3-N-Acetylglucosaminyltransferase (Secretory G3)

Substrate specificity of a β1,3-N-acetylglucosaminyltransferase (G3) was examined using the FLAG peptide-fused G3 polypeptide purified in Example 14.

(1) Analysis by Using Pyridylaminated Oligosaccharides as Substrates

Substrate specificity of the FLAG peptide-fused G3 polypeptide was examined by the method shown in Example 11(1). The reaction was carried out at 37° C. for 2 hours. Relative activities when the activity on LNnT used as a substrate is defined as 100% are shown in Table 3. When LNnT was used as a substrate, the conversion efficiency of the substrate into the product was 82.5%. It was found that a β1,3-N-acetylglucosaminyltransferase (G3) uses LNnT as a good substrate but hardly uses LNT as a substrate. On the other hand, it was found that an oligosaccharide LNFP-V in which fucose is added to glucose residue in LNT via an α1,3-linkage becomes a relatively good substrate of G3. It was found also that an oligosaccharide LNFP-III in which fucose is added via an α1,3-linkage to the GlcNAc residue existing in the second position from the non-reducing terminal of LNnT does not become a substrate of G3. Also, it was found that oligosaccharides LNFP-II and LNDFH-II in which fucose is added via an α1,4-linkage to GlcNAc residue existing in the second position from the non-reducing terminal of LNnT do not become substrates of G3.

By comparing Tables 1 and 3 with Table 5 which will be described later, it was also found that a β1,3-N-acetylglucosaminyltransferase (G3) is an enzyme having a substrate specificity which is clearly different from that of the other β1,3-N-acetylglucosaminyltransferases (G4 and G7) obtained according to the present invention.

TABLE 3

Substrate specificity of a β1,3-N-acetylglucosaminyltransferase (G3) with pyridylaminated oligosaccharides as substrates

| Substrate | Sugar chain structure | Relative activity (%) |
|---|---|---|
| LNnT | Galβ1-4GlcNAcβ1-3Galβ1-4Glc | 100 |
| LNFP-III | Galβ1-4(Fucα1-3)GlcNAcβ1-3Galβ1-4Glc | 0 |
| LNT | Galβ1-3GlcNAcβ1-3Galβ1-4Glc | 3.7 |
| LNFP-II | Galβ1-3(Fucα1-4)GlcNAcβ1-3Galβ1-4Glc | 0 |
| LNFP-V | Galβ1-3GlcNAcβ1-3Galβ1-4(Fucα1-3)Glc | 30.8 |
| LNDFH-II | Galβ1-3(Fucα1-4)GlcNAcβ1-3Galβ1-4(Fucα1-3)Glc | 0 |

(2) Analysis Using Unlabeled Oligosaccharides as Substrates

Substrate specificity of the FLAG peptide-fused G3 polypeptide was examined by the method shown in Example 11(2). The enzyme reaction was carried out at 37° C. for 2 hours.

Relative activities when the activity for LNnT used as a substrate is defined as 100% are shown in Table 4. When LNnT was used as a substrate, the conversion ratio of a substrate into the product was 4.6%. It was found that the β1,3-N-acetylglucosaminyltransferase (G3) uses a disaccharide lactose and a hexaose LNnH as good substrates in addition to a tetraose LNnT. Based on the above, it is considered that G3 can synthesize a poly-N-acetyllactosamine sugar chain efficiently. Although the activity was lower than the activity for LNnT, lactose and LNnH, LacNAc and LNT were also usable as substrates for G3. It is known that already known β1,3-N-acetylglucosaminyltransferases prefer LacNAc as a good substrate rather than lactose [*J. Biol. Chem.,* 268, 27118 (1993), *Proc. Natl. Acad. Sci. USA,* 96, 406 (1999)]. In consequence, it was found that the β1,3-N-acetylglucosaminyltransferase (G3) is an enzyme having a substrate specificity which is clearly different from that of the already known enzymes. As an example, the substrate specificity of a cloned β3GnT (reported values) is also shown in Table 4 *[Proc. Natl. Acad. Sci. USA,* 96, 406 (1999)].

By comparing Tables 2 and 4 with Table 6 which will be described later, it was confirmed also that, similar to the results of Example 14, the β1,3-N-acetylglucosaminyltransferase (G3) is an enzyme having a substrate specificity which is clearly different from that of the other β1,3-N-acetylglucosaminyltransferases (G4 and G7) obtained by the present invention.

TABLE 4

Substrate specificity of a β1,3-N-acetylglucosaminyltransferase (G3) with unlabeled oligosaccharides as substrates

| | | Relative activity (%) | |
|---|---|---|---|
| Substrate | Sugar chain structure | G3 | β3GnT |
| LNnT | Galβ1-4GlcNAcβ1-3Galβ1-4Glc | 100 | 100 |
| LNT | Galβ1-3GlcNAcβ1-3Galβ1-4Glc | 27 | 6 |
| LNnH | Galβ1-4GlcNAcβ1-3Galβ1-4GlcNAcβ1-3Galβ1-4Glc | 132 | |
| Lactose | Galβ1-4Glc | 128 | 67.1 |
| LacNAc | Galβ1-4GlcNAc | 21 | 95.5 |

On the other hand, when β1,3-galactosyltransferase activity of the secreted G3 was measured by using GlcNAc and GlcNAβ1-3Galβ1-4Glc as acceptor substrates, the activity was not detected. In consequence, it was found that G3 does not have a β1,3-galactosyltransferase activity. The method described in Example 11(2) was used.

Example 16

Synthesis of a Poly-N-Acetyllactosamine Sugar Chain Using Secreted β1,3-N-Acetylglucosaminyltransferase (Secreted G3)

A poly-N-acetyllactosamine sugar chain was synthesized by using the FLAG peptide-fused G3 polypeptide purified in Example 14 and β1,4-galactosyltransferase.

(1) One-Pot Reaction

LNnT was allowed to react simultaneously with the FLAG peptide-fused G3 polypeptide purified in Example 14 and β1,4-galactosyltransferase (manufactured by SIGMA) purified from bovine milk by the method shown in Example 12(2) to thereby synthesize a sugar chain in which N-acetylglucosamine was added to the non-reducing end of LNnT (Galβ1-4GlcNAcβ1-3Galβ1-4GlcNAcβ1-3Galβ1-4Glc) and a sugar chain in which a poly-N-acetyllactosamine sugar chain [Galβ1-4GlcNAβ1-3]$_n$ (n represents two or more)] was added to the non-reducing end of LNnT.

The specific reaction was carried out as follows.

The reaction was carried out at 37° C. for 5 hours in 30 μl of a reaction solution [200 mmol/l MOPS (pH 7.5), 20 mmol/l UDP-GlcNAc (SIGMA), 50 mmol/l UDP-Gal (SIGMA), 20 mmol/l $MnCl_2$, 50 μmol/l of a pyridylaminated sugar chain substrate, 10 μl of the G3 polypeptide purified in Example 14, and 20 mU of β1,4-galactosyltransferase]. As the substrate, pyridylaminated LNnT was used, and formation of products were confirmed by HPLC. The method described in Example 11(1) was used.

As a result, a sugar chain in which [Galβ1-4GlcNAcβ1-3]$_n$ (n=1, 2, 3 or 4)] was added to the non-reducing end of pyridylaminated LNnT was synthesized. In consequence, it was found that poly-N-acetyllactosamine sugar chains can be efficiently synthesized by a one-pot reaction by using the G3 polypeptide and a β1,4-galactosyltransferase. It is considered that synthesis of longer poly-N-acetyllactosamine sugar chains is possible by increasing the amount of the enzymes, the amount of the substrate and the reaction time.

Example 17

Production of FLAG Peptide-Fused β1,3-N-Acetylglucosaminyltransferase (G7) as a Secreted Form by Using Insect Cell as a Host Secreted expression of the FLAG peptide-fused G7 polypeptide in an insect cell was carried out in the same manner as in Example 10.

(1) Construction of a Plasmid pVL1393-F2G7

It was considered based on its primary sequence that the G7 polypeptide comprises an N-terminal cytoplasmic region containing 29 amino acids, a subsequent membrane-binding region rich in hydrophobic nature containing 20 amino acids, a stem region containing at least 12 amino acids and the remaining C-terminal part comprising most of the polypeptide and containing a catalytic region. Accordingly, an attempt was made to effect secreted expression of G7 polypeptide by removing the N-terminal cytoplasmic region containing 29 amino acids, the membrane-binding region containing 20 amino acids and a part of the stem region (6 amino acids) and adding a immunoglobulin signal sequence and FLAG peptide to the removed regions.

First, a plasmid pBlunt-G7 was constructed by preparing a DNA region encoding a region considered to have the catalytic activity of G7 polypeptide (from the 56th alanine to the 378th arginine in SEQ ID NO:4) by PCR and then inserting it into a vector pCR-Blunt vector. The specific method is described below.

A DNA shown by SEQ ID NO:33 (hereinafter referred to as "G7S-1") and a DNA shown by SEQ ID NO:34 (hereinafter referred to as "G7S-2") were synthesized as primers for PCR.

They are designed such that a BglII site is generated in G7S-1, and a NotI site in G7S-2.

PCR was carried out by using Pyrobest DNA Polymerase manufactured by TaKaRa and 10× Pyrobest Buffer and 2.5 mmol/l dNTP Mixture attached to the kit, in accordance with the instructions. Using a DNA thermal cycler (PERKIN ELMER CETUS DNA Thermal Cycler; manufactured by TaKaRa), 16 cycles of a reaction, one cycle consisting of reaction at 94° C. for 30 seconds, 65° C. for 1 minute and 72° C. for 2 minutes, were carried out, followed by reacting at 72° C. for 10 minutes. As the template, 20 ng of a plasmid pT7B-G7 constructed in Example 4 was used. A DNA fragment of about 1.0 kb was obtained by the PCR. A plasmid pBlunt-G7 was constructed by inserting the DNA fragment into a vector pCR-Blunt. The absence of errors by the PCR was confirmed by determining nucleotide sequence of the DNA fragment inserted into pBlunt-G7.

By digesting pBlunt-G7 with restriction enzymes BglII and NotI, a BglII-NotI fragment of 1.0 kb encoding a region considered to have the catalytic activity of G7 polypeptide (from the 56th alanine to the 378th arginine in SEQ ID NO:4) was obtained. By digesting pVL1393 with restriction enzymes NotI and BstPI, a NotI-BstPI fragment of 6.4 kb was obtained. By digesting a plasmid pVL1393-F2G4 constructed in Example 10 with restriction enzymes BamHI and BstPI, a BamHI-BstPI fragment of 3.3 kb was obtained. pVL1393-F2G7 was constructed by linking these three fragments.

(2) Production of a Recombinant Virus

A recombinant virus was prepared for expression of the FLAG peptide-fused G7 polypeptide as a secreted form in an insect cell. A recombinant baculovirus was prepared by introducing a filamentous baculovirus DNA and a plasmid pVL1393-F2G7 constructed in the above (1) into an insect cell Sf9 by a lipofectin method. The method described in Example 10 was used.

(3) Secreted Production and Purification of FLAG Peptide-Fused G7 Polypeptide

Using the recombinant virus prepared in the above (2), a FLAG peptide-fused G7 polypeptide was produced as a secreted form in an insect cell. Thereafter, the polypeptide was purified from a culture supernatant containing the polypeptide. The method described in Example 10 was used.

Figure 22:
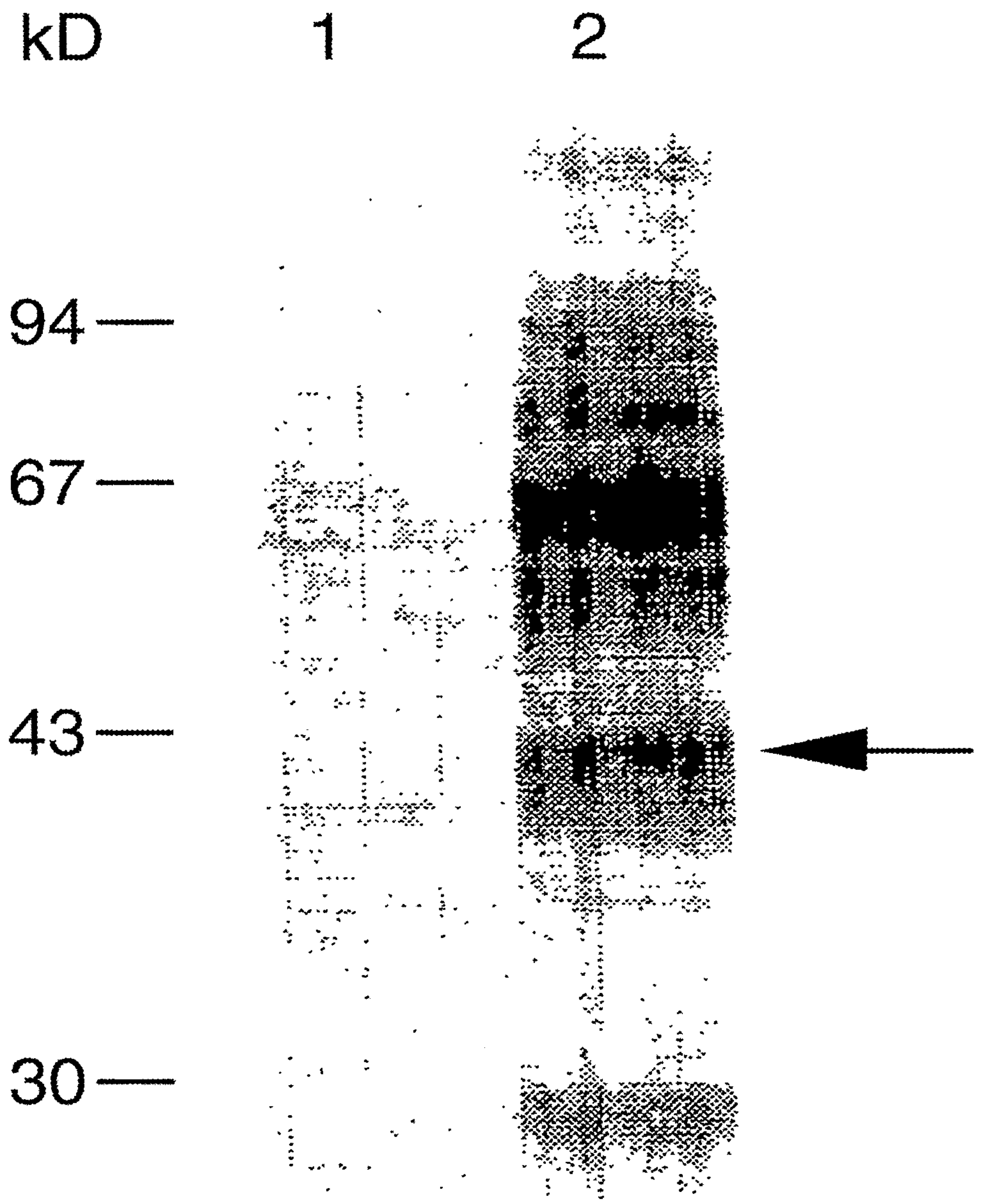
FIG. 22 is a graph showing a result obtained by purifying FLAG peptide-fused secretory G7 from a culture supernatant of Sf21 cell infected with a recombinant virus derived from a plasmid pVL1393-F2G7 by using Anti-FLAG M1 Affinity Gel, and then subjecting it to SDS polyacrylamide gel electrophoresis (lane 2). As a control, a sample was prepared from a culture supernatant of Sf21 cell infected with a recombinant virus derived from a plasmid pVL1393 in the same manner and then subjected to SDS polyacrylamide gel electrophoresis (lane 1). The arrow shows the position considered to be the produced secreted G7 polypeptide.

SDS-PAGE was carried out by using 15 μl of a purified sample, and then staining was carried out by using Coomassie Brilliant Blue (FIG. 22). When a purified sample prepared from the culture supernatant of Sf21 infected with the recombinant virus derived from pVL1393-F2G7 was used, a bands considered to be G7 polypeptide was found at a position of ranging from 40 to 42 kD. It is considered that difference in the molecular weight of each band is based on the number and size of the added sugar chain. In the G7 polypeptide, there are three N-glycosylation sites.

Based on the above result, it was shown that the FLAG peptide-fused G7 polypeptide is produced as a secreted form in the insect cell culture supernatant and can be purified easily by using Anti-FLAG M1 Affinity Gel.

(4) Measurement of a β1,3-N-Acetylglucosaminyltransferase Activity of the FLAG Peptide-Fused G7 Polypeptide A β1,3-N-acetylglucosaminyltransferase activity of FLAG peptide-fused G7 polypeptide was measured using 15 μl of the purified sample prepared in the above (3). The method of Example 8 was used for the activity measurement. As a result, a β1,3-N-acetylglucosaminyltransferase activity was detected. The ratio of the substrate converted into the product was 2.1%. On the other hand, when the sample purified from the culture supernatant of Sf21 infected with a vector pVL1393 was used in the same manner, the activity was not detected.

Based on the above result, it was shown that the FLAG peptide-fused G7 polypeptide expressed as a secreted form in the insect cell has a β1,3-N-acetylglucosaminyltransferase activity. The result showed that a β1,3-N-acetylglucosaminyltransferase (G7) can be produced as a secreted form fused with the FLAG peptide in insect cells, and that sugar chains can be synthesized by using the produced fusion protein.

Example 18

Examination of Substrate Specificity of the Secreted β1,3-N-Acetylglucosaminyltransferase (Secreted G7)

Examination of the substrate specificity of a β1,3-N-acetylglucosaminyltransferase (G7) was carried out using the FLAG peptide-fused G7 polypeptide purified in Example 17.

(1) Analysis Using Pyridylaminated Oligosaccharides as Substrates

Substrate specificity of the FLAG peptide-fused G7 polypeptide was examined by the method shown in Example 11(1). The reaction was carried out at 37° C. for 16 hours.

Relative activities when the activity for pyridylaminated LNnT used as a substrate is defined as 100% are shown in Table 5. When LNnT was used as the substrate, the conversion efficiency of the substrate into the product was 3.76%. It was found that the β1,3-N-acetylglucosaminyltransferase (G7) uses LNnT having a type II sugar chain (Galβ1-4GlcNAc) on the non-reducing end as a good substrate but hardly uses LNT or LNFP-V having a type II sugar chain (Galβ1-3GlcNAc) on the non-reducing end as a substrate. It was found also that an oligosaccharide LNFP-III in which fucose is added via an α1,3-linkage to the GlcNAc residue present in the second position from the non-reducing end of LNnT hardly becomes a substrate for G7. It was found also that oligosaccharides LNFP-II and LNDFH-II in which fucose is added via an α1,4-linkage to the GlcNAc residue present in the second position from the non-reducing end of LNnT do not become substrates of G7.

By comparing Table 1, Table 3 with Table 5, it was also found that the β1,3-N-acetylglucosaminyltransferase (G7) is an enzyme having a substrate specificity which is clearly different from that of the other β1,3-N-acetylglucosaminyltransferases (G3 and G4) obtained by the present invention.

TABLE 5

Substrate specificity of a β1,3-N-acetylglucosaminyltransferase (G7) with pyridylaminated oligosaccharides as substrates

| Substrate | Sugar chain structure | Relative activity (%) |
|---|---|---|
| LNnT | Galβ1-4GlcNAcβ1-3Galβ1-4Glc | 100 |
| LNFP-III | Galβ1-4(Fucα1-3)GlcNAcβ1-3Galβ1-4Glc | 7.4 |
| LNT | Galβ1-3GlcNAcβ1-3Galβ1-4Glc | 7.6 |

TABLE 5-continued

| Substrate specificity of a β1,3-N-acetylglucosaminyltransferase (G7) with pyridylaminated oligosaccharides as substrates | | |
|---|---|---|
| Substrate | Sugar chain structure | Relative activity (%) |
| LNFP-II | Galβ1-3(Fucα1-4)GlcNAcβ1-3Galβ1-4Glc | 0 |
| LNFP-V | Galβ1-3GlcNAcβ1-3Galβ1-4(Fuc α1-3)Glc | 8.1 |
| LNDFH-II | Galβ1-3(Fucα1-4)GlcNAcβ1-3Galβ1-4(Fuc α1-3)Glc | 0 |

(2) Analysis by Using Unlabeled Oligosaccharides as Substrates

Substrate specificity of the FLAG peptide-fused G7 polypeptide was examined using the method shown in Example 11(2). The enzyme reaction was carried out at 37° C. for 15.5 hours.

Relative activities when the activity for LNnT used as a substrate is defined as 100% are shown in Table 6.

Conversion efficiency of the substrate into the product was 3.07% when LNnT was used as a substrate. The β1,3-N-acetylglucosaminyltransferase (G7) used a tetraose LNnT as the best substrate. G7 used a disaccharide lactose as a relatively good substrate but hardly used a hexaose LNnH as a substrate. G7 also used a disaccharide LacNAc but the activity was lower than that for lactose. On the other hand, G7 did not use LNT as a substrate.

Based on the above, it was considered that G7 can synthesize poly-N-acetyllactosamine sugar chains of up to hexaose, but its activity of synthesizing poly-N-acetyllactosamine sugar chains of octaose or more is considerably weak. It is known that already known β1,3-N-acetylglucosaminyltransferases use LacNAc as a good substrate rather than lactose [*J. Biol. Chem.,* 268, 27118 (1993), *Proc. Natl. Acad. Sci. USA,* 96, 406 (1999)]. In consequence, it was found that the β1,3-N-acetylglucosaminyltransferase (G7) is an enzyme having a substrate specificity which is clearly different from that of the already known enzymes. As an example, substrate specificity of a cloned β3GnT (reported values) is also shown in Table 6 [*Proc. Natl. Acad. Sci. USA,* 96, 406 (1999)].

By comparing Table 2, Table 4 with Table 6, it was confirmed also that the β1,3-N-acetylglucosaminyltransferase (G7) is an enzyme having a substrate specificity which is clearly different from that of the other β1,3-N-acetylglucosaminyltransferases (G3 and G4) obtained according to the present invention.

TABLE 6

| Substrate specificity of a β1,3-N-acetylglucosaminyltransferase (G7) with unlabeled oligosaccharides as substrates | | | |
|---|---|---|---|
| | | Relative activity (%) | |
| Substrate | Sugar chain structure | G7 | β3GnT |
| LNnT | Galβ1-4GlcNAcβ1-3Galβ1-4Glc | 100 | 100 |
| LNT | Galβ1-3GlcNAcβ1-3Galβ1-4Glc | 0 | 6 |
| LNnH | Galβ1-4GlcNAcβ1-3Galβ1-4GlcNAcβ1-3Galβ1-4Glc | 0.05 | |
| Lactose | Galβ1-4Glc | 32.6 | 67.1 |
| LacNAc | Galβ1-4GlcNAc | 8.5 | 95.5 |

On the other hand, when β1,3-galactosyltransferase activity of the secreted G7 was measured by using GlcNAc and GlcNAcβ1-3Galβ1-4Glc as acceptor substrates, the activity was not detected. In consequence, it was found that G7 does not have a β1,3-galactosyltransferase activity. The method described in Example 11(2) was used.

Example 19

Examination of a Expression Level of Transcript of Each Gene for G3, G4 and G7 in Various Cancer Tissues The expression level of transcript of each gene for G3, G4 and G7 in various cancer tissues and normal tissues around the cancer tissues was examined. The examination was carried out in accordance with literatures [*International Journal of Cancer,* 83, 70 (1999), *Glycobiology,* 9, 607 (1999), *Laboratory Investigation,* 78, 797 (1998)].

(1) Synthesis of Single-Stranded cDNAs Derived from Various Normal Tissues and Cancer Tissues Cancer tissues and normal tissues around the cancer tissues were collected from patients of colon cancer (10 cases), gastric cancer (7 cases) and lung cancer (6 cases). Total RNA was prepared from each of these tissues by the acid guanidium thiocyanate-phenol-chloroform method, and the synthesis of single-stranded cDNAs was carried out by using the total RNAs as the template. Single-stranded cDNAs were synthesized from 5 μg of the total RNA by using a kit (SUPERSCRIPT Preamplification System; manufactured by GIBCO), diluted 50 times with water and used as the PCR templates. An Oligo(dT) primer was used as a primer.

(2) Preparation of Standards and Internal Controls

The standards and internal controls were constructed by using pBS-G3, pBS-G4-2 and pT7B-G7 [cf. the following (a) to (f)].

In the determination of the amount of β-actin transcript, pUC119-ACT and pUC119-ACTd were converted into linear DNA fragments by digesting them with restriction enzymes (HindIII and Asp718) capable of cutting out the cDNA moieties and used as a standard and an internal control, respectively [*J. Biol. Chem.,* 269, 14730 (1994), Japanese Published Unexamined Patent Application No. 181759/94]. After confirming that each plasmid was completely cut out, they were used by diluting stepwise with water containing 1 μg/ml of yeast transfer RNA.

(a) Preparation of a Standard for Determination of the Amount of G3 Transcript

A BglII fragment of 4.5 kb was obtained by digesting pBS-G3 with a restriction enzyme BglII. pBS-G3S was constructed by linking this fragment. The G3 cDNA moiety was converted into linear DNA by digesting pBS-G3S with restriction enzymes XbaI and AccI, and used as a standard for the determination. After confirming that the plasmid was completely cut out, it was used by diluting stepwise with water containing 1 μg/ml of yeast transfer RNA.

(b) Preparation of an Internal Control for Determination of G3 the Amount of Transcript pBS-G3Sd was prepared by deleting 229 bp between Eco81I-PflMI in the G3 cDNA from pBS-G3S constructed in the above (a). An Eco81I-PflMI fragment of 4.3 kb was obtained by digesting pBS-G3S with restriction enzymes Eco81I and PflMI. pBS-G3Sd was constructed by linking this fragment. The G3 cDNA moiety was converted into linear DNA by digesting pBS-G3Sd with restriction enzymes XbaI and AccI, and used as an internal control in the determination. After confirming that the plasmid was completely cut out, it was used by diluting stepwise with water containing 1 μg/ml of yeast transfer RNA.

(c) Preparation of a Standard for Determination of the Amount of G4 Transcript

G4 cDNA moiety was converted into linear DNA by digesting pBS-G4-2 obtained in Example 3 with restriction enzymes XbaI and ClaI, and used as a standard for the determination. After confirming that the plasmid was completely cut out, it was used by diluting stepwise with water containing 1 μg/ml yeast transfer RNA.

(d) Preparation of an Internal Control for Determination of the Amount of G4 Transcript pBS-G4-2d was prepared by deleting 180 bp between BstEII-PmlI in the G4 cDNA from the pBS-G4-2 obtained in Example 3. A BstEII-PmlI fragment of 4.9 kb was obtained by digesting pBS-G4-2 with restriction enzymes BstEII and PmlI. pBS-G4-2d was constructed by linking this fragment. The G4 cDNA moiety was converted into linear DNA by digesting the pBS-G4-2d with XbaI and ClaI, and used as an internal control for the determination. After confirming that the plasmid was completely cut out, it was used by diluting stepwise with water containing 1 μg/ml of yeast transfer RNA.

(e) Preparation of a Standard for Determination of the Amount of G7 Transcription Product G4 cDNA moiety was converted into linear DNA by digesting the pT7B-G7 obtained in Example 4 with restriction enzymes Tth111I and NarI, and used as the standard for the determination. After confirming that the plasmid was completely cut out, it was used by diluting stepwise with water containing 1 μg/ml yeast transfer RNA.

(f) Preparation of an Internal Control for Determination of the Amount of G7 Transcript pT7B-G7d was prepared by deleting 208 bp between Tth111I-NarI in the G7 cDNA from the pT7B-G7 obtained in Example 4. A Tth111I-NarI fragment of 4.0 kb was obtained by digesting pT7B-G7 with restriction enzymes Tth111I and NarI. pT7B-G7d was constructed by linking the fragment. The G7 cDNA moiety was converted into linear DNA by digesting the pT7B-G7d with HincII and SmaI, and used as the internal control for the determination. After confirming that the plasmid was completely cut out, it was used by diluting stepwise with water containing 1 μg/ml yeast transfer RNA.

(3) Determination of the Amount of Transcript of Each Gene for G3, G4 and G7 by the Quantitative PCR Method PCR was carried out by using each single-stranded cDNAs prepared in the above (1) from normal tissues and cancer tissues as templates. As PCR primers, CB489 (SEQ ID NO:35) and CB490 (SEQ ID NO:36) were used for detecting G3 transcript, and CB495 (SEQ ID NO:37) and CB523 (SEQ ID NO:38) for detecting G4 transcript, and CB493 (SEQ ID NO:39) and CB525 (SEQ ID NO:40) for detecting G7 transcript. Also, calibration curves were prepared by carrying out PCR in the same manner by using the standards and internal controls prepared in the above (2) as respective templates.

By using DNA polymerase AmpliTaqGold™ (manufactured by PERKIN ELMER), PCR was carried out in a reaction solution [10 mmol/l Tris-HCl (pH 8.3), 50 mmol/l KCl, 1.5 mmol/l $MgCl_2$, 0.2 mmol/l dNTP, 0.001% (w/v) gelatin and 0.2 μmol/l each of gene-specific primers] containing 10 μl of cDNA derived from each of the above tissues and 10 μl (10 fg) of a plasmid as an internal control.

PCR was carried out under the following conditions.

In the determination of the amount of G3 transcript, the reaction solution was heated at 95° C. for 11 minutes and then 42 cycles of a reaction was carried out, one cycle consisting of reaction at 95° C. for 1 minute, 55° C. for 1 minute and 72° C. for 2 minutes.

In the determination of the amount of G4 transcript, the reaction solution was heated at 95° C. for 11 minutes and then 42 cycles of a reaction was carried out, one cycle consisting of reaction at 95° C. for 1 minute, 65° C. for 1 minute and 72° C. for 2 minutes.

In the determination of the amount of G7 transcript, the reaction solution was heated at 95° C. for 11 minutes and then 44 cycles of a reaction was carried out, one cycle consisting of reaction at 95° C. for 1 minute, 65° C. for 1 minute and 72° C. for 2 minutes as one cycle.

In the determination of the amount of β-actin transcript, the reaction solution was heated at 95° C. for 11 minutes and then 24 cycles of the reaction was carried out, one cycle consisting of reaction at 95° C. for 1 minute, 65° C. for 1 minute and 72° C. for 2 minutes as one cycle.

A 10 μl portion of each solution after PCR was subjected to 1% agarose gel electrophoresis, and the gel was stained with ethidium bromide and photographed. By scanning the photograph by use of an NIH image system, stained intensity of amplified fragments were measured and used as the amount. In order to determine the amount of transcripts more accurately, similar PCR was carried out by changing the number of cycles of PCR. Amounts of the standards and internal controls were changed depending on the number of cycles of the PCR.

By carrying out PCR using 1.25 fg, 2.5 fg, 5 fg, 10 fg, 20 fg and 40 fg of the standards prepared in the above (a), (c) and (e) instead of the cell-derived single-stranded cDNAs, amounts of amplified fragments were measured to prepare calibration curves by plotting the amount of cDNA and the amount of the amplified fragment.

When the primers for determination of the amount of G3 transcript are used, a DNA fragment of 647 bp is amplified from the G3 transcript and G3 standard, and a DNA fragment of 418 bp from the G3 internal control.

When the primers for determination of the amount of G4 transcription product are used, a DNA fragment of 498 bp is amplified from the G4 transcription product and G4 standard, and a DNA fragment of 318 bp from the G4 internal control.

When the primers for determination of the amount of G7 transcription product are used, a DNA fragment of 619 bp is amplified from the G7 transcription product and G7 standard, and a DNA fragment of 411 bp from the G7 internal control.

From the above calibration curve and the amount of amplified DNA fragments derived from each tissue, the amount of cDNA in each tissue was calculated and used as the amount of the transcription product. Also, since β-actin is considered to be a gene universally expressed in each tissue, it is considered that the expression level is almost the same in every tissue. Accordingly, a difference in the expression level of β-actin transcript in each tissue was considered to be the difference in the efficiency of cDNA synthesizing reaction, so that the expression level of β-actin transcription product was also taken into consideration when the expression level of the respective genes were compared.

Amounts of the G3, G4 and G7 transcription products in cancer tissues and peripheral normal tissues of colon cancer patients (10 cases) are shown in Table 7 as relative values when the amount of β-actin transcript is defined as 1,000.

Expression of G3 and G4 transcripts was found in cancer tissues and peripheral normal tissues of colon patients in most cases, but no correlation was found between the expression level in cancer tissues and normal tissues. On the other hand, G7 transcript was hardly expressed in any of the cancer tissues and normal tissues. It can be considered that the expression hardly occurred when the expression (relative value) was 1 or less.

TABLE 7

| Sample name | Patient No. | Tissue | Amount of transcription product G3 | G4 | G7 |
|---|---|---|---|---|---|
| 10N | 10 | normal | 35 | 27 | 0.51 |
| 10T | 10 | cancer | 5.6 | 5.1 | 0.20 |
| 11N | 11 | normal | 2.3 | 5.1 | 0.17 |
| 11T | 11 | cancer | 4.4 | 7.4 | 0.12 |
| 13N | 13 | normal | 7.8 | 5.3 | 0.055 |
| 13T | 13 | cancer | 6.0 | 0.070 | 0.01> |
| 15N | 15 | normal | 0.01> | 0.01> | 0.01> |
| 15T | 15 | cancer | 5.4 | 5.0 | 0.01> |
| 17N | 17 | normal | 3.9 | 5.1 | 0.085 |
| 17T | 17 | cancer | 4.4 | 24 | 1.5 |
| 18N | 18 | normal | 6.9 | 35 | 0.086 |
| 18T | 18 | cancer | 3.3 | 5.6 | 0.01> |
| 19N | 19 | normal | 7.4 | 6.3 | 0.01> |
| 19T | 19 | cancer | 3.8 | 6.4 | 0.16 |
| 22N | 22 | normal | 3.6 | 4.0 | 0.01> |
| 22T | 22 | cancer | 8.6 | 5.0 | 0.01> |
| 23N | 23 | normal | 3.5 | 4.9 | 0.01> |
| 23T | 23 | cancer | 4.6 | 5.2 | 0.057 |
| 24N | 24 | normal | 4.9 | 7.3 | 0.14 |
| 24T | 24 | cancer | 3.4 | 6.2 | 0.090 |

Amounts of the G3, G4 and G7 transcripts in cancer tissues and peripheral normal tissues of gastric cancer patients (7 cases) are shown in Table 8 as relative values when the amount of β-actin transcript is defined as 1,000.

Expression of G3 and G4 transcripts was found in cancer tissues and peripheral normal tissues of gastric cancer patients in most cases, but no correlation was found between the expression level in cancer tissues and normal tissues. On the other hand, G7 transcript was hardly expressed in any of the cancer tissues and normal tissues.

TABLE 8

| Sample name | Patient No. | Tissue | Amount of transcription product G3 | G4 | G7 |
|---|---|---|---|---|---|
| MK2N | MK2 | normal | 56 | 120 | 0.01> |
| MK2T | MK2 | cancer | 8.5 | 12 | 0.26 |
| MK4N | MK4 | normal | 3.2 | 14 | 0.067 |
| MK4T | MK4 | cancer | 4.3 | 4.8 | 0.038 |
| MK5N | MK5 | normal | 0.01> | 4.5 | 0.059 |
| MK5T | MK5 | cancer | 4.6 | 6.0 | 0.26 |
| MK6N | MK6 | normal | 6.0 | 8.0 | 0.01> |
| MK6T | MK6 | cancer | 8.6 | 8.6 | 0.077 |
| MK7N | MK7 | normal | 12 | 12 | 0.01> |
| MK7T | MK7 | cancer | 18 | 17 | 0.15 |
| MK10N | MK10 | normal | 7.3 | 5.5 | 0.01> |
| MK10T | MK10 | cancer | 5.8 | 4.0 | 0.18 |
| MK12N | MK12 | normal | 4.8 | 12 | 0.01> |
| MK12T | MK12 | cancer | 17 | 13 | 0.01> |

Amounts of the G3, G4 and G7 transcripts in cancer tissues and peripheral normal tissues of lung cancer patients (6 cases) are shown in Table 9 as relative values when the amount of β-actin transcript is defined as 1,000.

Expression of G3 transcript was found in cancer tissues and peripheral normal tissues of lung cancer patients in all cases, but no correlation was found between the expression level in cancer tissues and normal tissues. G7 transcript was hardly expressed in any of the cancer tissues and normal tissues.

Regarding G4 transcript, the expression was hardly found in normal tissues, while the significant expression was found in cancer tissues in 5 cases among the 6 cases. The result suggests that G4 transcript is expressed accompanied by the malignant transformation.

TABLE 9

| Sample name | Patient No. | Tissue | Amount of transcription product G3 | G4 | G7 |
|---|---|---|---|---|---|
| LC11N | LC11 | normal | 45 | 0.01> | 0.37 |
| LC11T | LC11 | cancer | 4.2 | 1.5 | 0.082 |
| LC12N | LC12 | normal | 7.9 | 0.01> | 0.059 |
| LC12T | LC12 | cancer | 12 | 3.4 | 0.14 |
| LC15N | LC15 | normal | 8.6 | 0.01> | 0.077 |
| LC15T | LC15 | cancer | 16 | 4.8 | 0.33 |
| LC20N | LC20 | normal | 27 | 0.20 | 0.25 |
| LC20T | LC20 | cancer | 19 | 2.9 | 0.66 |
| LC23N | LC23 | normal | 3.2 | 0.01> | 0.01> |
| LC23T | LC23 | cancer | 3.9 | 0.01> | 0.12 |
| LC25N | LC25 | normal | 17 | 0.056 | 0.15 |
| LC25T | LC25 | cancer | 5.3 | 2.2 | 0.16 |

Accordingly, the same analysis was carried out on other 16 cases of lung cancer patients. Including the results of above 6 cases, expression level of G3, G4 and G7 transcripts in cancer tissues and peripheral normal tissues of lung cancer patients (22 cases) are shown in Table 10 as relative values when the amount of β-actin transcript is defined as 1,000.

The expressed amounts are shown by arranging them according to the classification of lung cancer.

Amounts of the G3, G4 and G7 transcripts in cancer tissues and peripheral normal tissues of lung cancer patients (22 cases) are shown as relative values when the amount of β-actin transcript is defined as 1,000.

TABLE 10

| Patient No. | Classification of lung cancer | Amount of G4 transcription product Normal tissue | Cancer tissue |
|---|---|---|---|
| LC2 | Adenocarcinoma | 0.01> | 0.94 |
| LC9 | Adenocarcinoma | 0.10 | 2.2 |
| LC11 | Adenocarcinoma | 0.01> | 1.2 |
| LC12 | Adenocarcinoma | 0.01> | 2.3 |
| LC13 | Adenocarcinoma | 0.01> | 9.8 |
| LC15 | Adenocarcinoma | 0.14 | 2.9 |
| LC17 | Adenocarcinoma | 0.21 | 2.0 |
| LC21 | Adenocarcinoma | 0.01> | 6.4 |
| LC24 | Adenocarcinoma | 0.01> | 0.01> |
| LC25 | Adenocarcinoma | 0.01> | 1.4 |
| LC26 | Adenocarcinoma | 0.01> | 1.7 |
| LC28 | Adenocarcinoma | 0.33 | 2.6 |
| LC8 | Adenocarcinoma (mod) | 0.01> | 5.8 |
| LC14 | Adenocarcinoma (mod) | 1.0 | 7.6 |
| LC10 | Adenocarcinoma (well) | 0.01> | 1.5 |
| LC18 | Adenocarcinoma (well) | 0.01> | 2.5 |
| LC3 | Squamouse cell carcinoma | 0.018 | 0.56 |
| LC6 | Squamouse cell carcinoma | 0.01> | 0.21 |
| LC16 | Squamouse cell carcinoma | 0.027 | 3.4 |
| LC20 | Squamouse cell carcinoma | 0.53 | 2.6 |
| LC23 | Mesothelioma | 0.21 | 0.14 |
| LC27 | Small cell carcinoma | 0.01> | 0.11 |

When an expression level (relative value) of 1 or more is regarded as "expressed", expression of G4 transcript expressed in normal tissues was seen in only one case among the total of 22 cases, and the expressed amount in this case was a low value of 1. On the other hand, G4 transcript in cancer tissues was seen in 17 cases among the total of 22 cases. Also, in the only one case in which expression of G4 transcript was found in normal tissues (LC14 in the table), the expression level in cancer tissues was increased to 7.6 evidently accompanied by the malignant transformation. When only the cases of adenocarcinoma are considered, it can be seen that expression level of G4 transcript is increased in 14 cases among the total of 15 cases (excluding LC24 in the drawing) accompanied by the malignant transformation. In squamous cell carcinoma, correlation between malignant transformation and expression level of G4 transcript was found in 2 cases among 4 cases.

The results show that G4 transcript is expressed accompanied by the malignant transformation in lung cancers (particularly in adenocarcinoma). In the only one case in which expression of G4 transcript was found in normal tissues (LC14 in the drawing), there is a possibility that the normal tissue was contaminated with a cancer tissue. Since the G4 gene is hardly expressed in normal lung tissues, it is considered that this is a gene which is expressed for the first time accompanied by the malignant transformation. In consequence, it is considered that lung cancers can be diagnosed by examining expressed amounts of the G4 gene and G4 protein in lung tissues.

INDUSTRIAL APPLICABILITY

The present invention can provide a novel polypeptide having β1,3-N-acetylglucosaminyltransferase activity; a method for producing the polypeptide; a DNA which encodes the polypeptide; a recombinant vector into which the DNA is inserted; a transformant carrying the recombinant vector; an antibody which recognizes the polypeptide; a method for determining and immunologically staining the polypeptide of the present invention, using the antibody; a method for producing a sugar chain having a GlcNAcβ1-3Gal structure, a poly-N-acetyllactosamine sugar chain and a complex carbohydrate containing the sugar chain, using the polypeptide; a method for producing a sugar chain having a GlcNAcβ1-3Gal structure, a poly-N-acetyllactosamine sugar chain and a complex carbohydrate containing the sugar chain, by using the transformant having the recombinant vector; a method for screening a substance capable of changing the expression of a gene encoding the polypeptide; a method for screening a substance capable of changing a β1,3-N-acetylglucosaminyltransferase activity of the polypeptide; a method for diagnosing inflammatory diseases and cancers (colon cancer, pancreatic cancer, gastric cancer and the like), by using the DNA or the antibody; and a method for treating inflammatory diseases and cancers (colon cancer, pancreatic cancer, gastric cancer and the like), by using the DNA, a substance capable of changing the expression of a gene encoding the polypeptide or a substance capable of changing the β1,3-N-acetylglucosaminyltransferase activity of the polypeptide.

Free Text of Sequence Listing

SEQ ID NO:8—Nucleotide sequence of G7 cNDA

SEQ ID NO:9—Explanation of synthetic sequence: Synthetic DNA

SEQ ID NO:10—Explanation of synthetic sequence: Synthetic DNA

SEQ ID NO:11—Explanation of synthetic sequence: Synthetic DNA

SEQ ID NO:12—Explanation of synthetic sequence: Synthetic DNA

SEQ ID NO:13—Explanation of synthetic sequence: Synthetic DNA

SEQ ID NO:14—Explanation of synthetic sequence: Synthetic DNA

SEQ ID NO:15—Explanation of synthetic sequence: Synthetic DNA

SEQ ID NO:16—Explanation of synthetic sequence: Synthetic DNA

SEQ ID NO:17—Explanation of synthetic sequence: Amino acid sequence of FLAG peptide SEQ ID NO:18—Explanation of synthetic sequence: Synthetic DNA SEQ ID NO:19—Explanation of synthetic sequence: Synthetic DNA SEQ ID NO:20—Explanation of synthetic sequence: Synthetic DNA SEQ ID NO:21—Explanation of synthetic sequence: Synthetic DNA SEQ ID NO:22—Explanation of synthetic sequence: Synthetic DNA SEQ ID NO:23—Explanation of synthetic sequence: Synthetic DNA SEQ ID NO:24—Explanation of synthetic sequence: Synthetic DNA SEQ ID NO:25—Explanation of synthetic sequence: Synthetic DNA SEQ ID NO:26—Explanation of synthetic sequence: Synthetic DNA SEQ ID NO:27—Explanation of synthetic sequence: Synthetic DNA SEQ ID NO:28—Explanation of synthetic sequence: Synthetic DNA SEQ ID NO:29—Explanation of synthetic sequence: Synthetic DNA SEQ ID NO:30—Explanation of synthetic sequence: Synthetic DNA SEQ ID NO:31—Explanation of synthetic sequence: Synthetic DNA SEQ ID NO:32—Explanation of synthetic sequence: Synthetic DNA SEQ ID NO:33—Explanation of synthetic sequence: Synthetic DNA SEQ ID NO:34—Explanation of synthetic sequence: Synthetic DNA SEQ ID NO:35—Explanation of synthetic sequence: Synthetic DNA SEQ ID NO:36—Explanation of synthetic sequence: Synthetic DNA SEQ ID NO:37—Explanation of synthetic sequence: Synthetic DNA SEQ ID NO:38—Explanation of synthetic sequence: Synthetic DNA SEQ ID NO:39—Explanation of synthetic sequence: Synthetic DNA SEQ ID NO:40—Explanation of synthetic sequence: Synthetic DNA

The invention claimed is:

1. A method for synthesizing poly-N-acetyllactosamine sugar chain (Galβ1-4GlcNAcβ1-3)$_n$Galβ1-4GlcNAc (n=1 or more), comprising the step of:

introducing DNA or RNA into a cell comprising a GlcNAc β1,4-galactosyltransferase, wherein said cell comprises an acceptor substrate selected from the group consisting of i) N-acetyllactosamine (Galβ1-4GlcNAc), ii) an oligosaccharide having an N-acetyllactosamine structure at its non-reducing end, and iii) a complex carbohydrate having an N-acetyllactosamine structure at its non-reducing terminal, wherein said DNA or RNA encodes a polypeptide having β1,3-N-acetylglucosaminyltransferase activity capable of transferring N-acetylglucosamine to a galactose residue present in the non-reducing terminal of said acceptor substrate via a β1,3-linkage selected from the group consisting of the following (a), (b), (c) and (d):

(a) a DNA comprising the nucleotide sequence of positions 234-1424 of SEQ ID NO:5;

(b) a DNA comprising the nucleotide sequence of positions 354-1424 of SEQ ID NO:5;

(c) a DNA hybridizing with (a) or (b) at 65° C. in the presence of 0.7 to 1.0 M sodium chloride followed by washing at 65° C. with 0.1 to 2-fold concentrated SSC solution (1-fold concentrated SSC solution contains 150 mM sodium chloride and 15 mM sodium citrate); and d) an RNA comprising a sequence corresponding to the DNA selected from any one of (a) to (c);

culturing the cell to express the polypeptide and recovering the poly-N-acetyllactosamine sugar chain produced.

2. A method for synthesizing poly-N-acetyllactosamine sugar chain (Galβ1-4GlcNAcβ1-3)$_n$Galβ1-4GlcNAc (n=1 or more), comprising the step of:

introducing DNA or RNA into a cell comprising a GlcNAc β1,4-galactosyltransferase, wherein said cell comprises an acceptor substrate selected from the group consisting of i) N-acetyllactosamine (Galβ1-4GlcNAc), ii) an oligosaccharide having an N-acetyllactosamine structure at its non-reducing end, and iii) a complex carbohydrate having an N-acetyllactosamine structure at its non-reducing terminal, wherein said DNA or RNA encodes a polypeptide having β1,3-N-acetylglucosaminyltransferase activity capable of transferring N-acetylglucosamine to a galactose residue present in the non-reducing terminal of said acceptor substrate via a β1,3-linkage selected from the group consisting of the following (a) and (b):

(a) a polypeptide comprising the amino acid sequence of SEQ ID NO: 1; and (b) a polypeptide comprising the amino acid sequence of positions 41-397 of SEQ ID NO:1;

culturing the cell to express the polypeptide and recovering the poly-N-acetyllactosamine sugar chain produced.

3. A method for synthesizing poly-N-acetyllactosamine sugar chain (Galβ1-4GlcNAcβ1-3)$_n$Galβ1-4GlcNAc (n=1 or more), comprising the step of:

introducing DNA or RNA into a cell comprising a GlcNAc β1,4-galactosyltransferase, wherein said cell comprises an acceptor substrate selected from the group consisting of i) N-acetyllactosamine (Galβ1-4GlcNAc), ii) an oligosaccharide having an N-acetyllactosamine structure at its non-reducing end, and iii) a complex carbohydrate having an N-acetyllactosamine structure at its non-reducing terminal, wherein said DNA or RNA encodes a polypeptide having β1,3-N-acetylglucosaminyltransferase activity capable of transferring N-acetylglucosamine to a galactose residue present in the non-reducing terminal of said acceptor substrate via a β1,3-linkage and comprising an amino acid sequence having 95% or more homology with a polypeptide selected from the group consisting of the following (a) and (b):

(a) a polypeptide comprising the amino acid sequence of SEQ ID NO: 1; and (b) a polypeptide comprising the amino acid sequence of positions 41-397 of SEQ ID NO:1;

culturing the cell to express the polypeptide and recovering the poly-N-acetyllactosamine sugar chain produced.

* * * * *

UNITED STATES PATENT AND TRADEMARK OFFICE

CERTIFICATE OF CORRECTION

PATENT NO. : 8,722,366 B2
APPLICATION NO. : 13/164814
DATED : May 13, 2014
INVENTOR(S) : Sasaki et al.

It is certified that error appears in the above-identified patent and that said Letters Patent is hereby corrected as shown below:

ON THE TITLE PAGE ITEM [56] REFERENCES CITED:

Other Publications,

Under T. Hennet et al., "B-N-Acetylglucosamine" should read --β-N-Acetylglucosamine--; and Under F. Kolbinger et al., "3-B-Galactosyltransferase" should read --3β-Galactosyltransferase--.

IN THE SPECIFICATION:
COLUMN 1:

Line 54, "Bosa" should read --Boca--;

Line 57, "by" should read --in--; and "and" should be deleted; and

Line 66, "facto-series" should read --lacto-series--.

COLUMN 2:

Line 22, "(Galβ1-4GlcNAβ1-" should read --(Galβ1-4GlcNAcβ1- --; and

Line 23, "(Galβ1-3GlcNAβ1-" should read --(Galβ1-3GlcNAcβ1- --.

COLUMN 3:

Line 16, "metastasis inhibiting" should read --metastasis-inhibiting--.

COLUMN 4:

Line 3, "a" should read --an--.

Signed and Sealed this
Twenty-third Day of September, 2014

Michelle K. Lee

Michelle K. Lee
*Deputy Director of the United States Patent and Trademark Office*

COLUMN 7:

Line 13, "mM294/" should read --MM294/--;

Line 14, "mM294/pBS-" should read --MM294/pBS- --;

Line 15, "mM294/pT7B-G7" should read --MM294/pT7B-G7--; and

Line 50, "accumulating" should read --accumulate--.

COLUMN 8:

Line 19, "are" should read --is--;

Line 34, "a" should read --an--;

Line 59, "GlcNAβ1-3Galβ1-4GlcNAc" should read --GlcNAcβ1-3Galβ1-4GlcNAc--;

Line 60, "GlcNAβ1-3Galβ1-3GlcNAc" should read --GlcNAcβ1-3Galβ1-3GlcNAc--;

Line 61, "GlcNAβ1-3Galβ1-4Glc" should read --GlcNAcβ1-3Galβ1-4Glc--;

Line 62, "(Galβ1-4GlcNAβ1-3)$_n$Galβ1-4GlcNAc" should read --(Galβ1-4GlcNAcβ1-3)$_n$Galβ1-4GlcNAc--; and Line 63, "(Galβ1-4GlcNAβ1-" should read --(Galβ1-4GlcNAcβ1- --.

COLUMN 9:

Line 11, "GlcNAβ1-3Galβ1-4GlcNAc" should read --GlcNAcβ1-3Galβ1-4GlcNAc--;

Line 12, "GlcNAβ1-3Galβ1-3GlcNAc" should read --GlcNAcβ1-3Galβ1-3GlcNAc--;

Line 13, "GlcNAβ1-3Galβ1-4Glc" should read --GlcNAcβ1-3Galβ1-4Glc--;

Line 14, "(Galβ1-4GlcNAβ1-3)$_n$Galβ1-4GlcNAc" should read --(Galβ1-4GlcNAcβ1-3)$_n$Galβ1-4GlcNAc--;

Line 15, "(Galβ1-4GlcNAβ1-" should read --(Galβ1-4GlcNAcβ1- --;

Line 27, "GlcNAβ1-3Galβ1-" should read --GlcNAcβ1-3Galβ1- --;

Line 28, "GlcNAβ1-3Galβ1-" should read --GlcNAcβ1-3Galβ1- --;

Line 29, "GlcNAβ1-" should read --GlcNAcβ1- --;

Line 31, "4GlcNAβ1-3)$_n$Galβ1-4GlcNAc" should read --4GlcNAcβ1-3)$_n$Galβ1-4GlcNAc--; and Line 33, "4GlcNAβ1-3)$_n$Galβ1-4Glc" should read --4GlcNAcβ1-3)$_n$Galβ1-4Glc--.

COLUMN 12:

Line 8, "cell" should read --cells--;

Line 11, "possible chromosonal" should read --possible contaminating chromosomal--; and Line 12, "of contaminating" should be deleted.

COLUMN 16:

Line 29, "which" should read --which is--.

COLUMN 17:

Line 18, "*Supplements*" should read --Supplements--.

COLUMN 19:

Line 22, "293" (2nd occurrence) should be deleted; and

Line 56, "Barathra" should read --*Barathra*-- and "*oocyte*," (both occurrences) should read --oocyte,--.

COLUMN 21:

Line 35, "sals" should read --salts--.

COLUMN 22:

Line 22, "ten" should read --tens--.

COLUMN 24:

Line 39, "protein" should read --proteins--.

COLUMN 25:

Line 42, "(Galβ1-4GlcNAβ1-3)$_n$Galβ1-4Glc" should read --(Galβ1-4GlcNAcβ1-3)$_n$Galβ1-4Glc--; and Line 47, "an" should read --a--.

COLUMN 27:

Line 13, "GlcNAβ1-3Galβ1-4Glc," should read --GlcNAcβ1-3Galβ1-4Glc,--; and "Galβ1-4(Fucα1-3)GlcNAβ1-" should read --Galβ1-4(Fucα1-3)GlcNAcβ1- --;

Line 14, "Galβ1-4GlcNAβ1-3Galβ1-4(Fucα1-3)" should read --Galβ1-4GlcNAcβ1-3Galβ1-4(Fucα1-3)--;

Line 17, "3GlcNAβ1-3Galβ1-4GlcNAc," should read --3GlcNAcβ1-3Galβ1-4GlcNAc,--; and "Galβ1-3GlcNAβ1-3Galβ1-4" should read --Galβ1-3GlcNAcβ1-3Galβ1-4--;

Line 18, "Galβ1-3GlcNAβ1-3Galβ1-4(Fucα1-3)" should read --Galβ1-3GlcNAcβ1-3Galβ1-4(Fucα1-3)--;

Line 19, "Galβ1-4GlcNAβ1-3(GlcNAβ1-6)Galβ1-4Glc," should read
--Galβ1-4GlcNAcβ1-3(GlcNAcβ1-6)Galβ1-4Glc,--;

Line 20, "Galβ1-4GlcNAβ1-3(GlcNAβ1-6)Galβ1-4GlcNAc," should read
--Galβ1-4GlcNAcβ1-3(GlcNAcβ1-6)Galβ1-4GlcNAc,--;

Line 21, "4GlcNAβ1-3(Galβ1-4GlcNAβ1-6)Galβ1-4Glc," should read
--4GlcNAcβ1-3(Galβ1-4GlcNAcβ1-6)Galβ1-4Glc,--;

Line 22, "4GlcNAβ1-3(Galβ1-4GlcNAβ1-6)Galβ1-4GlcNAc," should read
--4GlcNAcβ1-3(Galβ1-4GlcNAcβ1-6)Galβ1-4GlcNAc,--;

Line 23, "3GlcNAβ1-3(GlcNAβ1-6)Galβ1-4Glc," should read
--3GlcNAcβ1-3(GlcNAcβ1-6)Galβ1-4Glc,--; and
"Galβ1-3GlcNAβ1-3" should read --Galβ1-3GlcNAcβ1-3--;

Line 24, "(GlcNAβ1-6)Galβ1-4GlcNAc," should read --(GlcNAcβ1-6)Galβ1-4GlcNAc,--;
and "Galβ1-3GlcNAβ1-3(Galβ1-" should read --Galβ1-3GlcNAcβ1-3(Galβ1- --;

Line 25, "4GlcNAβ1-6)Galβ1-4Glc" should read --4GlcNAcβ1-6)Galβ1-4Glc-- and
"Galβ1-3GlcNAβ1-3(Galβ1-" should read --Galβ1-3GlcNAcβ1-3(Galβ1- --; and Line 26, "4GlcNAβ1-6)Galβ1-4GlcNAc," should read --4GlcNAcβ1-6)Galβ1-4GlcNAc,--.

COLUMN 28:

Line 35, "is" should read --are--.

COLUMN 32:

Line 33, "can" should be deleted.

COLUMN 33:

Line 23, "an" should read --a--.

COLUMN 36:

Line 6, "bulin K" should read --bulin κ--.

COLUMN 37:

Line 18, "poly (A)%" should read --poly $(A)^+$--.

COLUMN 38:

Line 3, "sermon" should read --salmon--.

COLUMN 40:

Line 43, “was” should read --were--.

COLUMN 41:

Line 43, “pert” should read --part--.

COLUMN 43:

Line 20, “pert” should read --part--.

COLUMN 45:

Line 22, “recognize” should read --recognizes--.

COLUMN 46:

Line 59, “were” should read --which were--.

COLUMN 47:

Line 8, “amount” should read --number--; and
Line 43, “K” should read --κ--.

COLUMN 52:

Line 57, “mmol/l” should read --50 mmol/l--.

COLUMN 54:

Line 5, “lacto-N-fucopentaose III” should read --lacto-N-fucopentaose II--;

Line 6, “GlcNAβ1-3Galβ1-4Glc,” should read --GlcNAcβ1-3Galβ1-4Glc,--;

Line 7, “Galβ1-4(Fucα1-3)GlcNAβ1-” should read --Galβ1-4(Fucα1-3)GlcNAcβ1- --;

Line 9, “(Galβ1-3GlcNAβ1-3Galβ1-4(Fucα1-3)” should read --(Galβ1-3GlcNAcβ1-3Galβ1-4(Fucα1-3)--;

Line 11, “(Galβ1-3(Fucα1-4)GlcNAβ1-3Galβ1-4” should read --(Galβ1-3(Fucα1-4)GlcNAcβ1-3Galβ1-4--;

Line 21, “were” should read --which were--;

Line 52, “[Galβ1-3(Fucα1-4)GlcNAβ1-” should read --[Galβ1-3(Fucα1-4)GlcNAcβ1- --;

Line 56, “(Fucα1-4)GlcNAβ1-3Galβ1-3(Fucα1-4)GlcNAβ1-3Galβ1-” should read --(Fucα1-4)GlcNAcβ1-3Galβ1-3(Fucα1-4)GlcNAcβ1-3Galβ1- --; and Line 64, “involved” should read --is involved--.

COLUMN 56:

Line 16, “GlcNAβ1-3Galβ1-4Glc” should read --GlcNAcβ1-3Galβ1-4Glc--;

Line 56, “Galβ1-4GlcNAβ1-3Galβ1-3GlcNAβ1-3Galβ1-4(Fucα1-3)” should read --Galβ1-4GlcNAcβ1-3Galβ1-3GlcNAcβ1-3Galβ1-4(Fucα1-3)--; and Line 57, “[Galβ1-3GlcNAβ1-” should read --[Galβ1-3GlcNAcβ1- --.

COLUMN 57:

Line 14, “4GlcNAβ1-3Galβ1-3GlcNAβ1-3Galβ1-4(Fucα1-3)Glc” should read --4GlcNAcβ1-3Galβ1-3GlcNAcβ1-3Galβ1-4(Fucα1-3)Glc--;

Line 15, “[(Galβ1-3GlcNAβ1-3Galβ1-” should read --[(Galβ1-3GlcNAcβ1-3Galβ1- --; and Line 35, “β-actinconsid-” should read --β-actin consid- --.

COLUMN 58:

Line 32, “primers,” should read --primer,--;

Line 33, “primers” should read --primer--; and

Line 66, “cDNAs” should read --cDNA--.

COLUMN 59:

Line 30, “amount” should read --number--; and

Line 39, “was” should read --were--.

COLUMN 63:

Line 66, “GlcNAβ1-3Galβ1-4Glc” should read --GlcNAcβ1-3Galβ1-4Glc--.

COLUMN 64:

Line 23, “[Galβ1-4GlcNAβ1-3]$_n$” should read --[Galβ1-4GlcNAcβ1-3]$_n$--.

COLUMN 65:

Line 58, “bands” should read --band--; and

Line 59, “of” should be deleted.

COLUMN 66:

Line 42, “type II” should read --type I--.

COLUMN 68:

Line 6, “a” should read --an--; and
Line 19, “of” should read --with--.

COLUMN 69:

Line 45, “cDNAs” should read --cDNA--; and
Line 65, “was” should read --were--.

COLUMN 70:

Line 3, “was” should read --were--;
Line 8, “was” should read --were--; and
Line 13, “was” should read --were--.

COLUMN 72:

Table 10, “Squamouse cell carcinoma” (four occurrences) should read
--Squamous cell carcinoma--.